(12) United States Patent
Wessjohann et al.

(10) Patent No.: US 6,867,333 B2
(45) Date of Patent: Mar. 15, 2005

(54) EPOTHILONE SYNTHESIS BUILDING BLOCKS III AND IV: ASYMMETRICALLY SUBSTITUTED ACYLOINS AND ACYLOIN DERIVATIVES, METHODS FOR THEIR PRODUCTION AND METHODS FOR THE PRODUCTION OF EPOTHILONES B, D AND EPOTHILONE DERIVATIVES

(75) Inventors: Ludger A. Wessjohann, Halle/Saale (DE); Gunther Scheid, Landshut (DE); Uwe Bornscheuer, Greifswald (DE); Erik Henke, Stuttgart (DE); Wouter Kuit, Neede (NL); Romano Orru, Amsterdam (NL)

(73) Assignee: Morphochem AG, Munich (DE)

( * ) Notice: Subject to any disclaimer, the term of this patent is extended or adjusted under 35 U.S.C. 154(b) by 0 days.

(21) Appl. No.: 10/414,510

(22) Filed: Apr. 15, 2003

(65) Prior Publication Data

US 2004/0082651 A1 Apr. 29, 2004

Related U.S. Application Data

(63) Continuation of application No. PCT/EP01/11992, filed on Oct. 16, 2001.

(30) Foreign Application Priority Data

Oct. 16, 2000 (DE) ......................... 100 51 136
Jul. 13, 2001 (DE) ......................... 101 34 172

(51) Int. Cl.$^7$ .................. C07C 45/00; C07C 49/04
(52) U.S. Cl. ............. 568/385; 568/414; 568/415; 568/485; 568/481
(58) Field of Search ................ 568/385, 414, 568/415, 485, 481

(56) References Cited

U.S. PATENT DOCUMENTS 4,929,760 A * 5/1990 Kitazume et al. ........... 568/308
5,545,558 A * 8/1996 Gala ........................ 435/280

OTHER PUBLICATIONS

Bianchi et al. Enzymatic Preparation of Optically Active alpha and beta–Hydroxyaldehydes. Tetrahedron, vol. 45 (3), p 869–876.*

* cited by examiner

*Primary Examiner*—Johann Richter
*Assistant Examiner*—Sikarl A. Witherspoon
(74) *Attorney, Agent, or Firm*—Knobbe, Martens, Olson & Bear, L.L.P.

(57) ABSTRACT

The present invention is directed to novel acyloins, their derivatives, methods for their production and their use for the production of novel epothilones and their derivatives. In addition, the invention is directed to the building blocks for epothilone synthesis, methods for their production and the use of synthetic building blocks for the production of epothilones and their derivatives.

19 Claims, No Drawings

EPOTHILONE SYNTHESIS BUILDING BLOCKS III AND IV: ASYMMETRICALLY SUBSTITUTED ACYLOINS AND ACYLOIN DERIVATIVES, METHODS FOR THEIR PRODUCTION AND METHODS FOR THE PRODUCTION OF EPOTHILONES B, D AND EPOTHILONE DERIVATIVES

RELATED APPLICATIONS

This application is a continuation and claims the benefit of priority of International Application No. PCT/EP01/11992 filed Oct. 16, 2001, designating the United States of America and published in German, which claims the benefit of priority of German Application No. 101 34 172.5 filed Jul. 13, 2001, and German Application No. 100 51 136.8 filed Oct. 16, 2000, all of which are hereby expressly incorporated by reference in their entireties.

FIELD OF THE INVENTION

The invention relates to acyloins, their derivatives, methods for their production and their use for the production of epothilones and their derivatives. In addition, the invention relates to the building blocks for epothilone synthesis, methods for their production and the use of synthetic building blocks for the production of epothilones and their derivatives.

BACKGROUND OF THE INVENTION

Acyloins or α-hydroxyketones (and -aldehydes) are important functional units in many biologically active substances. In addition, they are important synthetic intermediates and their small bifunctional unit is important as a site for double coupling with other synthetic building blocks, e.g. in heterocyclic chemistry.

The same applies to derivatives of acyloins, in particular those in which the hydroxy group is esterified or otherwise protected or derivatized. Acyloins with an unprotected hydroxy group are also designated as free acyloins. The keto- (or aldehyde) groups can most importantly be derivatized by acetal formation, condensation, e.g. to imines, etc., or alkenylation, e.g. by reactions of the Wittig type.

It is a common property of all α-monosubstituted acyloins and their derivatives that they have a chiral centre on the α-(OH)-Carbon atom, i.e. in the α-hydroxy position, and this can easily be racemized by the neighbouring keto group. In many acyloins, especially in free acyloins (PG=H), there can also be an acyloin shift, which is an exchange of keto and hydroxy group through an intermediate with the dihydroxyalkene structure. This, happens preferably with basic catalysis.

In the context of the present invention, an asymmetrically substituted acyloin is designated as an acyloin which bears different substituents $R^1$ and $R^2$ on the keto group and on the α-hydroxymethylene group, in other words, those compounds which form an acyloin of another structure as a result of an acyloin shift. The nomenclature of the substituents is always in relation to the standard formula, not the shift version with exchanged keto and alcohol functions, which is only depicted here for the purposes of demonstration.

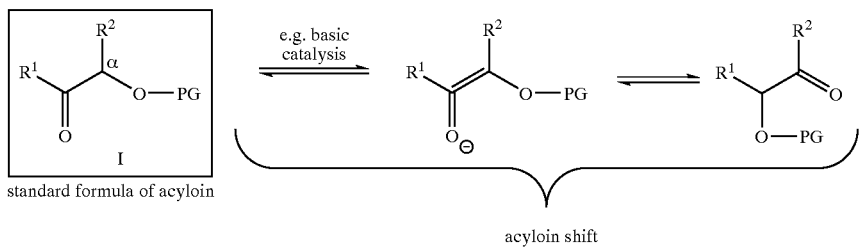

The preferred synthetic procedure for acyloins is by acyloin condensation from carboxylic acid derivatives or aldehydes, which is a procedure which is especially suitable for symmetrical acyloins. Other procedures employ the oxidation of 1,2-diols and the reduction of 1,2-dioxo compounds. The latter methods have also been performed asymmetrically and enzymatically (see e.g., Bioorg. Chemistry 21, 1993, 342; Bull. Chem. Soc. Jpn. 1994, 3314; J. Chem. Soc., Perkin Trans I 1991, 1329, ibid. 1996, 425; J. Chem. Soc., Chem. Commun. 1993; 341, J. Org. Chem. 51, 1986, 25–36; ibid. 1997, 1854). All the methods mentioned above have in common that they cannot or can only with difficulty be used for the specific synthesis of asymmetric acyloins, since cross-coupling and regioselective redox reactions are often difficult to control or to perform on a large scale (cofactors).

Acyloins and their derivatives, especially those with an allyl substituent as group $R^2$— that is homoallylacyloins (homoallylalcohols)- and with a methyl group as the preferred residue $R^1$, are also excellent building blocks for the synthesis of epothilones, where the acyloin unit is mainly found as carbon atoms C15 and C16, in accordance with the epothilone numbering system given below.

Epothilones are naturally occurring substances with extraordinary biological activity, for example as mitosis inhibitors, compounds which affect microtubular activity, cytotoxic agents and fungicides. In particular, they possess paclitaxel-like properties and even surpass the activity of paclitaxel (Taxol®) in some tests. They are now being examined in clinical studies on the treatment of cancer.

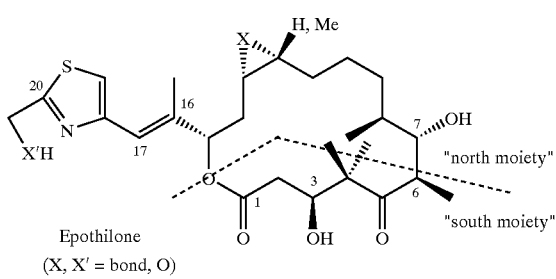

Epothilone
(X, X' = bond, O)

Epothilone, in particular epothilones B and D, possess a C7–C18(methyl) unit in the "north moiety", which corresponds to a modified polyprenyl- (polyisoprene-) chain, and can for example be synthesized in accordance with the German Patent Applications No. 197 13 970.1 and No. 100 51 136.8. There is also a C1–C6 (methyl) unit in the "south moiety", which can be synthesized by aldole type reactions, e.g. in accordance with German Patent Application No. 197 01 758.4, (1998).

The terms structural element, synthetic building block and building block, are used as synonyms in the context of the present invention. The numbering of the epothilone components is as with the epothilones (see above). In particular, substituents, especially methyl branches, are usually not mentioned separately when defining the structural elements as a C(number)-C(number) region, but are expressly included, although this is not obligatory.

Up to now, allyl compounds, including prenyl derivatives, have usually been synthesized for the production of the structural element C7–C21 of the epothilones or of subunits, especially C7–C15/16 and C11–C15/16 structural units, where the allyl compounds were coupled with C15–C16 methyl structural units which were difficult to access or in the wrong oxidation state.

Racemates are usually produced in the method for the production of the epothilone north moiety, in which the oxidation state at C15 and C16 is correct for epothilone synthesis, in particular, in accordance with German Patent Application 100 51 136.8. Therefore, all known methods for the synthesis of the epothilone north moiety exhibit the disadvantage that an asymmetric synthesis can only be performed with difficulty.

α-Hydroxyketones with at least one chiral centre on the α-hydroxy position are therefore important precursors of biologically active substances, such as polyketides and terpenoids and, in particular, epothilones and their derivatives. An economic production method is therefore of great significance.

An optimal and economic, possibly enzymatically catalyzed, production of acyloins which are not racemic at the α-hydroxy position should advantageously fulfil a series of conditions, such as for example high enantioselectivity, relative to the α-hydroxy position of the acyloin, high selectivity for diastereomers, good yield in space and time (short reaction times, high degree of conversion of the enantiomer, high educt and product concentrations), low substrate specificity for the enzyme, high chemical yield of the desired product, low quantities of catalysts (especially of enzymes), easy purification of the synthetic products, good solubility of educt and product under the reaction conditions and cheap synthesis, i.e. easily synthesizable educts, easy handling of the educts, reagents and enzymes.

As already mentioned above, structural elements C7–C16-Me of the epothilones or their subunits, in particular C7–C15 structural components, have up to now been synthesized with prenyl derivatives from nucleophilic prenyl metal derivatives, e.g. in accordance with the method disclosed in German Patent Application No. 197 13 970.1. Although this method exhibits clear advantages in comparison with other methods for the assembly of this structural element, it has the disadvantage that prenyl metal species, especially of barium, must be produced. This is expensive, tedious and leads to side-products during the reaction, e.g., from allyl shift ($S_N2'$ substitution) during the reaction. Oxidation on C15 or C16 is also necessary to introduce the oxygen function, or this function must be included in a suitable manner, which sets difficult requirements for the building blocks and often brings with it problems for later synthetic steps.

In accordance with the methods known from the art, there was often a problem in the coupling to C7 with the structural element C1–C6-Me. This should occur with syn-specificity. Previously known procedures mostly use enolates produced with base; side reactions due to these reagents are possible and/or the partners can only be coupled correctly and with an adequate yield with the help of special protecting groups or through a suitable influence of the stereocenter on C3.

SUMMARY OF THE INVENTION

It is accordingly an object of the present invention to overcome the disadvantages of the state of the art described above and, in particular, to provide a procedure which fulfils as many as possible of the conditions described above.

In particular, it is an object of the present invention to provide an alternative and improved procedure, with which preferably asymmetrically substituted acyloins and acyloin derivatives, possibly with a high excess of enantiomer in the α-hydroxy position of the acyloins, can be prepared. In addition, it is an object of the present invention to provide compounds which can be used as building blocks in the synthesis of polyketides and terpenoids, in particular of epothilones and/or their derivatives and, in particular, in which the α-hydroxy position of the acyloin unit is not racemic.

A further object of the present invention is to overcome the disadvantages in the state of the art in the synthesis of the structural elements C1–C6 or C7–C16 of the epitholones which were described above, and in particular to provide less demanding and cheaper procedures which are as free as possible from side-reactions and with which the desired structural elements are made available at yields which are as high as possible.

DETAILED DESCRIPTION OF THE PREFERRED EMBODIMENT

Further objects are derived from the following description.

The characteristics defined in the independent claims serve to solve the objects described above.

Advantageous embodiments are described in the subclaims.

The object of the invention is solved in particular, in that compounds of the general formula I:

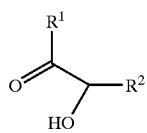

I are provided, where:

R$^1$ is selected from the group consisting of: H; alkyl; aryl; alkylaryl such as CH$_2$-aryl, C$_2$H$_4$-aryl, etc.; vinyl; alkinyl, in particular propinyl; allyl, in particular 3,3-dialkylallyl; cycloalkyl, in particular a 3- to 7-membered cycloalkyl; CH$_n$F$_{3-n}$ (n=0–3); oxacycloalkyl, in particular a 3- to 7-membered cycloalkyl and/or combinations of these; and preferably selected from the group consisting of H, methyl, ethyl and propyl; and methyl being especially preferred; and R$^2$ is selected from the group consisting of alkyl; aryl; alkyl-aryl such as CH$_2$-aryl, C$_2$H$_4$-aryl etc.; vinyl; alkinyl, in particular propinyl; allyl, in particular alkylallyl, 3,3-dialkylallyl, E- or Z-3-halogenalkyl, 3,3-dihalogenallyl; cycloalkyl, in particular a 3- to 7-membered cycloalkyl; CH$_n$F$_{3-n}$ (n=0–3); oxacycloalkyl, in particular a 3- to 7-membered oxacycloalkyl and/or combinations of these; and is preferably selected from the group consisting of propinyl, in particular alkylpropinyl; allyl, in particular 3-alkylallyl, 3,3-dialkylallyl, E- or Z-3-halogenallyl, 3,3-dihalogenallyl, and an allyl derivative of type A (coupled at X) being particularly preferred,

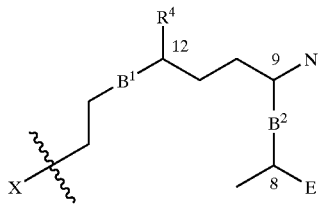

A where B$^1$ and/or B$^2$ stands for a single or triple bond; a double bond in the E-(trans) form, Z-(cis) form or E/Z mixture; an epoxide or cyclopropane ring as E-(trans) form, Z-(cis) form or E/Z mixture and/or combinations thereof; and preferably stands for single and double bonds; and where it is especially preferred that B$^1$ stands for a Z-double bond or an epoxide and B$^2$ for a single bond;

where R$^4$ is H; halogen such as F, Cl, Br or I; alkyl; aryl; alkylaryl such as CH$_2$-aryl, C$_2$H$_4$-aryl etc.; vinyl; cycloalkyl, in particular a 3- to 7-membered cycloalkyl; oxacycloalkyl, particularly a 3- to 7-membered oxacycloalkyl; and/or combinations of these; and where H, methyl, ethyl, CH$_n$F$_{3-n}$ (n=0–3), and/or halogen are preferred; and H, methyl, ethyl and/or Cl being particularly preferred;

where E is CH$_3$, CH$_2$OH, CH$_2$OPG, CH=O, CO$_2$R, CO$_2$PG, CH$_2$X, CONR$_2$, CON(PG)$_2$CON(OMe)(Me) and/or CN; and is preferably CH$_3$, CH$_2$X, CO$_2$R and/or CO$_2$PG; and is especially preferred to be CH$_2$OH, CH$_2$OPG and/or CH=O; and where Nu is R$^4$, O-PG, OR, N(PG)$_2$, N-alkyl$_2$, S-PG, S-alkyl, Se-PG, Se-alkyl, CN, N$_3$, aryl, heteroaryl; and preferably R$^4$, OPG, O-alkyl, N(PG)$_2$ and/or N-alkyl$_2$; and is especially preferred to be H and/or alkyl.

In a preferred embodiment of the present invention, the compound according to the invention is not racemic, i.e. is optically active at the α-hydroxy position of the general formula I. The compounds in accordance with the invention are in this embodiment particularly suitable for the economic synthesis of polyketides and terpenoids, in particular of epothilones and their derivatives, since a high enantioselectivity and diastereomeric selectivity is guaranteed in this way, which, in particular, makes clinical use of the final products possible.

However, compounds as described above which are racemic at the α-hydroxy position of the general formula I are also the subject of the present invention.

Residue R$^2$ in general formula I is preferably selected from the group consisting of propinyl-, propargyl- and allyl residues.

It is especially preferred that the residue R$^2$ in the general formula I is an alkylpropinyl residue and the compound is racemic and/or not racemic at the α-hydroxy position of the general formula I.

If residue R$^2$ in the general formula I is an allyl residue, R$^2$ is selected from the group consisting of 3-alkylallyl, 3,3-dialkylallyl, E- or Z-3-halogenallyl and 3,3-dihalogenallyl.

In an especially preferred compound according to the invention, residue R$^2$ in the general formula I contains an allyl derivative of type A (coupled to formula I at X):

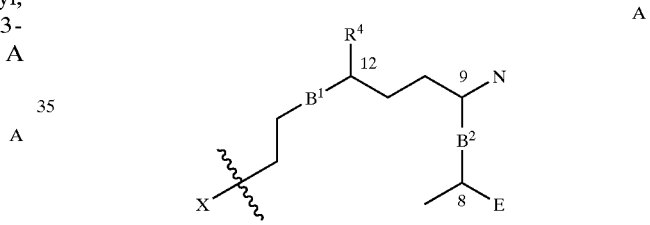

A where

B$^1$ and/or B$^2$ stands for a single or triple bond; a double bond in the E-(trans) form, Z-(cis) form or a E/Z mixture; an epoxide or cyclopropane ring in the E-(trans) form, Z-(cis) form or E/Z mixture and/or combinations of these; and stands preferably for single and double bonds; and B$^1$ is especially preferred to be a Z-double bond or an epoxide and B$^2$ a single bond;

R$^4$ is H; halogen such as F, Cl, Br or I; alkyl; aryl; alkylaryl such as CH$_2$-aryl, C$_2$H$_4$-aryl etc.; vinyl; cycloalkyl, in particular a 3- to 7-membered cycloalkyl; oxacycloalkyl, in particular a 3- to 7-membered oxacycloalkyl; and/or combinations of these; and is preferably H, methyl, ethyl, CH$_n$F$_{3-n}$ (n=0–3), and/or halogen; and is especially preferred to be H, methyl, ethyl and/or Cl;

E is CH$_3$, CH$_2$OH, CH$_2$OPG, CH=O, CO$_2$R, CO$_2$PG, CH$_2$X, CONR$_2$, CON(PG)$_2$CON(OMe)(Me) and/or CN; and is preferably CH$_3$, CH$_2$X, CO$_2$R and/or CO$_2$PG; and is especially preferred to be CH$_2$OH, CH$_2$OPG and/or CH=O; and Nu is R$^4$, O-PG, OR, N(PG)$_2$, N-alkyl$_2$, S-PG, S-alkyl, Se-PG, Se-alkyl, CN, N$_3$, aryl, heteroaryl; and R$^4$ is preferably OPG, O-alkyl, N(PG)$_2$ and/or N-alkyl$_2$; and is especially preferred to be H and/or alkyl.

For use as epothilone building blocks, it is especially advantageous, if residue R$^2$ or A is selected from the group consisting of a neryl and a geranyl residue, especially from the group consisting of a neryl or geranyl derivative which is oxidized at the ω-position to an alcohol, aldehyde or carboxylic acid and/or ω-1/2-hydrated. Examples for the residue $R^2$ can therefore be selected from the group consisting of an ω-hydroxy- and an ω-oxo-ω-1/2)-dihydroneryl residue.

It is also of particular advantage with respect to possible use of the compounds in accordance with the invention in the synthesis of the epothilone north moiety, if the absolute configuration of the α-hydroxy position of the general formula I corresponds to the natural configuration of the epothilones at position C15.

In another possible embodiment of the present invention, the α-hydroxy group of the general formula I is protected by a protecting group PG, particularly an acyl group. It is especially preferred that the protecting group, PG, is selected from the group consisting of the acetyl, propionyl, butyroyl and benzoyl groups.

One example of a compound in accordance with the invention is shown in the general formula III

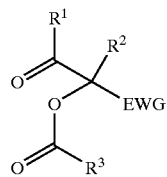

III where $R^2$ is propinyl and/or propinyl derivatives of type $CH_2-C\equiv C-R$ with R=alkyl, homoallyl, $CH_2X$;

$R^3$ is selected from the group consisting of alkyl; aryl; alkylaryl such as $CH_2$-aryl, $C_2H_4$-aryl etc.; alkoxyalkyl; fluoroalkyl; and is preferably selected from the group consisting of alkyl, benzyl and phenyl; and is especially preferably selected from the group consisting of methyl, ethyl and propyl; and EWG is an electronegative functional group such as $CO_2R$, $CO_2PG$, CN, CO—R, alkylphosphonate, $SO_2-R$, $SO_2OR$, preferably $CO_2R$, $CO_2PG$, and especially preferred to be $CO_2$-tBu.

A further example of the compounds in accordance with the invention is exhibited in the general formula IV

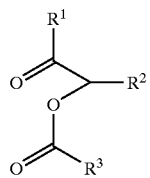

IV where $R^2$ is propinyl and/or propinyl derivatives of type $CH_2-C\equiv C-R$ with R=alkyl, homoallyl, $CH_2X$; and $R^3$ is selected from the group consisting of alkyl; aryl; alkylaryl such as $CH_2$-aryl, $C_2H_4$-aryl etc.; alkoxyalkyl; fluoroalkyl; and preferably selected from the group consisting of alkyl, benzyl and phenyl; and especially preferred to be selected from the group consisting of methyl, ethyl and propyl.

In a further aspect of the present invention, a compound is made available in which the α-hydroxy group of the general formula I

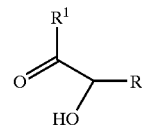

I is protected by a non-racemic chiral acyl group, where $R^1$ is selected from the group consisting of H; alkyl; aryl; alkylaryl such as $CH_2$-aryl, $C_2H_4$-Aryl etc.; vinyl; alkinyl, in particular propinyl; allyl, in particular 3,3-dialkylallyl; cycloalkyl, in particular a 3- to 7-membered cycloalkyl; $CH_nF_{3-n}$ (n=0–3); oxacycloalkyl, in particular a 3- to 7-membered cycloalkyl and/or combinations of these; and preferably selected from the group consisting of H, methyl, ethyl and propyl; and where methyl is especially preferred; and $R^2$ is selected from the group consisting of alkyl; aryl; alkylaryl such as $CH_2$-aryl, $C_2H_4$-aryl etc.; vinyl; alkinyl, in particular propinyl; allyl, in particular alkylallyl, 3,3-dialkylallyl, E- or Z-3-halogenalkyl, 3,3-dihalogenallyl; cycloalkyl, in particular a 3- to 7-membered cycloalkyl; $CH_nF_{3-n}$ (n=0–3); oxacycloalkyl, in particular a 3- to 7-membered oxacycloalkyl and/or combinations of these; and is preferably selected from the group consisting of propinyl, in particular alkylpropinyl; allyl, in particular 3-alkylallyl, 3,3-dialkylallyl, E- or Z-3-halogenallyl, 3,3-dihalogenallyl, and where an allyl derivative of type A (coupled at X) is especially preferred,

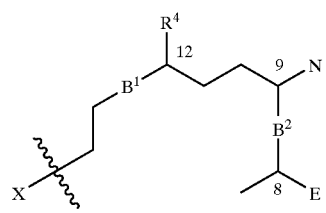

A where $B^1$ and/or $B^2$ stand for a single or triple bond; a double bond as E-(trans) form, Z-(cis) form or E/Z mixture; an epoxide or cyclopropane ring as E-(trans) form, Z-(cis) form or E/Z mixture and/or combinations of these; and stands preferably for single and double bonds; and $B^1$ especially preferably stands for a Z-double bond or epoxide and $B^2$ for a single bond;

$R^4$ is H; halogen such as F, Cl, Br or I; alkyl; aryl; alkylaryl such as $CH_2$-aryl, $C_2H_4$-aryl etc.; vinyl; cycloalkyl, in particular a 3- to 7-membered cycloalkyl; oxacycloalkyl, in particular a 3- to 7-membered oxacycloalkyl; and/or combinations of these; and is preferably H, methyl, ethyl, $CH_nF_{3-n}$ (n=0–3), and/or halogen; and where H, methyl, ethyl and/or Cl are especially preferred;

E is $CH_3$, $CH_2OH$, $CH_2OPG$, CH=O, $CO_2R$, $CO_2PG$, $CH_2X$, $CONR_2$, $CON(PG)_2CON(OMe)(Me)$ and/or CN; and is preferably $CH_3$, $CH_2X$, $CO_2R$ and/or $CO_2PG$; and is especially preferably $CH_2OH$, $CH_2OPG$ and/or CH=O; and Nu is $R^4$, O-PG, OR, $N(PG)_2$, $N$-alkyl$_2$, S-PG, S-alkyl, Se-PG, Se-alkyl, CN, $N_3$, aryl, heteroaryl; and is preferably $R^4$, OPG, O-alkyl, $N(PG)_2$ and/or $N$-alkyl$_2$; and is especially preferably H and/or alkyl.

Compounds of this sort with non-racemic acyl groups in the α-hydroxy position are especially suitable as building blocks for the synthesis of polyketides and terpenoids, epothilones and/or their derivatives, since they allow diastereomeric separation of the synthetic building blocks and, as a consequence, after removal of the acyl group, provide the production of enantiomerically enriched acyloins or acyloin derivatives and other building blocks for the epithilones.

In particular, the α-hydroxy group of the general formula I is protected by a non-racemic chiral acyl group selected from the group consisting of 2-alkoxy and 2-(N,N-di-PG-amino)acyl groups. Esterification of the α-hydroxy group of general formula I with optically active 2-alkoxymandelic acid or with 2-alkoxylactic acid and, especially, 2-methoxymandelic acid as non-racemic protecting group is particularly preferred.

Further examples of non-racemic chiral protecting groups, in particular non-racemic chiral acyl groups, are known to the person skilled in the art.

In a further aspect of the present invention, a compound of the general formula VI is provided,

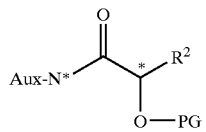

VI where

Aux-N* is N—O-alkyl, preferably N—O-methyl, and/or an Evans type auxiliary of the oxazolidinone or imidazolidinone type;

and $R^2$ is an allyl derivative of the type A (coupled at X)

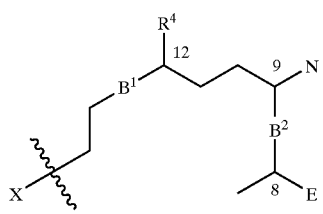

A where $B^1$ and/or $B^2$ stand for a single or triple bond; a double bond as E-(trans) form, Z-(cis) form or E/Z mixture; an epoxide or cyclopropane ring as E-(trans) form, Z-(cis) form or E/Z mixture and/or combinations of these; and stands preferably for single and double bonds; and $B^1$ stands especially preferably for a Z-double bond or an epoxide and $B^2$ for a single bond;

$R^4$ is H; halogen such as F, Cl, Br or I; alkyl; aryl; alkylaryl such as $CH_2$-aryl, $C_2H_4$-aryl etc.; vinyl; cycloalkyl, in particular a 3- to 7-membered cycloalkyl; oxacycloalkyl, in particular a 3- to 7-membered oxacycloalkyl; and/or combinations of these; and is preferably H, methyl, ethyl, $CH_nF_{3-n}$ (n=0–3), and/or halogen; and is especially preferably H, methyl, ethyl and/or Cl;

E is $CH_3$, $CH_2OH$, $CH_2OPG$, $CH\!=\!O$, $CO_2R$, $CO_2PG$, $CH_2X$, $CONR_2$, $CON(PG)_2CON(OMe)(Me)$ and/or CN; and is preferably $CH_3$, $CH_2X$, $CO_2R$ and/or $CO_2PG$; and is especially preferably $CH_2OH$, $CH_2OPG$ and/or $CH\!=\!O$; and Nu is $R^4$, O-PG, OR, $N(PG)_2$, N-alkyl$_2$, S-PG, S-alkyl, Se-PG, Se-alkyl, CN, $N_3$, aryl, heteroaryl; and is preferably $R^4$, OPG, O-alkyl, $N(PG)_2$ and/or N-alkyl$_2$; and is especially preferably H and/or alkyl, and residue $R^2$ is preferably selected from the group consisting of a neryl and a geranyl residue, and where it is especially preferred to select residue $R^2$ from the group consisting of a neryl or geranyl derivative which is oxidized at the ω-position to an alcohol, aldehyde or carboxylic acid and/or ω-1/2-hydrated, and where it is especially preferred to select $R^2$ from the group consisting of ω-hydroxy- and ω-oxo.(ω-1/2)-dihydroneryl; and PG' is selected from the group consisting of H and protecting groups, which do not react during the conventional enolization of the auxiliary modified intermediates and which is preferably selected from the group consisting of silyl, benzyl and oxymethyl derivatives.

With the acyloins or acyloin derivatives which contain an Evans type auxiliary group as described above in accordance with the invention, it is also possible to carry out enantiomerically enriched synthesis of polyketides and terpenoids, epothilones and/or their derivatives.

The Evans-type auxiliary, Aux-N*, is preferably an optically active oxazolidinone or N-methylimidazolidinone with the general formula

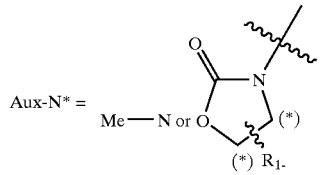

where

R is on positions 4 and 5, the chirality centres of the oxazolidinone or N-methylimidazolidinone, and is selected from the group consisting of methyl, phenyl, isopropyl, benzyl, polymeric residues and combinations of these.

As an example, the Evans type auxiliary may be derived from ephedrines.

In a further aspect of the present invention, a compound with the general formula V:

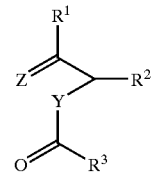

V is provided, where

Y is selected from a group consisting of S, NH, N-PG, NR, O; and is preferably selected from a group consisting of NH, N-PG, NR and O; and where O is especially preferred;

$R^1$ is selected from the group consisting of: H; alkyl; aryl; alkylaryl such as $CH_2$-aryl, $C_2H_4$-aryl etc.; vinyl;

alkinyl, in particular propinyl; allyl, in particular 3,3-dialkylallyl; cycloalkyl, in particular a 3- to 7-membered cycloalkyl; $CH_nF_{3-n}$ (n=0–3); oxacycloalkyl, in particular a 3- to 7-membered cycloalkyl and/or combinations of these; and preferably selected from the group consisting of H, methyl, ethyl and propyl; and where methyl is especially preferred; and $R^2$ is selected from a group consisting of: alkyl; aryl; alkylaryl such as $CH_2$-aryl, $C_2H_4$-aryl etc.; vinyl; alkinyl, in particular propinyl; allyl, in particular alkylallyl, 3,3-dialkylallyl, E- or Z-3-halogenalkyl, 3,3-dihalogenallyl; cycloalkyl, in particular a 3- to 7-membered cycloalkyl; $CH_nF_{3-n}$ (n=0–3); oxacycloalkyl, in particular a 3- to 7-membered oxacycloalkyl and/or combinations of these; and is preferably selected from the group consisting of propinyl, in particular alkylpropinyl; allyl, in particular 3-alkylallyl, 3,3-dialkylallyl, E- or Z-3-halogenallyl, 3,3-dihalogenallyl, and where an allyl derivative of type A (coupling at X) is especially preferred,

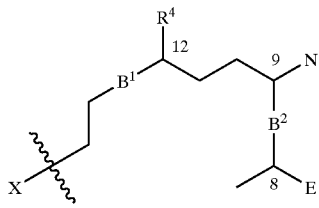

A where

B¹ and/or B² stands for a single or triple bond; a double bond as the E-(trans) form, Z-(cis) form or E/Z mixture; an epoxide or cyclopropane ring as E-(trans) form, Z-(cis) form or E/Z mixture and/or combinations of these; and preferably stands for single and double bonds; and B1 especially preferably stands for a Z-double bond or an epoxide and B² for a single bond;

$R^4$ is H; halogen such as F, Cl, Br or I; alkyl; aryl; alkylaryl such as $CH_2$-Aryl, $C_2H_4$-aryl etc.; vinyl; cycloalkyl, in particular a 3- to 7-membered cycloalkyl; oxacycloalkyl, in particular a 3- to 7-membered oxacycloalkyl; and/or combinations of these; and is preferably H, methyl, ethyl, $CH_nF_{3-n}$ (n=0–3), and/or halogen; and is especially preferably H, methyl, ethyl and/or Cl;

E is $CH_3$, $CH_2OH$, $CH_2OPG$, $CH=O$, $CO_2R$, $CO_2PG$, $CH_2X$, $CONR_2$, $CON(PG)_2CON(OMe)(Me)$ and/or CN; and is preferably $CH_3$, $CH_2X$, $CO_2R$ and/or $CO_2PG$; and is especially preferably $CH_2OH$, $CH_2OPG$ and/or $CH=O$; and Nu is $R^4$, O-PG, OR, $N(PG)_2$, $N$-alkyl$_2$, S-PG, S-alkyl, Se-PG, Se-alkyl, CN, $N_3$, aryl, heteroaryl; and is preferably $R^4$, O-PG, O-alkyl, $N(PG)_2$ and/or $N$-alkyl$_2$; and is especially preferably H and/or alkyl;

$R^3$ is selected from the group consisting of alkyl; aryl; alkylaryl such as $CH_2$-aryl, $C_2H_4$-aryl etc.; alkoxyalkyl; fluoroalkyl; and is preferably selected from the group consisting of alkyl, benzyl and phenyl; and is especially preferably selected from the group consisting of methyl, ethyl and propyl; and Z is selected from the group consisting of $=O$, $=N$-Nu, $=CH$-hetaryl, $=CH$-aryl and $=PR_3$; and is preferably $=CH$-hetaryl; and is especially preferably selected from the group consisting of (E)-(2-methylthiazol-4-yl)-CH= and (E)-(2-methyloxazol-4-yl)-CH=; where all groups Z may be present in the (E) form, (Z) form or as a (E/Z) mixture.

A compound of this type with the general formula V, in particular when it is not racemic, i.e. is optically active at the α-position and/or Z is a carbonyl residue, is an especially preferred structural element for epothilone synthesis.

It is a further subject of the present invention to provide a method for the production of the α-hydroxyketone compounds, as described above and in accordance with the invention, that includes at least one of the following steps:

a) Conversion of compounds of general formula II,

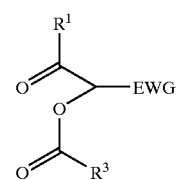

II where $R^1$ is selected from a group consisting of H; alkyl; aryl; alkylaryl such as $CH_2$-aryl, $C_2H_4$-aryl etc.; vinyl; alkinyl, in particular propinyl; allyl, especially 3,3-dialkylallyl; cycloalkyl, in particular a 3- to 7-membered cycloalkyl; $CH_nF_{3-n}$ (n=0–3); oxacycloalkyl, in particular a 3- to 7-membered cycloalkyl; Aux-N*, where Aux-N* is selected from a group consisting of N—O-alkyl, preferably N—O-methyl, and an Evans type auxiliary of the oxazolidinone or imidazolidinone type, preferably an optically active oxazolidinone or N-methylimidazolidinone with the general formula

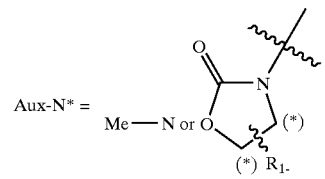

where

R on positions 4 and/or 5 of the oxazolidinone or imidazolidinone is selected from a group consisting of methyl, phenyl, isopropyl, benzyl, polymeric residues and combinations of these; and $R^1$ is preferably selected from the group consisting of H, methyl, ethyl and propyl; and $R^1$ is especially preferably methyl;

$R^3$ is selected from the group consisting of alkyl; aryl; alkylaryl such as $CH_2$-aryl, $C_2H_4$-aryl etc.; alkoxyalkyl; fluoroalkyl; and is preferably selected from the group consisting of alkyl, benzyl and phenyl; and is especially preferably selected from the group consisting of methyl, ethyl and propyl; and EWG is an electronegative functional group such as $CO_2R$, $CO_2PG$, CN, CO—R, alkylphosphonate, $SO_2$—R, $SO_2OR$ and is preferably $CO_2R$, $CO_2PG$, and is especially preferably $CO_2$-t-Bu;

with residues $R^2$, selected from the group consisting of alkyl; aryl; alkylaryl such as $CH_2$-aryl, $C_2H_4$-aryl etc.; vinyl; alkinyl, in particular propinyl; allyl, in particular alkylallyl, 3,3-dialkylallyl, E- or Z-3-halogenalkyl, 3,3- dihalogenallyl; cycloalkyl, in particular a 3- to 7-membered cycloalkyl; $CH_nF_{3-n}$ (n=0–3); oxacycloalkyl, in particular a 3- to 7-membered oxacycloalkyl and/or combinations of these; and is preferably selected from the group consisting of propinyl, in particular alkylpropinyl; allyl, in particular 3-alkylallyl, 3,3-dialkylallyl, E- or Z-3-halogenallyl, 3,3-dihalogenallyl, and is especially preferred an allyl derivative of type A (coupled at X),

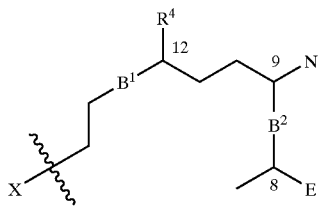

A where

- $B^1$ and/or $B^2$ stands for a single or triple bond; a double bond as E-(trans) form, Z-(cis) form or E/Z mixture; an epoxide or cyclopropane ring as E-(trans) form, Z-(cis) form or E/Z mixture and/or combinations of these; and preferably stands for single and double bonds; and $B^1$ especially preferably stands for a Z-double bond or an epoxide and $B^2$ for a single bond;

- $R^4$ is H; halogen such as F, Cl, Br or I; alkyl; aryl; alkylaryl such as $CH_2$-aryl, $C_2H_4$-aryl etc.; vinyl; cycloalkyl, in particular a 3- to 7-membered cycloalkyl; oxacycloalkyl, in particular a 3- to 7-membered oxacycloalkyl; and/or combinations of these; and is preferably H, methyl, ethyl, $CH_nF_{3-n}$ (n=0–3), and/or halogen; and especially preferably H, methyl, ethyl and/or Cl;

- E is $CH_3$, $CH_2OH$, $CH_2OPG$, CH=O, $CO_2R$, $CO_2PG$, $CH_2X$, $CONR_2$, $CON(PG)_2CON(OMe)(Me)$ and/or CN; is preferably $CH_3$, $CH_2X$, $CO_2R$ and/or $CO_2PG$; and is especially preferably $CH_2OH$, $CH_2OPG$ and/or CH=O; and

- Nu is $R^4$, O-PG, OR, $N(PG)_2$, N-alkyl$_2$, S-PG, S-alkyl, Se-PG, Se-alkyl, CN, $N_3$, aryl, heteroaryl; and is preferably $R^4$, OPG, O-alkyl, $N(PG)_2$ and/or N-alkyl$_2$; and is especially preferably H and/or alkyl;

to compounds with the general formula III

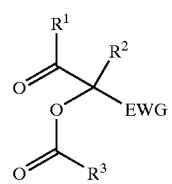

III b) Conversion of compounds with the general formula III to compounds with the general formula IV

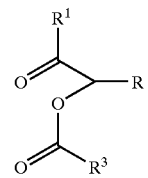

IV for example, by alkyldecarboxylation or saponification/decarboxylation of compounds of general formula III with EWG=$CO_2R$ or $CO_2PG$, preferably according to the Krapcho method known to the person skilled in the art, and especially preferred starting from III with EWG=$CO_2tBu$ in the presence of suitably strong acids, preferably volatile and/or anhydrous acids, with trifluoracetic acid being especially preferred;

c) Solvolysis of the compound of general formula IV to free α-hydroxyketones of the general formula I

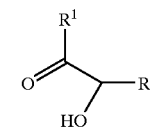

I in the presence of suitable solvents and possibly suitable catalysts, and/or d) Racemate separation by esterification of compounds of the general formula I.

The steps in the procedure described above a) to d) can be performed in any order with which the person skilled in the art is familiar, with the sequence given being preferred. In addition, one or more of the steps can be left out, depending on the product desired.

The conversion of compounds of the general formula II with residues $R^2$ is carried out for example by propinylation or allylation, as is familiar to the person skilled in the art, where the residues $R^2$ are provided on their site of coupling with, preferably, H; OH; or halogen or other conventional leaving groups and their combinations; preferably Cl, Br, I, O-tosyl, methylsulfonate, trifluormethylsulfonate, alkanoate and, arylcarboxylate; and especially preferred H, Cl, Br.

In particular, the solvolysis in step c) of the procedure according to the invention is carried out by hydrolysis with water and/or transesterification with alcohols.

Possible catalysts for the solvolysis in step c) are basic, acid and/or Lewis acid catalysts. The catalysts are preferably selected from the group consisting of alkali hydroxides, alkaline earth hydroxides, alkali hydrogen carbonates, alkaline earth hydrogen carbonates, alkali carbonates, alkaline earth carbonates, inorganic acids, organic acids, especially aromatic sulfonic acids or polymer-bound acids, and Lewis acid catalysts such as lanthanide salts, titanium salts, in particular titanium(IV) alkoxides.

In keeping with their chemical properties, some Lewis acid catalysts can only be used under exclusion of water.

Suitable solvents are known to the person skilled in the art. Examples will be given below in connection with other methods according to the invention for the synthesis of synthetic building blocks for the synthesis of epothilones.

The reaction temperature lies in the range from −80° C. to 150° C., depending on the reactivity and solvent system, preferably however in the range from 0° C. to 90° C., and particularly preferably in the range from 15° C. to 35° C.

The preparation is usually carried out by shaking out with conventional organic solvents, drying and possibly purification by distillation, crystallization and/or chromatography.

In addition, it is preferred that the solvolysis in step c) is performed by mildly basic hydrolysis with mildly basic catalysts, preferably in aqueous and/or alcoholic solutions, with higher alkali carbonates or dilute alkali hydroxides as catalysts, and the dosage during the reaction should preferably be adjusted during the reaction so that the pH value does not exceed that of a carbonate solution. The reaction is carried out preferably in methanol or ethanol with aqueous sodium or potassium carbonate solution.

In other embodiments which are described below, procedures in accordance with the invention are described, by which non-racemic asymmetrically substituted acyloins and acyloin esters and their derivatives can be synthesized, using asymmetric synthesis or racemate separation, preferably however using enzymatic and/or physicochemical racemate separation, and preferably concerning those derivatives which can serve as building blocks for epothilone synthesis, in particular those which are described in the German Patent Application 100 51 136.8, hereby incorporated by reference.

Racemate separation has as yet only been rarely performed on acyloins, almost exclusively on symmetrical acyloins, without problems related to the acyloin shift or with inferior results with respect to the purity of the enantiomers and/or yield and/or specific rotation, and/or greater difficulty than in the procedure described below (see e.g. J. Chem. Soc. Chem. Commun. 1997, 1399; Tetrahedron: Asymmetry 10, 1996, 2207; ibid. 1997, 2773; Tetrahedron Lett. 1997, 6429). Moreover, there are few examples of racemate separation for homoallylalcohols (e.g. Tetrahedron: Asymmetry 10, 1999, 315). Also, the C15 racemate separation of advanced epothilone north moieties with thiazolmethylidene side chains only gives an inadequate enantiomer excess (Tetrahedron Lett. 41, 2000, 1863–1866; s.a. Synthesis 1999, 1469). The combination to homoallylacyloins, i.e. allylically substituted acyloins ($R^2$= allyl and derivatives, in particular Y), is an especially important combination for epothilone building blocks, but has not yet been successfully submitted to enzymatic racemate separation. In particular, for this racemate separation, substrates with protected and sometimes unprotected functional groups (e.g., 7-OH) must be converted, which allow the subsequent conversion to epothilones and epothilone derivatives.

As will be described below, suitable conditions and especially suitable enzymes will be made available for these conversions in the context of the present invention and for the first time. Moreover, it was found for the first time that certain enzymes which had been genetically modified by in vitro evolution can be advantageously used for the synthesis of these nonracemic epothilone north moiety components.

The following illustration gives a schematic example of the synthesis of racemic acyloin precursors and acyloins:

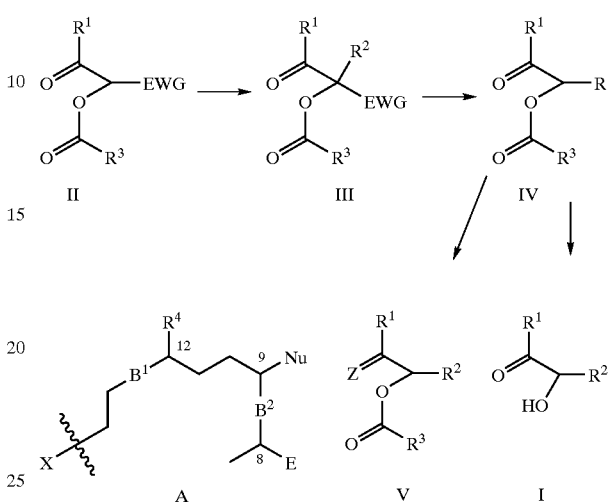

It was surprisingly found that the use of certain nonracemic acyloxy groups as protective groups for the α-hydroxy group of acyloins or acyloin derivatives allows the separation of the diastereomers of acyloin precursors and/or protected acyloins, so that the synthesis of enantiomer-enriched acyloins or acyloin derivatives or possibly advanced epithilone building blocks is possible after hydrolysis or other conversion. In particular, it was then established that this conversion from the diastereomers was successful with the total or predominant retention of the enantiomer excess.

The following illustration depicts an idealized separation of the diastereomers:

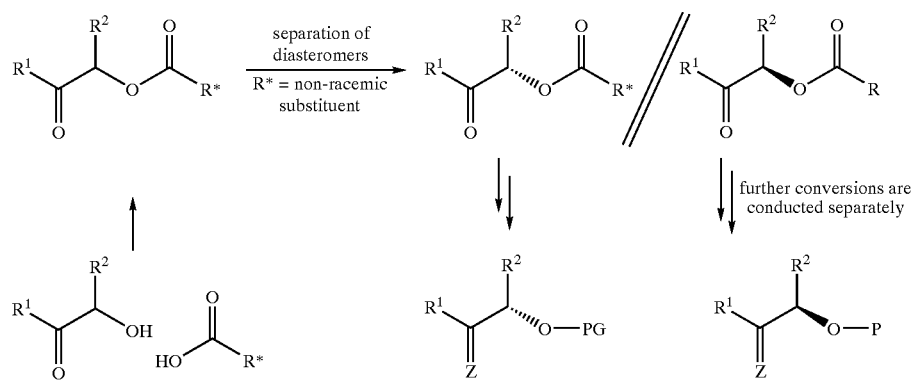

In an especially preferred embodiment of the present invention, a method is provided in which the production of compounds of the general formula I which are not racemic at the α-hydroxy position is performed by the conversion of compounds with the general formulae II, III and IV, in which the α-hydroxy group is protected by a non-racemic chiral acyl group ($R^3$=R*).

In particular, in this embodiment the α-hydroxy group can be esterified with optically active 2-alkoxymandelic acid or 2-alkoxylactic acid, and preferably with 2-methoxymandelic acid.

In addition, it was found in the context of the present invention that the auxiliary-regulated synthesis of acyloins of this type with 2-oxysubstituted acetylderivatives is successful, analogously to the Evans method.

The following illustration depicts an "enantioselective" synthesis of acyloins (N-Aux=chiral auxiliary of the Evans type, preferably oxazolidinone or in particular imidazolidinone derivatives):

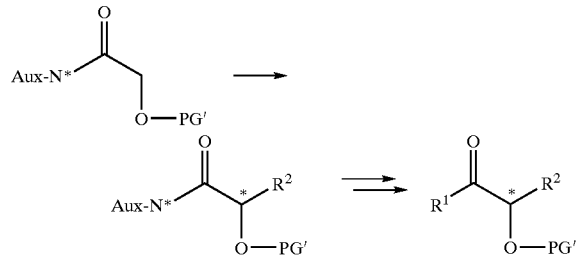

Thus, in an alternative embodiment of the procedure in accordance with the invention, the production of compounds of the general formula I which are non-racemic at the α-hydroxy position is performed through intermediate products in the form of compounds of the general formula VI

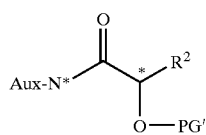

VI with possible subsequent purification by chromatography, where PG' is selected from the group consisting of H and protecting groups, which do not react during the conventional enolization of the auxiliary modified intermediates and which is preferably selected from the group consisting of silyl, benzyl and oxymethyl derivatives.

In this embodiment, the compounds with the general formula VI are in particular provided by conversion of non-racemic 4- and/or 5-substituted N—[O-PG]-acetyl-N-methylimidazolidinones, in which PG is a protecting group, with α-hydroxyketone compounds, possibly in the presence of base, preferably lithium dialkylamides and/or alkali hexamethyldisilazides. The α-hydroxyketone compounds include the residue $R_2$, in particular the residue Y, where neryl derivatives are especially preferred, and suitable leaving groups X.

The purification and possible separation of the diastereomers occurs preferably by liquid chromatographic separation on achiral solid phases such as silica gel.

Especially preferred is the production of compounds of the general formula I which are not racemic on the α-hydroxy position by addition of organometallic compounds, preferably of alkyllithium or alkylmagnesium compounds, especially preferred being methyl- or ethyl-lithium or methyl or ethyl Grignard reagents, to compounds of the general formula VI.

It was also surprisingly found that racemic free acyloin can be enzymatically esterified to O-acylacyloins, with partial, preferably predominant and especially preferably almost complete, separation of the racemate.

The following illustration shows an idealized depiction of enzymatic esterification with separation of the racemate:

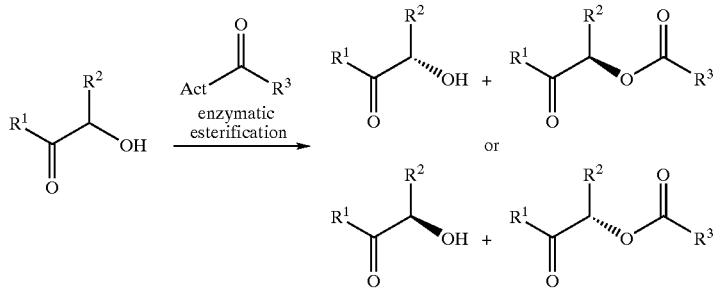

Thus, a further alternative and especially preferred embodiment of the method in accordance with the invention is the production of compounds of the general formulae I or IV, which are non-racemic at the α-hydroxy position, by separation of the racemates by enzymatic esterification of compounds of the type I.

In particular, the esterification is carried out with an active ester, preferably isopropenyl and/or vinyl acetate.

The enzymes which catalyze the esterification are preferably selected from the group consisting of lipases and esterases, for example lipases from *Pseudomonas cepacia* and/or *Candida antarctica*.

Alternatively, esterases from *Pseudomonas fluorescens* and/or *Streptomyces diastatochromogenes* are used.

For example, a solution of the acyloin in a suitable organic solvent, preferably an alkane, especially preferred toluene, is made to react; with a lipase or esterase, which may be immobilised or processed in another manner, preferably a lipase; and an active ester, preferably isopropenyl or vinyl acetate, especially preferred at a slight excess; preferably at 10–70° C., especially preferred at the enzymatic optimum or in a range plus/minus 10° C. round the enzymatic optimum, possibly with shaking, preferably with shear-free stirring or shaking, until the desired conversion has taken place. The reaction is ended by preparation, preferably by centrifugation, the solvent is taken off and removed by vacuum distillation. The ester and unreacted free acyloin can be separated by distillation, crystallization or chromatography, preferably solid phase chromatography, e.g. silica gel or aluminium oxide.

In the context of the present invention, it was also surprisingly found that with racemic O-acylated acyloins (PG=acyl, preferably acetyl, butyryl, benzoyl) it is possible, alternatively and with success, to use enzymatic hydrolysis to separate the racemates, giving non-racemic free acyloin and non-racemic O-acylacyloin of the opposite stereochemistry.

The following illustration gives an idealized depiction of an enzymatic hydrolytic racemate separation of this sort:

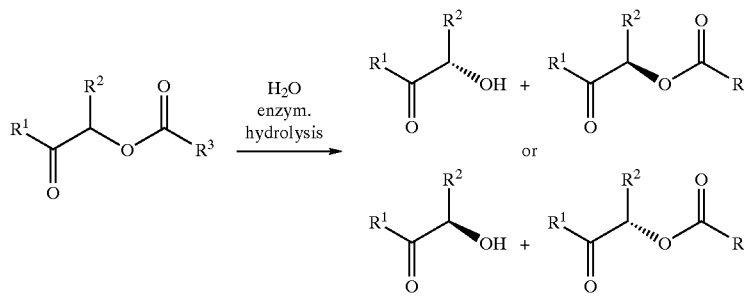

Thus a further alternative and also preferred embodiment of the procedure according to the invention is the production of compounds of the general formulae I or IV which are non-racemic in the α-hydroxy position by enzymatic hydrolytic racemate separation of compounds of type IV.

The enzyme catalysing the hydrolysis is preferably selected from the group consisting of lipases and esterases. For example, the lipases from *Pseudomonas cepacia* and/or *Candida antarctica* can be used. Alternatively, esterases from *Pseudomonas fluorescens* and/or *Streptomyces diastatochromogenes* are advantageous. Recombinant pig liver esterase is especially preferred.

For example, in this embodiment an ester of general formula IV is dissolved or suspended in a buffer, preferably a phosphate or carbonate buffer; the hydrolase, preferably a lipase or esterase, possibly in an immobilized or other processed form, is then added. In larger batches, buffering can be carried out, preferably by the pH-controlled addition of base. The pH value depends on the known or determined optimum and threshold values of the enzyme, where a pH value between these values is ideal when it allows optimal reaction control. The reaction is carried out preferably between 10–70° C., especially preferably at the enzymatic optimum or within plus/minus 10° C. of the enzymatic optimum, until the desired conversion has taken place, possibly with shaking, preferably with shear-free stirring or shaking. The reaction is performed with a conversion of 50% (relative to racemate), possibly somewhat under this or more rarely above this, if this serves the higher optical purity of the target product (alcohol or ester). The preparation is performed with suitable organic solvents which are non-miscible with water (esters, ethers, aromatic compounds, even simple alkanes if the product is soluble), preferably ethyl acetate or toluene. In some cases, the extraction yield can be raised by the previous addition of small quantities of acetone or other solubilizers or by the previous removal of the enzyme by centrifugation. The preparation and purification follows the usual processes, which are also described above.

The enzymatically catalyzed separation of racemates by hydrolysis or esterification as described above is preferably performed in the temperature range of 10° C. to 70° C. In particular, lipase CAL-B has a temperature optimum of 60° C. and can be used at temperatures of up to 70° C. without problems. Another possible preferred temperature range for the procedures in accordance with the invention is e.g. 20° C.–45° C.

The enzymatic or temperature optima, in particular of the enzymes given above, are known to the person skilled in the art or can be determined by simple experiments.

In all the procedures in accordance with invention described above, it is of advantage if, between the respective synthetic steps or before use as synthetic building block, for example, in epothilone synthesis, diastereomeric separation is performed of compounds of the general formula I, II, III, IV and/or V, of which the α-hydroxy group is protected with a non-racemic chiral acyl group ($R^3$=R*). The separation of the diastereomers can for example be performed by crystallization, cocrystallization, distillation, sequential extraction, e.g., HSCCC (high speed counter current chromatography) and/or chromatographic separation, preferably by chromatographic separation, especially preferred being a liquid chromatographic procedure on achiral solid phases such as silica gel.

In a further preferred embodiment, compounds of the general formula IV are converted to compounds of the general formula V:

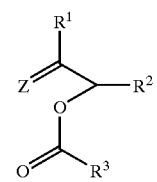

where Z is selected from the group consisting of: =O, =N-Nu, =CH-hetaryl, =CH-aryl and =PR$_3$; and is preferably =CH-hetaryl; and is especially preferably selected from the group consisting of (E)-(2-methylthiazol-4-yl)-CH= and (E)-(2-methyloxazol-4-yl)-CH=; where all groups Z may be present in the (E)-form, (Z)-form or as a (E/Z) mixture.

The conversion is performed preferably by reactions of the Wittig type, as known to the person skilled in the art. Conversion to a compound with the general formula:

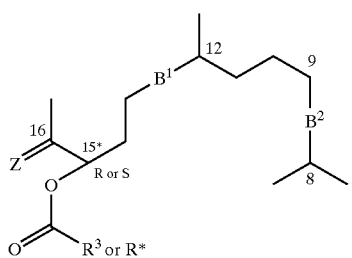

is particularly preferred.

In this manner, especially suitable building blocks for epothilone synthesis can be made available.

All the conversions described above can be performed on separated diastereomers and/or on a mixture of diastereomers.

All the above described synthetic building blocks and procedure steps can be used in the preparation of compounds with the general formula I, preferably in the non-racemic form on the α-hydroxy position.

In another alternative embodiment of the procedure according to the invention, the compounds of general formula I, II, IV and/or V are racemized under water-free and strongly basic conditions, preferably with the bases trialkylamine, DBU, DBN and/or polymeric strong bases. This enables a recirculation to carry out racemate separation.

For example, for this purpose free or protected acyloin is dissolved in a water-free organic solvent, preferably an alkane, ether and/or aromatic compound and base added. The temperature, preferably 0° C. to 65° C., especially preferably 25° C. to 40° C., can be raised to the boiling point of the solvent to increase the rate of isomerization, if this does not lead to marked side-reactions. After completion of the isomerization, the reaction mixture is filtered through silica gel or washed with acid or stirred with scavenger resin to remove the basic catalyst.

A further object of the present invention is the use of the compounds in accordance with the invention as building block, in particular as $C_{15}$–$C_{16}$ containing building block for the production of epothilones and their derivatives.

Finally, another object of the present invention is the use of the procedure according to the invention in the production of epothilones and their derivatives.

Synthetic building blocks prepared in accordance with the invention exhibit the general structural formula I, II, III, IV and V, preferably formulae I, IV or V with $R^1$=Me and $R^2$=A, and can be present in the racemic or non-racemic forms, as individual diastereomers or as a mixture of diastereomers. The structural elements with the general formulae I and V can preferably be used as products or as intermediates in the synthesis of active substances or drugs. Moreover, the structural elements with the general formulae I to V in accordance with the invention can be used for the synthesis of polyketide and terpenoid natural products, preferably, as with structural elements of the general formula V, for the synthesis of macrocyclic substances, such as epothilones and their derivatives, including stereoisomers and/or homologues, nor-compounds, and/or as fully or partially inverted elements, in which they can preferably serve as C15/C16 building blocks, as C12–C16 building blocks, as C11–C16 and C7–C16 building blocks or, especially preferably, as C7–C16(Me)-building blocks of the ring, which may additionally already contain preformed elements or the complete side chain C15 or C16 of the ring. The synthetic building blocks are preferably enriched in an enantiomeric and/or diastereomeric form, especially preferably in the absolute configuration corresponding to that of the natural epothilones. In addition, compounds in accordance with the general formulae I, IV and V are made available, in which the functional groups are fully or partially protected by PG.

The compounds in accordance with the invention with the general formulae I, II, III, IV and V may, in accordance with the invention, for example, be prepared in optically active form on C15 (or on C16 by the shift-acyloins) by asymmetric synthesis with alkoxyacetyl compounds coupled to Evans-type auxiliaries, by formation of diastereomers, followed by separation with optically active acids and their derivatives and by racemate separation by enzymatic hydrolysis or esterification; preferably with one of the latter two procedures; especially preferably with the enzymatic procedure.

The compounds in accordance with the invention with the general formulae I, II, III, IV and V generally contain at least one substituent in the lowest C-position which is suitable to make coupling with other building blocks of epothilone possible, e.g. on C7 especially with C1–C6 building blocks, as given in the German Patent Application DE 197 01 758.4.

In the context of the α-hydroxy compounds described as part of the present invention, and also possibly in connection with the further epothilone synthesis building blocks VII to XVI as described below in accordance with the invention, the residues in the previously given general formulae include the following substituents:

$R^1$: H, alkyl, aryl, alkylaryl ($CH_2$-aryl, $C_2H_4$-aryl etc.), vinyl, alkinyl, propargyl, allyl, 3,3-dialkylallyl, cycloalkyl (3–7 membered), $CH_nF_{3-n}$ (n=0–3), oxacycloalkyl (3–7 membered) and/or combinations of these, preferably H, methyl, ethyl, propyl, especially preferred methyl;

$R^2$: alkyl, aryl, alkylaryl ($CH_2$-aryl, $C_2H_4$-aryl etc.), vinyl, alkinyl, propargyl, allyl, alkylallyl, 3,3-dialkylallyl, E- or Z-3-halogenalkyl, 3,3-dihalogenallyl, cycloalkyl (3–7 membered), $CH_nF_{3-n}$ (n=0–3), oxacycloalkyl (3–7 membered) and/or combinations of these, preferably propargyl and alkylpropargyl, allyl and 3-alkylallyl and 3,3-dialkylallyl, E- or Z-3-halogenallyl, 3,3-dihalogenallyl, especially preferably allyl derivatives of type A (coupling at X):

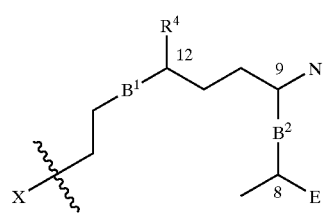

where $B^1$, $B^2$: Single or triple bond, double bond as E-(trans) form, Z-(cis) form or E/Z mixture; also epoxide or cyclopropane ring, as E-(trans) form, Z-(cis) form or E/Z mixture; preferably single and double bonds; especially preferred with $B^1$ as Z double bond or epoxide and with $B^2$ as single bond; and/or combinations thereof;

$R^4$: H, halogen (F, Cl, Br, I), alkyl, aryl, alkylaryl ($CH_2$-aryl, $C_2H_4$-aryl etc.), vinyl, cycloalkyl (3–7 membered), oxacycloalkyl (3–7 membered) and/or combinations thereof, preferably H, methyl, ethyl, $CH_nF_{3-n}$ (n=0–3), halogen, especially preferably H, methyl, ethyl, Cl; or combinations of these E: $CH_3$, $CH_2OH$, $CH_2OPG$, $CH=O$, $CO_2R$, $CO_2PG$, $CH_2X$, $CONR_2$, $CON(PG)_2CON(OMe)(Me)$, CN, preferably $CH_3$, $CH_2X$, $CO_2R$, $CO_2PG$, especially preferably $CH_2OH$, $CH_2OPG$, $CH=O$;

X: Coupling point (as part of the formula) or: H; OH; or halogen or other conventional leaving groups and their combinations; preferably Cl, Br, I, O-tosyl, methylsulfonate, trifluormethylsulfonate, alkanoate and arylcarboxylate; especially preferably H, Cl, Br;

Nu: $R^4$, O-PG, OR, $N(PG)_2$, N-alkyl$_2$, S-PG, S-alkyl, Se-PG, Se-alkyl, CN, $N_3$, aryl, heteroaryl, preferably $R^4$, O-PG, O-alkyl, $N(PG)_2$, N-alkyl$_2$, especially preferably H, alkyl;

$R^3$: alkyl, aryl, alkylaryl ($CH_2$-aryl, $C_2H_4$-aryl etc.), alkoxyalkyl, fluoroalkyl, preferably alkyl, benzyl, phenyl, especially preferably methyl, ethyl, propyl.

R*: chiral non-racemic residues, in particular of those optically active carboxylic acids and derivatives (esters, halides, anhydrides) R*—CO—X, which are commercially available or which are conventionally used for diastereomer formation, e.g. mandelic acid, O-protected mandelic acid, lactic acid, O-protected lactic acid, N-protected aminoacids, tartaric acid derivatives, camphoric acid etc., preferably α-chiral N-protected amino- and O-protected hydroxycarboxylic acids, especially preferably O-alkylmandelic acid, especially preferably with R*=CH(OMe)Ph;

Z: =O, =N-Nu, =CH-hetaryl, =CH-aryl, =$PR_3$; where all named double-bonded groups Z are present in the (E) form, (Z) form or as (E/Z) mixture, preferably =CH-hetaryl; especially preferably =O, (E)-(2-methylthiazol-4-yl)-CH=, (E)-(2-methyloxazol-4-yl)-CH=;

EWG: conventional electronegative functional groups such as $CO_2R$, $CO_2PG$, CN, CO—R, alkylphosphonate, $SO_2$—R, $SO_2OR$, preferably $CO_2R$, $CO_2PG$, especially preferably $CO_2$-t-Bu;

N-Aux*: conventional Evans type auxiliaries of oxazolidinone (Evans et al. *Pure & Appl. Chem.* 1981, 53, 1109–1127) or imidazolidinone type (Close, W. J. *J. Org. Chem.*, 1950, 15, 1131), derived from non-racemic aminoalcohols or diamines, commercially available or accessible from aminoacids, ephedrines etc. using procedures known from the literature, especially preferably from non-racemic imidazolidinones derived from ephedrines.

Alkyl designates hydrocarbon residues, also branched isomers, with preferably 1 to 8 carbon atoms.

Aryl designates phenyl, naphthyl, benzyl and their derivatives with up to five alkyl-, alkoxy- or halogen substituents, however preferably those with up to three substituents, especially preferably with up to one substituent; preferred are corresponding phenyl and benzyl derivatives; and combinations of these.

Hetaryl or heteroaryl designates five and six membered heteroaromatic compounds with one or several O, S, and N-atoms; and their derivatives with up to four alkyl, alkoxy or halogen substituents, however preferably those with up to two substituents, especially preferably with up to one substituent; preferred are corresponding oxazole, thiazole and pyrimidine derivatives; especially preferably alkylthiazole and oxazole derivatives; and combinations of these.

PG designates the conventional protective groups for the given coupling atom or the given functional groups, e.g. as in the book GREENE/WUTS 1991 (Protective Groups in Organic Synthesis, ISBN 0-471-62301-6), such as allyl, t-Butyl, methyl, benzyl, silyl, acyl or activated methylene derivatives such as methoxymethyl, alkoxyalkyl or 2-oxacycloalkyl protective groups; preferably—predominantly for alcohol and amine functions—trimethylsilyl, triethylsilyl, dimethyl-tertbutylsilyl, acetyl, propionyl, benzoyl, tetrahydropyranyl.

PG' are then those groups which do not react during the conventional enolization of the auxiliary-modified intermediates (e.g. with LDA), such as silyl, benzyl or oxymethyl derivatives in accordance with the above literature.

Act are the conventional activators of enzymatic acyl transfer. These are usually anhydrides or active esters such as alkenyl esters (Act=O-vinyl, O-isopropenyl etc.), trifluorethyl esters, oxime esters or thioesters, preferably alkenyl esters, especially preferably O-vinyl and O-isopropenyl.

A further essential aspect of the present invention relates to epothilone building blocks for the north and south moieties of epithilones and procedures for their production and coupling.

In particular, the compounds provided by the present invention are suitable as building blocks for the synthesis of polyketiden, terpenoids, epothilones and/or their derivatives. Examples for the epothilone synthesis building blocks in accordance with the invention are selected from the group consisting of compounds with the general formulae VII, X, Xa, XI, XIa, XII, XIII, XVa and XVb.

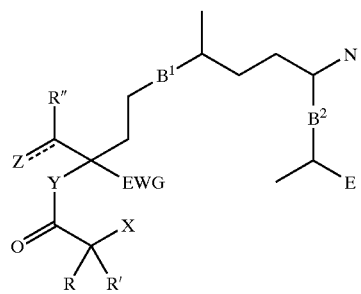

VII

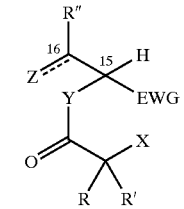

X

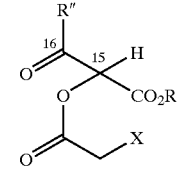

Xa

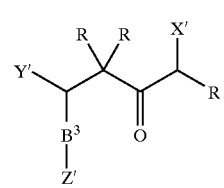

XI

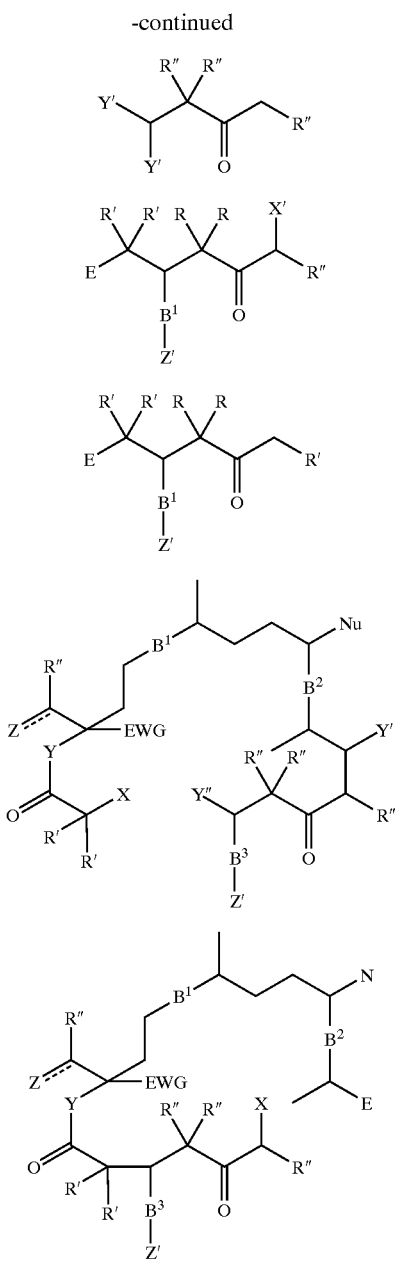

where
- B¹, B², B³ are selected from the group consisting of single bonds; double bonds as E-(trans) form, Z-(cis) form or E/Z mixture; epoxide rings as E-(trans) form, Z-(cis) form or E/Z mixture; and cyclopropane rings as E-(trans) form, Z-(cis) form or E/Z mixture; and/or combinations thereof; preferably selected from the group consisting of single and double bonds; and especially preferably where B¹ is a Z double bond or an epoxide and B² and B³ are single bonds;
- R is selected from the group consisting of H; alkyl; aryl; alkylaryl such as $CH_2$-aryl, $C_2H_4$-aryl and similar; vinyl; cycloalkyl, in particular a 3- to 7-membered cycloalkyl; $CH_nF_{3-n}$ (n=0–3); oxacycloalkyl, particularly a 3- to 7-membered oxacycloalkyl and/or combinations thereof; preferential selections are from the group consisting of H, methyl, ethyl, phenyl and benzyl; and H, methyl, ethyl and/or combinations thereof are especially preferred;
- R' is selected from the same group as R, and H is especially preferred;
- R" is selected from the same group as R, and methyl is especially preferred;
- E is selected from the group consisting of $CH_3$, $CH_2OH$, $CH_2OPG$, CH=O, $CO_2R$, $CO_2PG$, $CH_2X$, $CONR_2$, $CON(PG)_2$, CON(OMe)(Me) and CN; preferably selected from the group consisting of $CH_3$, $CH_2X$, $CO_2R$, and $CO_2PG$; and especially preferably selected from a group consisting of $CH_2OH$, $CH_2OPG$ and CH=O;
- X is selected from a group consisting of H; OH; halogen; other conventional leaving groups and/or their combinations; preferably selected from the group consisting of Cl, Br, I, O-tosyl, methylsulfonate, trifluormethylsulfonate, alkanoates and arylcarboxylates; and especially preferably selected from the group consisting of H, Cl and Br;
- X' is selected from the group consisting of OH; halogen, other conventional leaving groups and/or their combinations; preferably selected from the group consisting of Cl, Br, I, O-tosyl, methylsulfonate, trifluormethylsulfonate, alkanoates and arylcarboxylates, and is especially preferably Cl and/or Br;
- Y is selected from the group consisting of S, NH, N-PG, NR, O; and preferably selected from the group consisting of NH, N-PG, NR and O; and is especially preferably O;
- Y' is selected from a group consisting of H, OH, OR, O-PG, $NH_2$, $NR_2$, $N(PG)_2$, SR and SH; and is preferably O-PG and/or OR;
- Y" is selected from the group consisting of H, OH, OR, O-PG, $NH_2$, $NR_2$, $N(PG)_2$, SR, SH, Cl, Br and $CR'_2$-EWG; is preferably O-PG and/or OR; and is especially preferably H, $CH_2CO_2R$ and/or $CH_2COR^*$;
- Z is selected from the group consisting of —OH, —O-PG, —OR, =O, =N-Nu, =CH-hetaryl, =CH-aryl and =$PR_3$; where all the above double bonded groups Z may be present as the (E) form, (Z) form or as (E/Z) mixtures and where the group is preferably =CH-hetaryl; and is especially preferably selected from the group consisting of =O, (E)-(2-methylthiazol-4-yl)-CH= and (E)-(2-methyloxazol-4-yl)-CH=;
- Z' is selected from the group consisting of O, OH, OR, O-PG, $N(H)_{1-2}$, $N(R)_{1-2}$, $N(PG)_{1-2}$, SR, S-PG and R; is preferably O, O-PG and/or OR;
- Nu is selected from the group consisting of R, O-PG, OR, $N(PG)_2$, $NR_2$, S-PG, SR, SeR, CN, $N_3$, aryl and heteroaryl; is preferably selected from the group consisting of R, O-PG, OR, $N(PG)_2$ and $NR_2$; and is especially preferably H and/or alkyl;
- EWG is selected from the group consisting of E, CN, CO—R, dialkylphosphonate, $SO_2$—R, $SO_2OR$, $CF_3$, $CCl_3$ and $NO_2$; is preferably selected from the group consisting of CN, CO—R and CO—$NR_2$; and is especially preferably $CO_2R$, $CO_2PG$, where PG is preferentially tert-butyl;
- Alkyl is selected from hydrocarbons, including branched isomers, for example with $C_{1-20}$ and preferably with 1 to 8 carbon atoms.
- Aryl is selected from the group consisting of phenyl, naphthyl, benzyl and their derivatives; preferably with up to five alkyl, alkoxy or halogen substituents, especially preferred being those with up to three substituents, and most preferred being those with up to one substituent; and preferably selected from the group consisting of phenyl and benzyl derivatives and combinations of these.

Hetaryl/heteroaryl is selected from the group consisting of five and six membered heteroaromatic compounds with one or several O-, S- and N-atoms; and their derivatives with up to four alkyl, alkoxy and/or halogen substituents; preferably those with up to two substituents, especially preferably with up to one substituent; preferably selected from the group consisting of oxazole, thiazole and pyrimidine derivatives; and where an alkylthiazole derivative is specially preferred; and combinations of these.

PG is a protecting group, preferably selected from the group consisting of allyl, methyl, t-Butyl (preferably at EWG), benzyl, silyl, acyl and activated methylene derivatives such as methoxymethyl, alkoxyalkyl and 2-oxacycloalkyl; preferably—predominantly for alcohol and amine functions—selected from the group consisting of trimethylsilyl, triethylsilyl, dimethyl-tertbutylsilyl, acetyl, propionyl, benzoyl, tetrahydropyranyl; and from protecting groups which protect neighbouring or bivalent groups ($PG_2$) simultaneously by forming 5–7 membered rings, such as succinyl, phthalyl, methylene, acetonide and/or combinations of all the above protecting groups.

E is preferably $CH_2X$, $CO_2PG$ and/or CHO and especially preferably CHO.

In addition, it is preferred that EWG=H; and X H and/or halogen. It is particularly preferred that EWG is selected from the group consisting of Cl, Br and I.

In addition, it is preferred that the substituent Y—CO—CRR'X is replaced by an OH— or $NH_2$— group, preferably by OH.

In the compounds with the general formula X, in particular with those with the general formula Xa, R=tert-butyl and X=H, Cl and/or Br.

The preferred embodiments for compounds with the general formula XI and/or XIa are those in which $B^3$ is a single or double bond as E-(trans) form, Z-(cis) form or a E/Z mixture; preferably a single or double bond to heteroatoms such as O, S or N, especially preferably a single bond to O-PG or OH; R is selected from a group consisting of H, methyl, ethyl, propyl, phenyl, benzyl; preferably selected from a group consisting of H, methyl, ethyl and combinations of these; R" is selected from the same group as R and methyl is particularly preferred.

The preferred embodiments for compounds with the general formula XII and/or with the general formula XIII are those in which $B^1$ is selected from the group consisting of single bonds, double bonds in the E-(trans) form, Z-(cis) form or as a E/Z mixture;

R is selected from the group consisting of H; alkyl; aryl; alkylaryl such as $CH_2$-aryl, $C_2H_4$-aryl and similar groups; vinyl; cycloalkyl, in particular a 3- to 7-membered cycloalkyl; $CH_nF_{3-n}$ with n=0 to 3; oxacycloalkyl, in particular a 3- to 7-membered oxacycloalkyl; and/or combinations of these; and is preferably selected from the group consisting of H, methyl, ethyl, phenyl and benzyl; and is especially preferably selected from the group consisting of H, methyl, ethyl and combinations of these;

R' is selected from the same group as R and is especially preferably H;

R" is selected from the same group as R and is especially preferably methyl;

X' is selected from the group consisting of OH; halogen; other conventional leaving groups and/or their combinations; and is preferably selected from the group consisting of Cl, Br, I, O-tosyl, methylsulfonate, trifluormethylsulfonate, alkanoates and arylcarboxylates; and is especially preferably selected from the group consisting of H, Cl and Br;

Z' is selected from the group consisting of O, OH, OR, O-PG, $N(H)_{1-2}$, $N(R)_{1-2}$, $N(PG)_{1-2}$, SR, S-PG and R; and is preferably O, O-PG and/or OR;

E is selected from the group consisting of $CH_2OH$, $CH_2OPG$, $CH_2OR$, CH=O, CR=O, $CH(OR)_2$, $CH(OPG)_2$, CH=NPG and combinations of these; and is preferably selected from the group consisting of COEt, $CO_2R$, COR* and $CH(OPG)_2$; and is especially preferably selected from the group consisting of $CO_2R$, $CO_2PG$, $CO_2H$ and COR;

R* is selected from the group consisting of chiral residues and auxiliaries and, for acyl derivatives such as esters, amides and imides, is preferably selected from the group consisting of 1-alkylbenzylamino; 1-alkylbenzyloxy; lactate and mandelate derivatives; monoterpene derivatives, e.g. Oppolzer sultam, 8-arylmenthyloxy and the like; and N-bound oxazolidinones (Evans type auxiliaries); and is especially preferably selected from the group consisting of 4-substituted oxazolidinones; each as pure enantiomers, enantiomerically enriched, racemic form, and/or as mixtures; alkyl stands for hydrocarbons, also branched isomers, preferably for $C_{1-20}$, and especially preferably for 1 to 8 carbon atoms;

aryl is selected from the group consisting of phenyl, naphthyl, benzyl and their derivatives, preferably with up to five alkyl, alkoxy and/or halogen substituents, especially preferably with up to three substituents, most preferably with up to one substituent; and is preferably selected from the group consisting of corresponding phenyl and benzyl derivatives and combinations of these;

PG is a protecting group and is preferably selected from the group consisting of allyl, methyl, t-butyl (preferred for EWG), benzyl, silyl, acyl and activated methylene derivatives such as methoxymethyl, alkoxyalkyl and 2-oxacycloalkyl protecting groups; and is preferably selected—predominantly for alcohol and amine functions—from the group consisting of trimethylsilyl, triethylsilyl, dimethyl-tert-butylsilyl, acetyl, propionyl, benzoyl, tetrahydropyranyl; and from protecting groups which simultaneously protect neighbouring or bivalent groups ($PG_2$) with formation of 5–7 membered rings, such as succinyl, phthalyl, methylene, acetonide; and/or combinations of all the above protecting groups;

especially preferred are X'=Cl and/or Br; R'=H; R=Me; E=$CO_2R$, $CO_2PG$, $CO_2H$ and/or COR; and/or B'-Z'=O-PG.

Preferred embodiments for compounds with the general formula of XVa and/or XVb are those in which $B^3$ is a single bond or a double bond as E-(trans) form, Z-(cis) form or E/Z mixture; preferably a single or double bond to heteroatoms such as O, S, N; especially preferably a single bond to O-PG or a double bond to O; EWG with X≠H is especially preferably H; with being especially preferred X≠H; EWG=H; Z=O, (E)-(2-methylthiazol-4-yl)-CH= and/or (E)-(2-methyloxazol-4-yl)-CH=; R'=H; R"=Me; and/or Y"=$CH_2COOH$, OH; Y', Z'=O-PG and/or OH.

In the following, particular embodiments of the synthetic building blocks for the north and south moieties of epothilones are described.

The North Moiety:

It was surprisingly found that natural, commercial or prenyl derivatives known from the literature, in particular geranyl, neryl, linaloyl and farnesyl derivatives with the general formulae VIII and IX, preferably starting with their alcohols, acetates or halides, can be converted into electrophilic synthetic building blocks of type VIII for epothilones and their derivatives or can be used as such, to be coupled by simple nucleophilic substitution with a C15–C16 structural element with the general formula X—preferably of the acetoacetate type, especially preferred with the formula Xa—which already has the correct oxidation state or substitution Y at C15.

The term derivatives includes homologous, analogous and nor-compounds, preferably also variants with further substituents on the main chain or in the C15–C16 element. Depending on the starting material, no further C—C coupling is necessary for the region C7–C10 and/or C11–C14 (a prenyl unit), in particular however for C7–C14 (two prenyl units, e.g. from nerol, geraniol and linalool, Y=OH). The stereochemistry of the starting material (E- or Z-prenyl compound) can be used to predetermine the stereochemistry on C12–C13.

Specific examples for compounds with the general formula VII are given below.

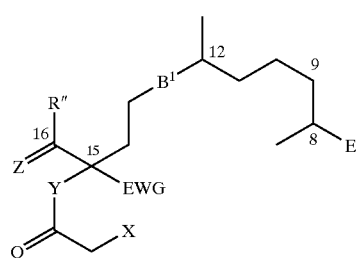
VIIa

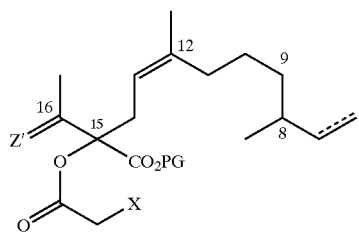
VIIb

In compounds VIIb Z' is preferably =O, 2-methylthiazol-4-ylmethylene, 2-methyloxazol-4-ylmethylene, X=Cl, Br; and especially preferably H; PG=t-Bu.

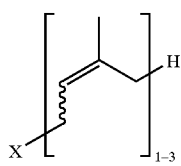
VIII

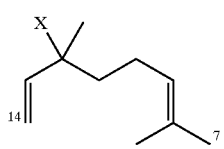
IX

In the compounds VIII and IX, X is preferably OH, OAc, OTs, Cl and/or Br. OTs, Cl, Br are especially preferably used as electrophilic building blocks.

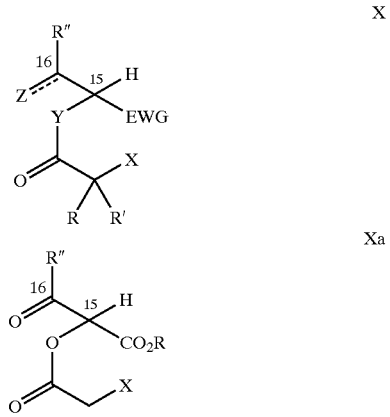
X

Xa

In the C15–C16 building block with formula IV, it is especially preferred that X=H, R=t-Bu and/or R"=Me.

Synthetic building blocks prepared according to the invention have, among other characteristics, the general structural formula VII, preferably the formula VIIa, especially preferably the formula VIIb, and may be present in the racemic or non-racemic forms, or as individual diastereomers or as a mixture of diastereomers.

The structural elements VII and X can be preferably used as products or as intermediates in the synthesis of active substances. Moreover, the structural elements VII in accordance with the invention can be used for the synthesis of polyketide and terpenoid natural products or derivatives of polyketide and terpenoid natural products, preferably for macrocyclic active substances such as epothilones and their derivatives, including stereoisomers and/or homologues, nor-compounds, and/or can serve as fully or partially inverted elements, in which they serve preferably as C7–C15 and C7–C16 or especially preferably as C7–C14 structural elements of the ring, which additionally may already bear preformed elements or the complete side chain on C15.

These building blocks are referred to below as synthetic building blocks and are preferably enriched in an enantiomeric and/or diastereomeric form, the forms which correspond to those in the natural epothilones.

Moreover, the compounds in accordance with the invention with the general structural formula VII and X are provided, in which the functional groups are totally or partially protected by PG.

The compounds of type VII in accordance with the invention and their stereoisomers can be obtained for example starting with commercially available starting materials VIII and/or IX, which may also be prepared by known procedures, by C—C coupling with 2-oxy-substituted 1,3-diactivated methylene compounds with the general formula X, preferably with 2-acyloxy-1,3-dicarbonyl compounds, especially preferably with 2-acyloxyacetoacetates, specifically preferably with compounds of formula Xa, where basic reaction conditions are of particular advantage.

Moreover, it has been found that modifications on C7, C8 and C9 of the above named compounds may be performed, especially by oxidation, for example on C7; reduction of for example C8–9; nucleophilic addition on for example C9 with E=EWG; substitution, for example on C7; modifications on C12–13, for example epoxidation; modifications on C16, for example alkenylation, e.g. Wittig type reaction with Z=O; modifications on C15 such as removal of EWG, for example decarboxylation; and/or transesterification or saponification/esterification of Y.

The above mentioned substituents, protecting groups, bond types B and/or stereoisomers and the sequence of the coupling or modification can be altered and combined as desired, in so far as it is chemically reasonable.

The compounds according to the invention of type VII, but also of type VII with EWG=H, usually exhibit at least one substituent in positions 7, 15 and/or 16 which is not hydrogen or R and are preferably those substituents which are suitable to bring about coupling to C17–C20 side chain building blocks and especially with C1–C6 building blocks or their starting materials, as for example is described in German Patent Application 197 01 758.4, especially preferred by ester or lactone formation of an epothilone C1 building block with C15 and/or aldol or Reformatsky type reaction on an epithilone C6 building block with C7 and/or coupling of a C17–C20 side chain building block with C16, in so far as the latter has not already been coupled in an earlier step.

Compounds of the structural element of the type I with E=$CH_2OH$, CHO, $CO_2R$ may be produced in that, for example, compounds VII, preferably VIIa, especially preferably neryl derivatives, are oxidized, preferably in the 7-position. In addition, sensitive positions which are not to be oxidized, can be protected in the conventional and well known manner (see below). Thus, alcohols are preferably protected as silyl ethers or alkanoates and carboxylic acid groups preferably as esters. The oxidation is carried out according to the instructions, as they are listed for example in HUDLICKY 1990 (Oxidations in Organic Chemistry, 0-8412-1781-5/90). The 7 position is preferably oxidized, preferably with selenium reagents, especially preferably with selenium dioxide or peroxides.

In this connection and in the context of the invention it was found that first alcohols (E=$CH_2OH$) or aldehydes (E=CHO) were formed, depending on procedure and the quantity of selenium dioxide used.

Further oxidation of the alcohols to the aldehyde, preferably with activated DMSO, but also reduction and substitution according to conventional procedures, make further substituents E accessible. Further oxidation of the aldehydes, e.g. with $NaClO_2$ or air/catalyst, gives carboxylic acids.

The allylalcohols from commercial prenylalcohols or prepared as above can be converted into an active form according to known procedures, preferably into allylhalides, -sulfonates or carboxylates, especially preferably into C7- and C14-halides of the compounds VII or VIII and protected derivatives of these.

Further modifications can be carried out on the double bonds. Thus conversion can be carried out into single bonds, epoxides and cyclopropanes, using procedures known from the literature. Reduction is carried out according to known procedures, preferably using hydride donors and especially preferably catalytical procedures; asymmetric procedures are also used. Differentiation of the double bonds, in so far as this is not already present as a result of the substitution pattern of the starting materials, can be made electronically, e.g., with suitably selected neighbouring protective groups (electronegative or electropositive) or, preferably sterically, e.g. through the selection of a suitable sequence of the prenyl modifications as described above.

In particular, it was found that with suitable groups EWG, in particular tert-butylcarboxylates ($CO_2$t-Bu), in particular the C8–C9 double bond can be selectively reduced. A remaining C12–C13 double bond can, for example, be selectively epoxidated with peroxyacids. If the C8–C9 double bond is electronegatively substituted (E=oxomethylderivatives, preferably $CO_2R$, CHO), nucleophiles may be selectively introduced into position 9 with the Michael reaction, where simple alkyl cuprates, alcohols and amines are preferred.

The reductions, nucleophilic additions, epoxidations and cyclopropanations of the double bonds, or combinations of these, can be performed on suitably protected prenyl derivatives VII in accordance with procedures known from the literature. In so far as it is chemically reasonable, some of these modifications can be carried out on C1–C6 building block which is coupled singly or doubly to compounds of formula I (also with EWG=H). Epoxidation of the C12–C13 double bond is preferred.

Moreover, it was found that in accordance with the invention compounds of type VII, preferably VIIa, may be transformed into compounds of type VII with EWG=H. Especially preferably, compounds of formula VII are used, with PG=t-Butyl, specifically those of formula VIIb, which are decarboxylated in a single acid catalysed step to the corresponding compounds VII with EWG=H. These compounds can also be coupled with C1–C6 building blocks.

In the procedure according to the invention for the above named compounds, it is preferred that functional groups of the compounds of type VII-X, preferably of type VIIa, and of intermediates, are converted in their protected form (M=PG). Suitable protecting groups are: allyl, benzyl, methyl, ethyl, t-butyl, activated methylene derivatives such as methoxymethyl, 1-oxacycloalkyl, silyl, in particular trialkylsilyl; and—predominantly for alcohol functions—also acyl protecting groups, preferably acetyl, propionyl and benzoyl and their derivatives. Protecting groups are also preferred which simultaneously protect neighbouring groups Y, for example acetonides, methylene, cyclodiacyl and those which protect carbonyl groups, in particular acetals and cyclic acetals (O and S). Other protecting groups which are suitable for the procedure in accordance with the invention are described in GREENE/WUTS 1991 (Protective Groups in Organic Synthesis), which is expressly referred to. Combinations of these protecting groups are also possible and advantageous, depending on the approach.

The South Moiety

For the synthesis of the south moiety of epothilones in accordance with the invention, compounds of the types XII and XIII may be used.

In accordance with the invention, it was found that compounds of type XI are also suitable C3–C6 building blocks and that these can for example be prepared by reaction of 2-haloacylhalides with the enamine of isobutyraldehyde, followed by hydrolysis and acetal formation.

In accordance with the invention, it was also found that compounds of the type XII or XIII activated in the C6 position may easily be obtained from compounds of type XIII and XIa by oxidation, especially by electrophilic halogenation, especially preferably with tertiary or quaternary ammonium perhalides. These reactions are very easy and give good yields.

In accordance with the invention it was also found that the above named compounds XI to XIII can be efficiently coupled to C7 etc. building blocks, e.g. of the type VII, which is preferably mediated by low valent metal ions or metals in Reformatsky type reactions, as for example is explained in German Patent Application No. 197 01 758.4.

It was also found in accordance with the invention that the reaction, i.e. the reaction with compounds of the general formula VII, occurs to an extraordinarily high degree with syn-selectivity and aldehyde-selective, which makes it possible to react substances of type VII in an efficient manner, especially those in which Z is a ketone or a hetarylalkylidene side chain. A particular advantage of the procedure in accordance with the invention is that the functionalities may be used without protection to a large extent. Thus, for example, a free ester group may be used at C1 and a free keto group at C16.

Coupling of North and South Moiety

A significant aspect of the present invention relates to the coupling of north and south moieties. Particularly, it was found that north and south moieties may be coupled, or—in case of preesterized components—be cyclicized by aldole reactions, preferably of the Reformatsy type, especially preferred with chromium(II) salts, between C6–C7 or C2–C3, or successively on both sites, using the previously described methods which are described in the following and in detail particularly in the examples.

This entirely new method allows cyclization with high syn-selectivity and chemoselectivity. Open chain compounds may be cyclicized by macrolactonization according to known methods.

Modifications and substitution may be achieved in various steps during the synthesis of the components and during macrocyclene synthesis. For example it was found that modifications can be made at C7, C8, and C9 of the previously described building blocks, and at suitable intermediate compounds on the way to the macrocycle, particularly by oxidation, preferably at C7; reduction, preferably at C8–9; nucleophile addition, preferably at C9 with E=EWG; substitution, preferably at C7, modifications at C12–13, preferably epoxidation; modifications at C16, preferably alkenylation, particularly preferred reactions of the Wittig type with Z=O; modifications at C15, preferably removal of EWG, particularly preferred by decarboxylation; as well as transesterification or saponification/esterification of Y. The previously named substituents, protecting groups, bond types B and/or stereo isomers, as well as the order of coupling or modification may be changed or combined arbitrarily, if chemically reasonable.

In the following, a number of preferred embodiments of methods according to the invention are described for the synthesis of synthesis components VII to XVI according to the invention.

In one embodiment of the methods according to the invention, the compounds with the general formulae VII, VIII, X and/or XI are racemized under anhydrous, strongly alkaline conditions, preferably with the bases trialkylamine, DBU, DBN, and/or polymeric strong bases.

A further embodiment of the methods according to the invention for the production of compounds according to the formula VII comprises the reaction of prenylene compounds, electrophilically activated in α and/or ω position, composed of 1–4 prenyl units with compounds according to the general formula X.

The prenylene compounds, electrophilically activated in α and/or ω position, are selected from the group consisting of prenyl alcohols, acetates, halides, compounds with the general formula VIII, compounds with the general formula IX, and functionalized and/or protected prenyl derivatives with the general formula XIV,

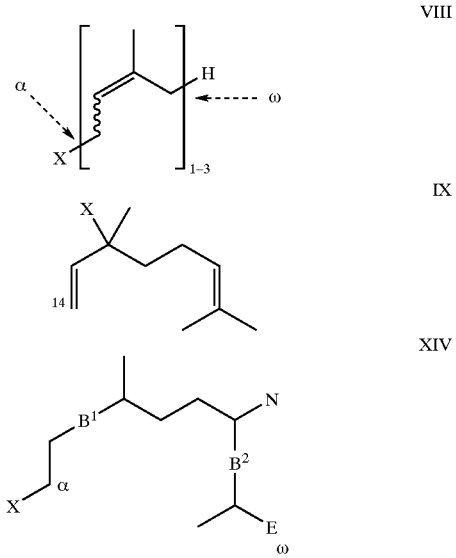

where
B¹, B² are selected from the group consisting of single and double bonds in the E(trans) form, Z(cis) form or E/Z mixture; epoxide rings in the E(trans) form, Z(cis) form or E/Z mixture; cyclopropan rings, in the E(trans) form, Z(cis) form or E/Z mixture; and/or combinations thereof; being preferably selected from the group consisting of single and double bonds; and B¹ particularly preferably being a Z double bond or an epoxide, and B² being a single bond;

E is selected from the group consisting of $CH_3$, $CH_2OH$, $CH_2OPG$, CH=O, $CO_2R$, $CO_2PG$, $CH_2X$, $CONR_2$, $CON(PG)_2$, CON(OMe)(Me) and CN; being preferably selected from the group consisting of $CH_3$, $CH_2X$, $CO_2R$ und $CO_2PG$; and being particularly preferably selected from the group consisting of $CH_2OH$, $CH_2OPG$ und CH=O;

X is selected from the group consisting of H; OH; halogen; other usual reduction groups and their combinations; being preferably selected from the group consisting of Cl, Br, I, O-tosyl, methyl sulfonate, trifluormethyl sulfonate, alkanoates and arylcarboxylates; and being particularly preferably selected from the group consisting of H, Cl and Br;

Nu is selected from the group consisting of R, O-PG, OR, $N(PG)_2$, $NR_2$, S-PG, SR, SeR, CN, $N_3$, aryl and heteroaryl; being preferably selected from the group consisting of R, O-PG, OR, $N(PG)_2$ and $NR_2$; and being particularly preferably selected from the group consisting of H and alkyl;

R is selected from the group consisting of H; alkyl; aryl; alkyl-aryl such as $CH_2$-aryl, $C_2H_4$-aryl, and the like; vinyl, cycloalkyl; particularly a 3- to 7-membered cycloalkyl; $CH_nF_{3-n}$ (n=0–3); oxacycloalkyl; particularly a 3- to 7-membered oxacycloalkyl; and combinations therefrom; being preferably selected from the groups consisting of H, methyl, ethyl, phenyl, and benzyl; and being particularly preferably selected from the group consisting of H, methyl, ethyl, and combinations thereof;

Alkyl is selected from hydrocarbons, also from branched isomers, for example with $C_{1-20}$ and preferably with 1 to 8 carbons;

Aryl is selected from the group consisting of phenyl, naphtyl, benzyl, and their derivatives; preferably with up to five alkyl, alkoxy or halogen substituents, particularly preferred being those with up to three substituents, most of all preferred being those with up to one substituent; and being preferably selected from the group consisting of phenyl and benzyl derivatives, and combinations thereof;

PG is a protecting group, being preferably selected from the group consisting of allyl, methyl, t-butyl (preferably for EWG), benzyl, silyl, acyl, and activated methylene derivatives such as methoxymethyl, alkoxyalkyl, or 2-oxacycloalkyl; preferably—mostly for alcohol and amin functions—being selected from the group consisting of trimethylsilyl, triethylsilyl, dimethyl-tert-butylsilyl, acetyl, propionyl, benzoyl, tetrahydropyranyl; as well as from protecting groups, which protect neighbouring or bivalent groups ($PG_2$) concomitantly by forming 5–7-membered rings, such as succinyl, phthalyl, methylene, acetonide; and/or combinations of all previously listed protecting groups;

where it is particularly preferred that $B^1$ is a double bond; that Nu is H; that E is selected from the group consisting of $CH_2OH$, CHO, and $CO_2R$; and/or X is selected from the groups consisting of Cl, Br and OTs.

Particularly, the prenyl compounds, preferably the compounds with formula VIII, IX, and/or XIV, are converted by C—C coupling using nucleophilic substitution with 2-oxy-substituted, 1,3-di-activated methylene compounds according to the formula X, preferably 2-acyloxy-1,3-dicarbonyl compounds, particularly preferred with 2-acyloxy-acetoacetates, most of all preferred with compounds according to formula Xa, preferably in presence of one or more bases, adding a solvent where applicable, and/or in the presence of modifiers.

The reaction temperature usually ranges from −80° C. to +180° C., preferably from −30° C. to +100° C., and particularly preferred from −5° C. to +80° C.

Suitable bases are usually selected from the group comprising alkali metals, hydridic bases, nitrogen bases in neutral or negatively charged form, alcoholates, hydroxides, carbonates, hydrogencarbonates, and carban ions; preferably comprising hydridic bases, nitrogen bases, carbonates, hydrogencarbonates, and particularly preferred comprising hydridic bases, carbonates, and/or hydroxides of the alkali or alkali earth metals, such as NaH, KH, and LiH.

Suitable solvents are selected for example from the group comprising hydrocarbons, alkanes, benzene, and alkylized derivatives therefrom, ether, dichlormethane, chloroform, tetrachlorcarbon, chlorated aromates, alcohols, ketones, sulfoxides such as DMSO and sulfolane, carbon acid amids, alkylated carbon acid amids, sulfolane, DMPU, glymes, alkyl and aryl nitrites, carbon acid esters, tertiary amines and/or mixtures thereof, preferably comprising carbon acid amids and alkylated carbon acid amids, ketones, sulfoxides such as DMSO, and sulfolane, alcohols, alkyl and/or aryl nitrites; and particularly preferred comprising carbon acid amids, alkylated carbon acid amids, ketones, sulfoxide, DMSO, sulfolane and/or alcohols.

A further subject of the present invention are methods for synthesizing compounds with the general formula VII with EWG=H. Such methods comprise alkyl decarboxylation or saponification/decarboxylation of compounds with the general formula VII with EWG=$CO_2R$ or $CO_2PG$, preferably according to the Krapcho method, more preferably in presence of LiCl and DMSO, for example at increased temperatures, and particularly preferred starting from compounds with the general formula VII with EWG=$CO_2tBu$ in the presence of suitably strong acids, preferably volatile and anhydrous acids, particularly preferred in presence of trifluor acetic acid.

A further subject of the present invention are methods for synthesizing compounds with the general formula XI. Such methods comprise reacting a compound with the general formula XI with X'=H with a reagent selected from the group consisting of halogenization reagents, and electrophilic oxygen reagents in a suitable solvent, if applicable adding acidic or alkaline modifiers.

Preferably, a compound with the general formula XIa with Y'=OMe is used as compound with the general formula XI.

A further subject of the present invention are methods for synthesizing compounds with the general formula XII. Such methods comprise reacting a compound with the general formula XIII with a reagent selected from the group consisting of halogenization reagents, and electrophilic oxygen reagents in a suitable solvent, if applicable adding acidic or alkaline modifiers.

Suitable halogenization reagents are for example electrophilic halogenization reagents, preferably selected from the group consisting of primary halogens; halogenimide derivatives; sulfur(oxy)halides such as sulfurylchloride; perhaloalkanes, and ammonium perhalides; and particularly preferred being selected from the group consisting of tertiary and quarternary ammonium perhalides such as pyridinium bromide perbromide, trimethyl phenyl ammonium bromide perbromide, and/or polymer-bound variants of the previously mentioned reagents.

The reaction temperature in the latter mentioned method is usually from −80 to +160° C.; preferably from −30 to +65° C.; and particularly preferred from −5 to +10° C.

Suitable solvents are usually selected from the group consisting of etheric and halogenized solvents; being preferably selected from the group consisting of diethylether, THF, chloroform, dichlormethane, liquid carbon acid amids and esters; and being preferably selected from the group consisting of DMF, DMA, acidic acid ester, liquid sulfoxides such as DMSO and sulfolane.

A further subject of the present invention are methods for synthesizing compounds with the general formulae XVa and/or XVb. Such methods comprise reacting compounds VII with compounds of type XI or XIa; XII; and/or XIII. Preferred are such compounds XV in which all carbon atoms of the epothilone macrocycle XVI are present. Particularly preferred are such compounds XV in which the following bonds are still open: C2–3 as in XVa; O15-C1 as e.g. in XVa with Y—CO—CR'$_2$X=OH or Y"=$CH_2CO_2H$; and/or C6–7 as in XVb. Most preferred are such compounds XV bearing a halogen at C2 and/or C6.

A further subject of the present invention are methods for synthesizing compounds with the general formula XVa, comprising the generation of a C6–C7-coupling by reacting compounds with the formula VII with compounds with the general formulas XI, XII and/or XIII; preferably with compounds of the general formulas XI and/or XII with X'=Cl, Br or I; in presence of bases and/or in presence of one or more metals and/or metal salts; if applicable adding solvents, catalysts, and/or modifiers.

In these methods, the reaction temperature ranges usually from −80° C. to +140° C.; being preferably higher than 0° to 65° C., and particularly preferred being from 15° C. to 35° C.

Suitable metals are usually selected from the group consisting of Li, Mg, Zn, In, Mn, Fe (each in activated form); and suitable metal salts, preferably anorganic or organic salts; complexes and/or organometal complexes of the metal ions Ti(II), Ti(III), Cr(II), Sm(II), Co(I), V(II) and Fe(II), particularly preferably halides, sulfates, sulfonates, alkanoates, cyclopentadienylates and phenylates; solid phase or polymer-bound metal salts; and combinations therefrom; and preferably selected from the group consisting of zinc, titanium(II) and Cr(II) compounds, particularly as chloride, bromide, acetate, sulfate, generated in situ or polymer-bound.

Suitable catalysts are selected from the group consisting of iodides; unreducable Lewis acids, such as lithium salts, aluminum chloride, boron trifluoride, and/or Lewis acids generated in situ during the formation of reducing metal salts with $LiAlH_4$; nickel(II) salts; nucleophilic and/or redoxactive metal complexes, such as vitamin B12 and comparable, synthetic Co complexes. Furthermore, the suitable catalysts are present preferably in amidic solvents and/or sulfolane; and it is also preferred that up to 33 mol % of the anhydrous catalyst, preferably 0.01–5 mol % reactive Lewis acids, is added, if applicable mixed with a suitable metal salt, preferably prior to the addition of the solvent.

The modifiers are preferably selected from the group consisting of iodides (metal iodides MI); unreducable, usual Lewis acids such as lithium salts; aluminium chloride, boron trifluoride, complexing ligands, particularly also chiral ligands, particularly preferred bidentate ligands and other usual ligands; and combinations therefrom; and are preferably also in an anhydrous condition. Particularly preferred are modifiers from the group consisting of anhydrous lithium oxide, sodium iodide and aluminium chloride.

Suitable solvents are usually selected from the group consisting of hydrocarbons such as alkanes, benzene, and alkylated derivatives; ethers; dichlormethane; chloroform; chlorated aromates; sec./tert. alcohols; ketones; dimethylsulfoxide; carbon acid amids; alkylated carbon acid amids, sulfolane; DMPU; glymes; alkyl and aryl nitriles; carbon acid esters; tertiary amines and mixtures thereof; and are preferably selected from the group consisting of methyl-tert.-butylether, diethylether, tetrahydrofurane, glymes, sulfolane, DMSO, ketones up to C5, dimethylformamide and -acetamide, acetonitrile and mixtures thereof; and should particularly preferably be anhydrous solvents.

The methods according to the invention preferably comprise reacting one or more metal salts by reduction with a reducing agent at an oxidation level suitable for the method; the reaction being performed preferably in situ, or prior to the synthesis of the compound with the general formula XVa.

Suitable reducing agents or methods are, for example, selected from the group consisting of electrochemical methods, lithiumaluminiumhydrid, and comparable hydrids, metalic iron or manganese in their various forms, and are preferably selected from the group consisting of lithiumaluminiumhydrid and zinc.

A further subject of the present invention relates to methods for synthesis of a compound with the general formula XVb, comprising the formation of a O15–C1 bond by reacting compounds with the general formula VII with compounds with the formula XII or XIII, particularly preferred XII with X'=Cl, Br or I, in presence of esterification, transesterification and/or coupling reagents, if applicable adding solvents.

The reaction temperature of this method according to the invention usually ranges from −50° C. to +160° C., preferably over 0° to 100° C., and particularly preferred from 15° C. to 55° C.

Esterification and/or transesterification catalysts are e.g. selected from the group consisting of bases, acids, and metal alcoholates such as titaniumtetraalcoholate, which are generally used for this purpose.

For esterification of free acids, coupling reagents, preferably selected from the group comprising EDCI, DCC/DMAP, and/or methods such as the Yamaguchi esterification are used in particular.

In this method, suitable solvents are usually selected from the group consisting of hydrocarbons such as alkanes, benzene and alkylated derivatives; ethers; dichlormethane; chloroform; chlorated aromates; carbon acid amides; alkylated carbon acid amides; sulfolane; DMPU; glymes; alkyl and arylnitriles; carbon acid esters; tertiary amines; and mixtures thereof; and are preferably selected from the group consisting of methyl-tert.-butylether, diethylether, tetrahydrofurane, glymes, sulfolane, chloroform, dichlormethane and/or mixtures thereof; and are particularly preferably selected from the group consisting of chloroform and dichlormethane.

Preferably, the solvents should be anhydrous.

A further subject of the present invention relates to methods for synthesizing a compound with the general formula VII with $E \neq CH_3$, preferably with $E=CH_2OH$, CHO and/or $CO_2H$, in which a protected compound with the general formula VII with $E=CH_3$, preferably VIIA with $E=CH_3$, is oxidized in allyl position and/or present functional groups are oxidized. Oxidation is performed preferably with selenium oxide.

A further subject of the present invention relates to methods for synthesizing a compound with the general formula VIIa and/or XVb, preferably with $E=CH_2OH$, CHO and/or $CO_2H$, in which a preferably protected compound with the general formula VII and/or XVb, for example with $E=CH_3$, is oxidized, preferably at position C7 or in allyl position or at other functional groups, with selenium(IV) compounds, particularly preferred selenium oxide and/or $C_6F_5SO_2H$, being preferably used as oxidation means. The oxidation means are used preferably catalytically. Alternatively, oxidation may occur bacterially or enzymatically with cell systems, with oxidation using $SeO_2$ being particularly preferred.

A further subject of the present invention relates to methods for synthesizing a compound with the general formula VII and/or XV, comprising addition of a nucleophile or electrophile to one or more, or the reduction, epoxidation or cyclopropanization of one or more double bonds of a compound with the general formula VII and/or formula XV.

The method according to the invention preferably comprises the reduction of the C8–C9 double bond; epoxidation of the C12–C13 double bond and/or addition of a nucleophile to C9.

The method according to the invention preferably comprises also the asymetrical and/or catalytical hydration of the C8–C9 double bond.

A further aspect of the present invention relates to methods for synthesizing epothilone macrocycles and derivatives with the general formula XVI:

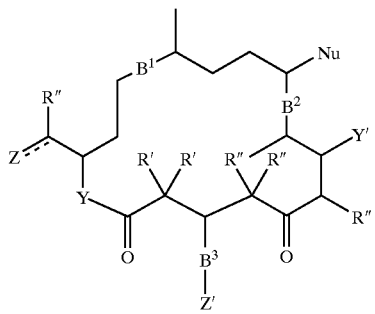

XVI wherein:
- $B^1$, $B^2$, $B^3$ are selected from the group consisting of single bonds; double bonds in the E(trans) form, Z(cis) form or as E/Z mixture; epoxide rings in the E(trans) form, Z(cis) form or E/Z mixture; cyclopropane rings in the E(trans) form, Z(cis) form or E/Z mixture; and/or combinations thereof; and being preferably selected from the group consisting of single and double bonds; and particularly preferably being selected from the group consisting of $B^1$ as Z double bonds or epoxide and $B^2$ and $B^3$ as single bond;
- R is selected from the group consisting of H; alkyl; aryl; alkyl-aryl such as $CH_2$-aryl, $C_2H_4$-aryl and the like; vinyl; cycloalkyl, particularly a 3- to 7-membered cycloalkyl; $CH_nF_{3-n}$ with n=0 to 3; oxacycloalkyl, particularly a 3- to 7-membered oxacycloalkyl; and/or combinations thereof; being particularly selected from the group consisting of H, methyl, ethyl, phenyl, benzyl; and being particularly preferred selected from the group consisting of H, methyl, ethyl and combinations thereof;
- R' is selected from the same group as R, and is much preferably H;
- R" is selected from the same group as R, and is much preferably methyl;
- Y is selected from the group consisting of S, NH, N-PG, NR and O; being preferably selected from the group consisting of NH, N-PG, NR and O, and being particularly preferably O;
- Y' is selected from the group consisting of H, OH, OR, O-PG, $NH_2$, $NR_2$, $N(PG)_2$, SR and SH; being preferably O-PG and/or OH;
- Nu is selected from the group consisting of R, O-PG, OR, $N(PG)_2$, $NR_2$, S-PG, SR, SeR, CN, $N_3$, aryl and heteroaryl; being preferably selected from the group consisting of R, O-PG, OR, $N(PG)_2$ and $NR_2$, and being particularly preferably H;
- Z is selected from the group consisting of —OH, —O-PG, —OR, =O, =N-Nu, =CH-hetaryl, =CH-aryl and =$PR_3$, where all previously mentioned double bound groups may be present in the E(trans) form, Z(cis) form or as E/Z mixture; being preferably =CH-hetaryl; and being particularly preferred selected from the group consisting of =O, (E)-(2-methylthiazol-4-yl)-CH= and (E)-(2-methyloxazol-4-yl)-CH=;
- Z' is selected from the group consisting of O, OH, OR, O-PG, $N(H)_{1-2}$, $N(R)_{1-2}$, $N(PG)_{1-2}$, SR, S-PG and R; being preferably O, O-PG and/or OR;
- $B^3$ is selected from the group consisting of single or double bonds in the E(trans) form, Z(cis) form or as E/Z mixture; being preferably selected from the group consisting of single and double bonds with heteroatoms such as O, S and N; and being particularly preferred a single bond to O-PG and/or OH;
- PG is a protecting group, and is preferably selected from the group consisting of allyl, methyl, t-butyl (preferably with EWG), benzyl, silyl, acyl and activated methylene derivatives such as methoxymethyl, alkoxyalkyl or 2-oxacycloalkyl; being preferably—predominantly for alcohol and amine functions—selected from the group consisting of trimethylsilyl, triethylsilyl, dimethyl-tert-butylsilyl, acetyl, propionyl, benzoyl, tetrahydropyranyl as well as protecting groups protecting neighbouring or bivalent groups ($PG_2$) concomitantly under formation of 5- to 7-membered rings, such as succinyl, phthalyl, methylene, ethylene, propylene, 2,2-dimethylpropa-1,3-diyl, acetonide; and/or combinations of all previously named protecting groups,
- alkyl is selected from the group consisting of hydrocarbons, also of branched isomers, preferably with $C_{1-20}$, particularly with 1 to 8 carbon atoms;
- aryl is selected from the group consisting of phenyl, naphthyl, benzyl, and their derivatives, preferably with up to five alkyl, alkoxy and/or halogen substituents, preferably from those with up to three substituents, particularly preferred with up to one substituent; preferably being selected from the group consisting of phenyl and benzyl derivatives; and combinations of these;
- Hetaryl/heteroaryl is selected from the group consisting of five- or six-membered heteroaromates with one or more O, S and N atoms and their derivatives with up to four alkyl, alkoxy and/or halogen substituents, preferably from those with up to two substituents, particularly preferred with up to one substituent; preferably being selected from the group consisting of oxazole, thiazole and pyrimidin derivatives; and particularly preferred being an alkylthiazole derivative; and combinations thereof; with being particularly preferred Z=O, (E)-(2-methylthiazol-4-yl)-CH=, (E)-(2-methyloxazol-4-yl)-CH=; R'=H; R"=Me; Y', Z'=O-PG, OH and/or Y=O.

Synthesis of epothilone macroycles and derivatives with the general formula XVI particularly occurs by ring forming lactonization and/or reactions of the Reformatsky type and/or macroaldolizations of the open-chain compound with the general formula XVa and/or XVb, with couplings at C2–C3 and/or C6–C7 are being preferred, respectively, preferably with EWG=H; E=CHO, $CO_2R$, $CO_2PG$; Y", $B^3$-Z'=OH or Y"+$B^3$-Z'=(=O).

The alternative Y", $B^3$-Z'=OH provides an acetal on position C3, whereas the alternative Y"+$B^3$-Z'=(=O) stands for a respective aldehyde function on position C3.

Reactions of the Reformatsky type within the scope of the present invention are reactions of halogene carbon acid esters or helogene ketones with aldehydes or ketones in presence of metals. As it is the case with Grignard compounds, this type of reaction comprises metalorganical reaction steps, which enable a C—C coupling particularly at C2–C3 and/or C6–C7.

Preferred reactions of the Reformatsky type within the scope of the present invention comprise reacting compounds XVa and/or XVb with X=Cl, Br, I with chromium(II) salts, indium and/or zinc and/or their salts.

In a particularly preferred embodiment of the method according to the invention, compounds XVa and/or XVb are reacted to compounds XVa and/or XVb mit X=M, with M being selected from the group consisting of ZnX, MgX, Li, $CrX_2$, $SmX_2$ and $InX_2$; and X being preferably halide. Then, the ring is closed particularly by electrophilic C2 or C7 components.

A special embodiment of a method for macrocyclene synthesis comprises the following steps:
(a) Converting compounds XI and XIa to compounds XI with X'=M, with M being selected from the group consisting of ZnX, MgX, Li, CrX$_2$, SmX$_2$ and InX$_2$; and X being preferably halide; and
(b) Reacting compounds from step a) with electrophilic C-7 components, e.g. of type VII, with suitable substituents E, preferably with E=CHO.

Of course, the synthesis components according to the invention with the general formulas VII to XVI as well as derived compounds may be presented in non-racemic form at the position corresponding to the α-hydroxy position of the compound with the general formula I, as the above described α-hydroxyketones according to the invention. The person skilled in the art may transfer offhand the principles for the synthesis of respective non-racemic synthetic building blocks with the general formulae VII to XVI which are presented by example of compounds with the general formulae I to VI and which are illustrated in the examples.

The invention in its embodiments is not limited to the aforementioned preferred embodiment examples. Rather, a plurality of variants are conceivable which use the presented solutions for basically different embodiments as well.

In the following, the present invention is illustrated with further examples which are not intended to be limiting in any way.

EXAMPLES

No statement regarding the absolute configuration or optic purity is constituted by the stereo centers shown in the formulas; in this case, they constitute only non racemic (optically active) products.

Furthermore, the abbreviations according to Table 1 are used in the examples:

TABLE 1

| Ac | acetyl |
|---|---|
| AYS | lipase from *Candida rugosa* |
| BSDR | *Bacillus stearothermophilus* diacetylreductase |
| CAA/CAL-A | lipase type A from *Candida antartica* |
| CAB/CAL-B | lipase type B from *Candida antartica* |
| CD | cyclodextrine |
| CPGC | chiral phase gas chromatography |
| DMF | N,N-dimethylformamide |
| E | enantioselectivity (enantiomeric ratio) according to Chen, C. S.; Fujimoto, Y.; Girdaukas, G.; Sih, C. J. J. Am. Chem. Soc. 1982, 104, 7294–7299. |
| e.e. | enantiomeric excess |
| LDH | lactate dehydrogenase |
| MJ | lipase from *Mucor javanicus* |
| MPA | methoxyphenyl acetic acid |
| NAD(H) | (reduced) nicotinamide adeninedinucleotide |
| NADP(H) | (reduced) nicotinamide adeninedinucleotide phosphate |
| n.d. | not determined |
| NMR | nuclear magnetic resonance spectroscopy |
| O-PG | O-protecting group |
| PPL | porcine pancreas lipase |
| PS | lipase from *Pseudomonas cepacia* |
| pTsOH | para-toluene sulfonic acid |
| TBDMS | see TBS |
| TBS(O) | tert-butyl-di-methyl-silyl(-ether) |
| t-Bu | tert-butyl |
| TMS | tetramethylsilane |

Example 1

Part A—Synthesis of Racemic O-acylacyloins and their Precursors tert-Butyl-2-acetoxy-2-acetyl-4-hexenoate

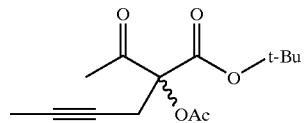

3.24 g (15.0 mmol) tert-butyl-2-acetoxyacetoacetate is added to a suspension of 660 mg (16.5 mmol) sodium hydride in 30 ml DMF at 0° C. After termination of the gas formation, 2.00 g (15.0 mmol) 1-bromium-2-butine is added at 0° C. The orange colored solution was stirred for 40 min, and was brought to room temperature in 15 min. After addition of 120 ml diethylether, several washings with water were performed and a final wash with concentrated sodium chloride solution. The organic phase was dried with Na$_2$SO$_4$, filtered, and the solvent was removed in vacuo.

Yield 3.83 g (14.3 mmol, 95%).

R$_f$ value approx. 0.57 with ethylacetate/hexane=1:4.

3-Acetoxy-5-heptine-2-one

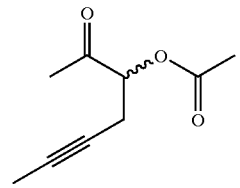

1.61 g (6.00 mmol) tert-butyl-2-acetoxy-2-acetyl-4-hexenoate, 114 mg (0.60 mmol) para-toluenesulfonic acid monohydrate and 20 ml benzene are stirred for 2 h at 78° C. 2 h. After termination of the reaction (after gas formation, color change), the raw product was put onto silica gel and eluted with ethylacetate/hexane=1:4. The fraction with the desired product is evaporated in vacuo.

Yield 922 mg (5.48 mmol, 91%).

Tert-butyl-2-acetoxy-2-acetyl-4-hexenoate

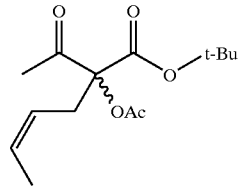

630 mg (2.3 mmol) tert-butyl-2-acetoxy-2-acetyl-4-hexenoate is added to a suspension of 120 mg Lindlar catalyst in 50 ml ethylacetate, and is evacuated twice and put under light positive pressure in a hydrogen atmosphere. After stirring for 24 h, it is filtered with ethylacetate through Celite®, washed with saturated sodium hydrogencarbonate solution, dried with Na$_2$SO$_4$, filtered, and the solvent was removed in vacuo.

Yield 628 mg (2.32 mmol, 99%).

3-Acetoxy-5-heptene-2-on

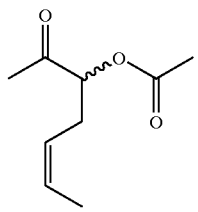

433 mg (1.60 mmol) tert-butyl-2-acetoxy-2-acetyl-4-hexenoate, 30 mg (0.16 mmol) para-toluenesulfonic acid monohydrate and 6 ml benzene are stirred for 4 h at 78° C. After termination of the reaction (after gas formation, color change), the raw product is put onto silica gel, and eluted with ethylacetate/hexane=1:4. The fraction with the desired product is evaporated in vacuo.

Yield 205 mg (1.20 mmol, 75%).

$R_f$ value approx. 0.50 with ethylacetate/hexane=1:4.

3-Acetoxy-6-methyl-heptane-2-on

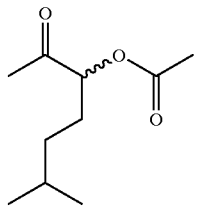

300 mg (1.63 mmol) 3-acetoxy-5-heptene-2-on and 60 mg 5% palladium on carbon were stirred in dry ethanol at room temperature. After three times evacuation and gasing with hydrogen, the gas is slowly directed through the suspension for additional 25 min. After filtration through Celite® and drying over $Na_2SO_4$, filtration was performed, and the solvent was removed in vacuo.

Yield 302 mg (1.62 mmol, 99%).

Part B—Diastereoselective Syntheses and Diastereomeric Separations of Acyloin Derivatives and Presentation of Non Racemic Acyloins, Acyloin Derivatives and Epothilone North Moiety Components (4S,5R,2'-non-rac)-1,5-Dimethyl-4-phenyl-3-(2'-benzyloxy-5',9'-dimethyldeca-4'(Z),8'-dienoyl)-imidazolidine-2-on:

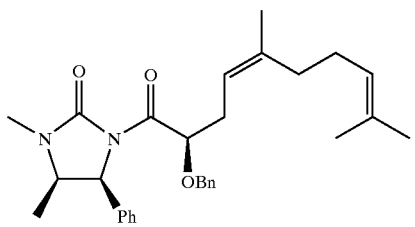

An n-butyllithium solution (1.88 ml, 10 M in hexane, 18.78 mmol) was added dropwise to a solution of diisopropylamine (2.65 ml, 1.90 g, 18.8 mmol) in THF (25 ml) at 0° C. The resulting LDA solution was slowly added dropwise at −78° C. to a solution of (4S,5R)-1,5-dimethyl-4-phenyl-3-(benzyloxyacetyl)-imidazolidine-2-on (5.30 g, 15.7 mmol) in THF (25 ml). After stirring for 1 h at −78° C., neryl bromide (3.40 g, 15.7 mmol) was added dropwise. After stirring for three hours at −78° C., the cooling bath was removed, and stirred for 15 min at ambient temperature. After quenching with a saturated $NH_4Cl$ solution (25 ml), the organic solvent was removed in the vacuum, and the remaining aqueous phase was diluted with demin. water (25 ml). It was extracted three times with 75 ml $Et_2O$, and the combined organic phases were dried over $Na_2SO_4$. Then, it was removed from the drying agent by filtration, and the solvent was removed in the vacuum.

The product was purified by silica gel chromatography (dimensions of the column: 30×3 cm, EtOAc/petrol ether= 1:2).

Yield: 3.64 g (7.67 mmol, 49%).

Non-Racemic 2-benzyloxy-N-methoxy-N,5,9-trimethyldeca-4(Z),8-dienoylamide:

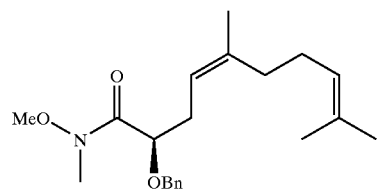

Trimethyl aluminium solution (4.50 ml, 2 M in toluene, 9.00 mmol) was dropped slowly to a suspension of N,O-dimethyl-hydroxylamine-hydrochloride (878 mg, 9.00 mmol) in $CH_2Cl_2$ (12 ml) at 0° C. The mixture was stirred at ambient temperature for 15 min, and then was cooled to −10° C. Now, a solution of (4S,5R,2'-non rac)-1,5-dimethyl-4-phenyl-3-(2'-benzyloxy-5',9'-dimethyldeca-4'(Z),8'-dienoyl)imidazolidine-2-one (see above, 1.42 g, 3.00 mmol) in $CH_2Cl_2$ (12 ml) was slowly added dropwise. It was stirred for one hour at −10° C., two hours at 0° C., and 30 minutes at ambient temperature. The reaction mix was finally added to a mixture of 0.5 N HCl (100 ml) and $CH_2Cl_2$ (50 ml), and was shook intensively for 5 min. Phases were separated, and the aqeous phase was extracted twice with $CH_2Cl_2$ (2×25 ml). The combined organic phases were washed with 0.5 N HCl (60 ml) and 1 M phosphate buffer (60 ml, pH=7.0), and subsequently dried over $Na_2SO_4$. Then, it was removed from the drying agent by filtration, and the solvent was removed in the vacuum.

The product was purified by silica gel chromatography (dimensions of the column: 30×3 cm, EtOAc/petrol ether= 1:2).

Yield: 779 mg (2.25 mmol, 75%).

Non Racemic 3-benzyloxy-6,10-dimethylundeca-5(Z),9-dien-2-one:

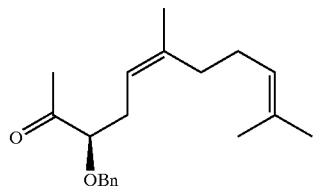

Methyllithium-lithiumbromide complex (1.87 ml, 1.5 M in THF, 2.80 mmol) was dropped to a solution of non-racemic 2-benzyloxy-N-methoxy-N,5,9-trimethyldeca-4(Z), 8-dienoylamide (see above, 345 mg, 1.00 mmol) in $CH_2Cl_2$ (15 ml) at −78° C. It was stirred for 40 min at −78° C., then the reaction mix was pumped through a stainless steel canula onto a mixture of saturated $NH_4Cl$ solution (20 ml), 14 ml hexane and 7 ml CH$_2$Cl$_2$ cooled to 0° C. and intensively stirred. After thawing to ambient temperature, the mixture was diluted with saturated NaCl solution (50 ml) and with a 3:1 hexane/CH$_2$Cl$_2$ mixture (50 ml). Again, it was agitated intensively, and after phase separation, the aqeous phase was extracted again with CH$_2$Cl$_2$ (30 ml). The combined organic phases were washed with saturated NaCl solution (150 ml) and dried over Na$_2$SO$_4$. Then it was removed from the drying agent by filtration, and the solvent was removed in the vacuum. The product was obtained with a high degree of purity.

Yield: 308 mg (1.03 mmol, nearly quantitative).
$[\alpha]_D^{25}$ (c=1, CHCl$_3$)=−18.0°.
11-(tert-Butyl-dimethyl-silanyloxy)-3-hydroxy-6,10-dimethyl-undec-5-en-2-one 400 ml saturated potassium carbonate solution is added to 1.94 g (5.05 mmol) 3-acetoxy-11-(tert-butyl-dimethylsilyloxy)-6,10-dimethyl-5-undecene-2-one in 20.0 ml methanol. After termination of the reaction (accurate DC control, e.g. approx. 10 min at room temperature), 30 ml of the NaCl solution is added and five times extracted with 30 ml diethylether. The combined organic phases are washed again with NaCl solution, and dried over sodium sulfate, the solvent was then removed in the vacuum, and silica gel chromatography was performed with the residue.

Yield 1.68 g (4.92 mmol, 97%).
R$_f$ value 0.42.
C$_{19}$H$_{38}$O$_3$Si (342.59).
(R)-Methoxy-phenyl-acetic acid [(1R)-1-acetyl-9-(tert-butyl-dimethyl-silanyloxy)-4,8-dimethyl-non-3-enyl]ester and (R)-Methoxy-phenyl-acetic acid [(1S)-1-acetyl-9-(tert-butyl-dimethyl-silanyloxy)-4,8-dimethyl-non-3-enyl]ester To 50 mg (0.146 mmol) of 11-(tert-butyl-dimethyl-silanyloxy)-3-hydroxy-6,10-dimethyl-undec-5-ene-2-one, 27 mg (0.161 mmol) (R)-1-methoxy-phenyl-acetic acid and 4 mg of (0.029 mmol) 4,4'-dimethylaminopyridine (DMAP) in 1.0 ml CH$_2$Cl$_2$, 56 mg (0.292 mmol) of the coupling reagent EDCI were added, and stirred for 18 hrs at room temperature. After addition of 5 ml diethylether, it is extracted twice with 2 ml water and 2 ml NaCl solution, the organic phase is dried over Na$_2$SO$_4$, and the solvent is removed in vacuo. The O-methylmandelate (102 mg) contains two diastereomers, which can be separated by chromatography on a silica gel column with 1.0×20.0 cm, diethylether/petrol ether=2:9.

Total yield: 53 mg (0.108 mmol, 74%).
C$_{28}$H$_{46}$O$_5$Si (490.75).
Fraction I
18 mg (0.037 mmol, 25%).
R$_f$ value 0.31 (diethylether/petrol ether=1:4).
Rotation value=−19.1.
Fraction II
Yield 23 mg (0.047 mmol, 32%).
R$_f$ value approx. 0.22 (diethylether/petrol ether=1:4).
Rotation value=−23.9°.
C$_{28}$H$_{46}$O$_5$Si (490.75).
Optically active 11-(tert-butyl-dimethyl-silanyloxy)-3-hydroxy-6,10-dimethyl-undec-5-ene-2-one Mild basic hydrolysis (see below) of a diastereomeric methoxy-phenyl-acetic acid [(1-acetyl-9-(tert-butyl-dimethyl-silanyloxy)-4,8-dimethyl-non-3-enyl]ester gives a non racemic product.
(R)-Methoxy-phenyl-acetic acid-9-(tert-butyl-dimethyl-silanyloxy)-4,8-dimethyl-1-[1-methyl-2-(2-methyl-thiazol-4-yl)-vinyl]-non-3-enyl ester

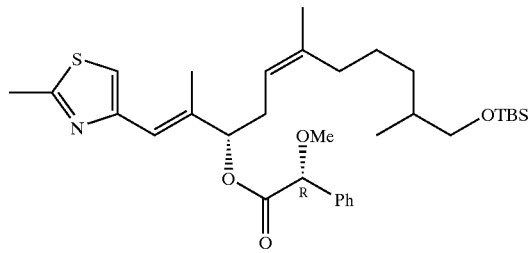

A solution of 1022 mg (2.92 mmol) of 2-methyl-4-(methyl-tributylphosphonium-bromide)-1,3-thiazole in 19.0 ml abs. THF was cooled to −65° C., and 1.56 ml (3.12 mmol) of a 2.0 M solution of sodium hexamethyl disilazide in THF was slowly added dropwise. After stirring for 10 min, a solution of 1194 mg (2.43 mmol) of (R)-methoxy-phenyl-acetic acid (3S)-1-acetyl-9-(tert-butyl-dimethyl-silanyloxy)-4,8-dimethyl-non-3-enyl ester in 8.0 ml abs. THF was slowly added dropwise.

After stirring for 60 min at −65° C., 45 ml saturated NH$_4$Cl solution was added. The phases were separated, and the aqueous phase was extracted five times with 25 ml diethylether. The organic phases were combined and washed three times with 30 ml demin water and once with 50 ml saturated NaCl solution. Finally, it was dried over Na$_2$SO$_4$, filtered, and vacuum concentrated. The resulting brown oil was purified by flash chromatography on silica gel (paramaters of the chromatography column: 2.0×20.0 cm, ethylacetate/petroleum ether=1:5).

Yield 1.3 g (2.3 mmol, approx. 95%).
R$_f$ value 0.37 (ethylacetate/petrol ether=1:5).
(R)-Methoxy-phenyl-acetic acid (R)-9-(tert-butyl-dimethyl-silanyloxy)-4,8-dimethyl-1-[1-methyl-2-(2-methyl-thiazol-4-yl)-vinyl]-non-3-enyl ester

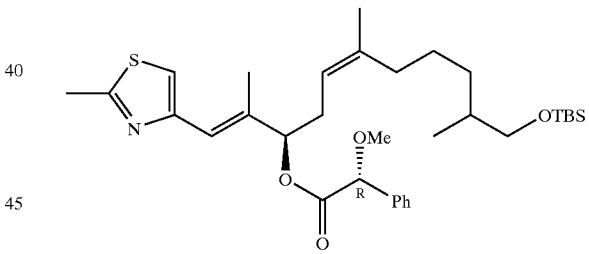

A solution of 1018 mg (2.91 mmol) 2-methyl-4-(methyl-tributylphosphoniumbromide)-1,3-thiazole in 19.0 ml abs. THF was cooled to −65° C., and 1.39 ml (2.79 mmol) of a 2.0 M solution of sodium hexamethyl disilazide in THF was slowly added dropwise. After stirring for ten minutes, a solution of 1190 mg (2.42 mmol) (R)-methoxy-phenyl-acetic acid (3R)-1-acetyl-9-(tert-butyl-dimethyl-silanyl-oxy)-4,8-dimethyl-non-3-enyl ester in 8.0 ml abs. THF was slowly added dropwise.

After stirring for 60 min at −65° C., 45 ml saturated NH$_4$Cl solution was added. The phases were separated, and the aqueous phase was extracted five times with 25 ml diethylether. The organic phases were combined and washed three times with 30 ml demin water and once with 50 ml saturated NaCl solution. Finally, it was dried over Na$_2$SO$_4$, filtered, and vacuum concentrated. The resulting brown oil was purified by flash chromatography on silica gel (paramaters of the chromatography column: 2.0×20.0 cm, ethylacetate/petroleum ether=1:5).

Yield 1.282 mg (2.19 mmol, 90%).
$R_f$ value 0.37 (ethylacetat/petrol ether=1:5).
$C_{33}H_{51}NO_4SSi$ (585.91).

Part C—Hydrolyses of O-Acylacyloins

The enzymes described below were used in the following:
Lipases: *Candida antarctica* (Novo lipase B~Chirazyme L2, CAL-B), *Candida antarctica* (Novo, lipase A, CAL-A), *Candida rugosa* (Amano AY, CRL), *Aspergillus niger* (Amano, ANL), *Pseudomonas cepacia* (Amano PS, PCL-PS). *Pseudomonas cepacia* (Amano AK, PCL-AK), *Pseudomonas* sp. (Chirazyme L6, PSL). AYS=*Candida rugosa*, CAA=*Candida antartica* A, CAB=*Candida antartica* B, MJ=*Mucor javanicus*, PS=*Pseudomonas cepacia*, PPL=porcine pancreas lipase.

Pig liver esterase (PLE, Sigma).

Production of recombinant esterases from *Pseudomonas fluorescens* (PFE, PFE-II), *Streptomyces diastatochromogenes* (SDE) by expression in *E. coli* according to literature (Krebsfänger, N.; Zocher, F.; Altenbuchner, J.; Bornscheuer, U. T. *Enzyme Microb. Technol.* 1998, 21, 641–646. Khalameyzer, V.; Bornscheuer, U. T. *Biotechnol. Lett.* 1999, 21, 101–104. Khalameyzer, V.; Fischer, I.; Bornscheuer, U. T.; Altenbuchner, *J. Appl. Environm. Microbiol* 1999, 65, 477–482.)

Recombinant pig liver esterases (rPLE) by expression in the yeast *Pichia pastoris*. (Musidlowska, A.; Lange, S.; Bornscheuer, U. T. *Angew. Chem. Int. Ed. Engl.* 2001, in press. Lange, S.; Musidlowska, A.; Schmidt-Dannert, C.; Schmitt, J.; Bornscheuer, U. T. *Chem. Bio. Chem.* 2001, in press).

General Prescription I for (Racemic) Saponification of O-acyl-acyloins

The ester is dissolved in methanol (e.g. 0.05–1M, generally approx. 0.13M); then, aqueous base is added (80 µl per mmol of ester), preferably—and if not mentioned separately—in saturated, aqueous potassium carbonate solution. After termination of the reaction (e.g. 30 min), saturated NaCl solution (approx. 1.5× the volume of methanol) and a fivefold volume of ether is added. The organic phase is washed thoroughly with NaCl, dried with sodium sulfate, filtered, and the solvent is removed in vacuo. Further purification may be performed e.g. by silica gel chromatography.

General Prescription II for Enzymatic Racemate Cleavage of O-acyl-acyloins (Small Amounts)

Lipase or esterase (e.g. approx. 20 mg), 0.7 ml phosphate buffer (0.1 M, pH 7.0) and the acyloin ester (e.g. 5 µl) are added subsequently to a suitable vessel (here e.g. a 1.5 ml Eppendorf® tube). The mixture is agitated vigorously, and then mixed as usual (Vortex, 300 strokes/minute) at 0–60° C. depending on the enzyme, usually at room temperature. The reaction is terminated by addition of acetone. Generally, the process is controlled by a titrator or a polarimeter, or over time, usually in approx. 30 min. Ethylacetate (0.4 ml) is added, separated by shaking and centrifuged (at 8.000 g for 5 min). The top organic layer is removed, and the rest is extracted again. The extraction may be also be achieved more difficultly without centrifugation. After drying of the combined organic phases over $Na_2SO_4$, a further centrifugation step may be performed (e.g. at 8.000 g for 5 min).

In the following table 2, examples for reactions according to the general prescription II with substrate IV $R^1$, $R^3$=Me are described (ee values according to GC, 99+=99–100%. [1] The e.e. values of the substrates are calculated values, alcohol/ester 1 and 2 refer to the other enantiomere, respectively).

TABLE 2

| substrate IV with $R^2$ = | enzyme | e.e. | excess alcohol | e.e. | excess ester | E |
|---|---|---|---|---|---|---|
| prenyl | AYS | 2% | alcohol 2 | 0% | ester 2 | 1 |
| | CAA | 89% | alcohol 2 | 1.9% | ester 1 | 20 |
| | CAB | 94% | alcohol 2 | 98% | ester 1 | >156 |
| | MJ | 26% | alcohol 2 | 0% | ester 1 | 2 |
| | PS | 99% | alcohol 2 | 99% | ester 1 | >200 |
| | PPL | 8% | alcohol 1 | 1% | ester 2 | 1 |
| methylallyl (trans)* (trans-crotyl) | AYS | 7% | alcohol 1 | 3% | ester 2 | 1 |
| | CAA | 88% | alcohol 2 | 76% | ester 1 | 36 |
| | CAB | 94% | alcohol 2 | 95% | ester 1 | >100 |
| | MJ | 37% | alcohol 2 | 2% | ester 1 | 2 |
| | PS | 27% | alcohol 2 | 100% | ester 1 | 12 |
| | PPL | 27% | alcohol 1 | 4% | ester 2 | 2 |
| methylallyl (cis)* (cis-crotyl) | AYS | 3% | alcohol 1 | 0% | ester 2 | 1 |
| | CAA | 69% | alcohol 2 | 33% | ester 1 | 8 |
| | CAB | 95% | alcohol 2 | 99+% | ester 1 | >200 |
| | MJ | 7% | alcohol 2 | 1% | ester 1 | 1 |
| | PS | 99+% | alcohol 2 | 99+% | ester 1 | 80096 |
| | PPL | 24% | alcohol 2 | 1% | ester 1 | 2 |
| | AYS | | | | | |
| | CAA | 63% | alcohol 2 | 9% | ester 1 | 5 |
| | CAB | 93% | alcohol 2 | 99+% | ester 1 | >200 |
| | MJ | | | | | |
| | PS | 96% | alcohol 2 | 99+% | ester 1 | >200 |
| | PPL | | | | | |
| hexyl | AYS | 68% | alcohol 1 | 1% | ester 2 | 5 |
| | CAA | 71% | alcohol 2 | 19% | ester 1 | 7 |
| | CAB | 93% | alcohol 2 | 99% | ester 1 | >120 |
| | PS | 34% | alcohol 2 | 99% | ester 1 | 9 |
| | PPL | 32% | alcohol 2 | 5% | ester 1 | 2 |
| benzyl | AYS | 5% | alcohol 2 | 1% | ester 1 | 1 |
| | CAA | 85% | alcohol 2 | 15% | ester 1 | 15 |
| | CAB | 84% | alcohol 2 | 14% | ester 1 | 13 |
| | MJ | 9% | alcohol 2 | 0% | ester 1 | 1 |
| | PS | 95% | alcohol 2 | 97% | ester 1 | >150 |
| | PPL | 44% | alcohol 1 | 2% | ester 2 | 3 |

TABLE 2-continued

| substrate IV with R² = | enzyme | e.e. | excess alcohol | e.e. | excess ester | E |
|---|---|---|---|---|---|---|
| butyl | AYS | 42% | alcohol 1 | 2% | ester 2 | 3 |
|  | CAA | 73% | alcohol 2 | 19% | ester 1 | 8 |
|  | CAB | 87% | alcohol 2 | 99+% | ester 1 | >150 |
|  | MJ | 15% | alcohol 1 | 1% | ester 1 | 1 |
|  | PS | 66% | alcohol 2 | 99+% | ester 1 | 30 |
|  | PPL | 1% | alcohol 1 | 2% | ester 1 | 1 |
| butynyl | AYS | 61% | alcohol 1 | 20%[1] | ester 2 | 5 |
|  | CAA | 66% | alcohol 2 | 14%[1] | ester 1 | 6 |
|  | CAB | 91% | alcohol 2 | 74–91%[1] | ester 1 | 47–67 |
|  | MJ | 17% | alcohol 2 | 1%[1] | ester 1 | 1 |
|  | PS | 8% | alcohol 2 | <5%[1] | ester 1 | 4 |
|  | PPL | 25% | alcohol 1 | 3%[1] | ester 2 | 2 |
| neryl | AYS | 2% | alcohol 2 | 1% | ester 1 | 1 |
|  | CAA | 78% | alcohol 2 | 52% | ester 1 | 14 |
|  | CAB | 89% | alcohol 2 | 55% | ester 1 | 31 |
|  | MJ |  | not determined |  | not determined |  |
|  | PS | 94% | alcohol 2 | 95% | ester 1 | >100 |
|  | PPL |  | not determined |  | not determined |  |
| 2-acetoxy-cyclopentanone C5(c) | AYS | 64% | alcohol 1 | 15% | ester 2 | 5 |
|  | CAA | 47% | alcohol 1 | 0% | ester 2 | 3 |
|  | MJ | 35% | alcohol 1 | 1% | ester 2 | 2 |
|  | PS | 77% | alcohol 1 | 95% | ester 2 | 27 |
|  | PPL | 60% | alcohol 1 | 8% | ester 2 | 4 |

*Determined from an approx. 9/1 mixture of the trans and cis isomeres.

General Prescription III for Enzymatic Racemate Cleavage of O-acyl-acyloins

The ester was dissolved in 0.1 M phosphate buffer pH 7.0 (concentration approx. 0.07 M) and lipase was added (e.g. up to 25 vol % of the acyloin ester). The reaction mix was shaken during the reaction until termination if the reaction (DC and GC control). Acetone was added (½ of the buffer volume) and five times extracted with ethylacetate (1.5× buffer volume).

The organic phases were washed twice with NaCl solution, dried with sodium sulfate, and the solvent was removed in vacuo. Alcohol and ester were separated by chromatography (e.g. on silica gel with ethylacetate/petrol ester=1:6).

General Prescription IV for Enzymatic Racemate Cleavage of O-acyl-acyloins

Small batches: 10 mg hydrolase (lipase or esterase) was shaken in 1 ml sodium phosphate buffer (pH 7.5, 50 nM) in 2 ml reaction vessels at 37° C. (e.g. with thermoshaker—Eppendorf, Hamburg, Germany). Then, 200 μl substrate solution is added (10 mg/ml in toluene). After 20 hrs, the reaction was stopped by centrifugation of the enzyme, the toluene layer was removed and analyzed (e.g. by GC, polarimetry).

Larger batches: These are performed similiarly, but in 10 ml phosphate buffer with 200 mg hydrolase and 0.44 mmol (approx. 100 mg) acyloin ester in 3 ml toluene. At the end of the reaction, 10 ml toluene is added, the enzyme removed by centrifugation, and the organic layer separated. The aqueous phase is extracted another two times with 5 ml toluene, the combined organic phased dried ($Na_2SO_4$), and the solvent is separated in vacuo. Acyloin and the unreacted ester are separated by chromatography (e.g. on silica gel with petrol ether:ether, 4:1). Excess enantiomeres may be analyzed best by chiral phase gas chromatography (CP-GC), chemical identity by NMR spectroscopy.

General Prescription V for Enzymatically Catalyzed Transesterification in Organic Solvents (Enzymatic Esterification of Free Acyloins).

A solution of 0.44 mmol of the acyloins in 3 ml toluene, activated molecular sieve (3 Å), 200 mg lipase and vinyl acetate (1.2 equivalents) are reacted at 37° C. until the desired reaction has occured (shake, if necessary). The reaction is terminated by centrifugation, the solvent is removed and evaporated in the vacuum. Ester and unreacted free acyloin may be separated by chromatography (e.g. on silica gel with petrol ether:ether, 4:1). Excess enantiomeres may be analyzed best by chiral phase gas chromatography (CP-GC), chemical identity by NMR spectroscopy.

Instead of vinyl acetate, other active esters may be employed as well.

TABLE 3

Racemate cleavage of acyloin acetate UWE1b according to prescription IV (small)

| hydrolase[a] | turnover [%][b] | enantiomeric excess (e.e.)[b] | | E value[c] |
|---|---|---|---|---|
| | | acetate [% ee] | acyloin [% ee] | |
| CAL-A | 99 | 0 | 0 | 0 |
| CAL-B | 30 | 31 | 80 | 12 |
| ANL | 7 | n.d.[d] | n.d. | n.d. |
| CRL | 30 | 18 | 13 | 3 |
| PCL | 51 | >99 | 93 | >100 |
| PFE | 56 | >99 | 92 | >100 |
| SDE | 56 | >99 | 85 | 64 |

[a]Abbreviations see above, main text or manuals;
[b]according to GC;
[c]calculated according to Chen et al. (J. Am. Chem. Soc. 1982, 104, 7294–7299);
[d]n.d., not determined

TABLE 4

Racemate cleavage of acyloin acetate UWE3a, according to prescription IV (small).

| hydrolase[a] | turnover [%][b] | enantiomeric excess[b] | | E value[c] |
|---|---|---|---|---|
| | | acetate [% ee] | acyloin [% ee] | |
| CAL-B | 5 | 5 | 96 | >50 |
| PSL | 50 | >99 | >99 | >100 |
| PCL-AK | 50 | >99 | >99 | >100 |
| PLE[d] | 80 | >99 | 20 | 6 |
| rPLE[d,e] | 25 | 33 | >98 | >50 |
| SDE | 50 | >99 | >99 | >100 |
| PFE | 11 | 11 | 86 | 15 |
| PFE-II | 75 | <3 | <1 | 1 |

[a]Abbrev. see directory or manuals;
[b]according to GC;
[c]calculated according to Chen et al. (J. Am. Chem. Soc. 1982, 104, 7294–7299);
[d]reversed stereopreference;
[e]recombinant pig liver esterase.

Racemic Free Acyloins
(R,S) 3-Hydroxy-5-hepten-2-one

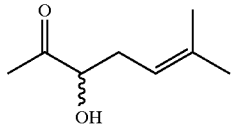

According to the general prescription, 48 mg (0.26 mmol) 3-acetoxy-5-hepten-2-one is hydrolyzed for 20 min, during which time the solution becomes cloudy and then yellowish. Chromatography (diethylether/petrole ether=1:4) gives:
Yield 28 mg (0.20 mmol, 77%).
$R_f$ value approx. 0.46 with ethylacetate/hexane=1:4.
(R,S) 3-Hydroxy-nonan-2-one
According to general prescription 1,60 mg (0.30 mmol) 3-acetoxy-nonan-2-one is hydrolyzed for 20 min, during which time the solution becomes cloudy and then yellowish. Chromatography gives:
Yield 42 mg (0.27 mmol, 88%).
$R_f$ value approx. 0.63 with ethylacetate/hexane=1:4.
(R,S) 3-Hydroxy-6-methyl-heptan-2-one

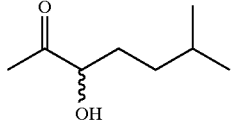

According to general prescription 1,47 mg (0.25 mmol) 3-acetoxy-6-methyl-heptan-2-one is hydrolyzed for 5 min, during which time the solution becomes cloudy and then yellowish.
Yield 32 mg (0.22 mmol, 88%).
(R,S) 3-Hydroxy-5(Z)-hepten-2-one

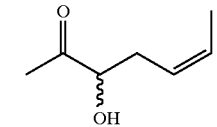

According to general prescription I,63 mg (0.25 mmol) 3-acetoxy-5(Z)-hepten-2-one is hydrolyzed for 6 min, during which time the solution becomes cloudy and then yellowish.

Yield 31 mg (0.24 mmol, 96%).
(R,S) (E) 3-Hydroxy-6,10-dimethyl-5,9-undecen-2-one

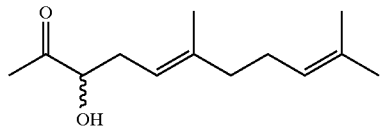

According to general prescription I,,63 mg (0.25 mmol) (E) 3-acetoxy-6,10-dimethyl-5,9-undecen-2-one is hydrolyzed for 6 min, during which time the solution becomes cloudy and then yellowish.
Yield 47 mg (0.22 mmol, 89%).
$R_f$ value approx. 0.35 with ethylacetate/hexane=1:4.
(R,S) (Z) 3-Hydroxy-6,10-dimethyl-5,9-undecen-2-one

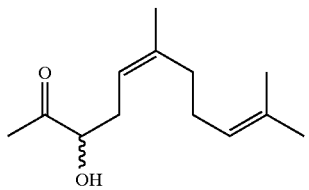

According to general prescription I,63 mg (0.25 mmol) (Z) 3-acetoxy-6,10-dimethyl-5,9-undecen-2-one is hydrolyzed for 6 min, during which time the solution becomes cloudy and then yellowish.
Yield 47 mg (0.22 mmol, 89%) of a yellow oil.
$R_f$ value 0.42 with ethylacetate/hexane=1:4.

Optically Inactive Non Racemic Alcohols and Esters

The respective starting material is not mentioned separately in the title.
Optically Active 3-hydroxy-heptan-2-one
According to general prescription III, 100 mg (0.58 mmol) 3-acetoxy-heptan-2-one is reacted with 6 mg *Candida antartica* B lipase in 10 ml buffer and stopped after 3.75 hrs. Chromatography gives:
Yield Alcohol: 20 mg (0.15 mmol, 26%).
Ester: 35 mg (0.20 mmol, 35%).
$R_f$ value Alcohol: approx. 0.33 with ethylacetate/hexane=1:4.
Ester: approx. 0.48 with ethylacetate/hexane 1:4.
$[\alpha]_D^{25}$ (approximate values)
Alcohol: +69.9° (c=0.410; CHCl$_3$; e.e. =82%).
Ester: +9.6° (c=1.805; CHCl$_3$; e.e. =78%).
Optically Active 3-hydroxy-nonan-2-one

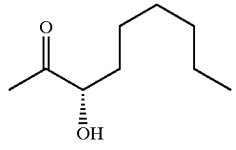

According to general prescription III, 16 mg (0.58 mmol) 3-acetoxy-nonan-2-one is reacted with 7 mg *Candida antartica* B lipase in 10 ml buffer and stopped after 4.5 hrs. Chromatography gives:
Yield Alcohol: 10 mg (0.063 mmol, 11%).
Ester: 46 mg (0.23 mmol, 40%).
$R_f$ value Alcohol: approx. 0.44 with ethylacetate/hexane=1:4.

$[α]_D^{25}$ Ester: approx. 0.61 with ethylacetate/hexane=1:4.
$[α]_D^{25}$ Ester: +6.3° (c=1.615; CHCl₃).

Optically Active 3-hydroxy-5(Z)-hepten-2-one

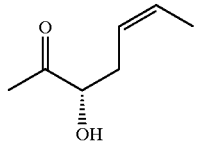

According to general prescription III, 32 mg (0.19 mmol) 3-acetoxy-5(Z)-hepten-2-one is reacted with 20 mg Amano PS lipase in 5 ml buffer and stopped after 40 min.
Chromatography gives the following products:
$R_f$ value Alcohol: approx. 0.30 with ethylacetate/hexane= 1:4.
Ester: approx. 0.50 with ethylacetate/hexane=1:4.

Optically Active 3-hydroxy-6-methyl-5-hepten-2-one

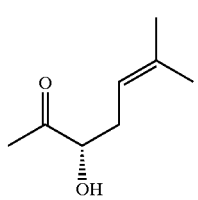

According to general prescription III, 200 mg (1.09 mmol) 3-acetoxy-6-methyl-5-hepten-2-one is reacted with 63 mg Amano PS lipase in 15 ml buffer and stopped after 6 hrs.

| Chromatography gives the following products: | | |
| --- | --- | --- |
| Yield | Alcohol: | 71 mg (0.50 mmol, 46%) of a clear, colorless oil |
| | Ester: | 103 mg (0.56 mmol, 52%) of a clear, colorless oil |
| $R_f$ value | Alcohol: | approx. 0.22 with ethylacetate/hexane = 1:4 |
| | Ester: | approx. 0.50 with ethylacetate/hexane = 1:4 |
| $[α]_D^{25}$: | Alcohol: | +77.3° (c = 0.979; CHCl₃) |
| | Ester: | −15.5° (c = 2.030; CHCl₃) |

Optically Active 3-hydroxy-4-phenylbutan-2-one

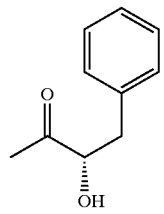

According to general prescription III, 150 mg (0.73 mmol) 3-acetoxy-4-phenylbutan-2-one is reacted with 38 mg Amano PS lipase in 15 ml buffer and stopped after 3 hrs.

| Chromatography gives the following products: | | |
| --- | --- | --- |
| Yield | Alcohol: | 51 mg (0.31 mmol, 43%) of a clear, colorless oil |
| | Ester: | 76 mg (0.37 mmol, 50%) of a clear, colorless oil. |
| $[α]_D^{25}$: | Alcohol: | +64.1° (c = 0.820; CHCl₃; e.e. = 89%) |
| | Ester: | −3.0° (c = 2.325; CHCl₃; e.e. = 85%) |

Optically Active 3-hydroxy-6,10-dimethylundeca-5(Z),9-dien-2-one

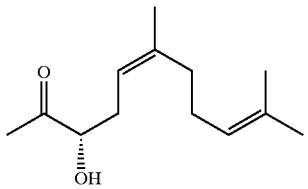

According to general prescription III, 200 mg (0.79 mmol) 3-acetoxy-6,10-dimethylundeca-5(Z),9-dien-2-one are reacted with 63 mg Amano PS lipase in 15 ml buffer and terminated after 6 hrs.

| Chromatography gives the following products: | | |
| --- | --- | --- |
| Yield | Alcohol: | 70 mg (0.33 mmol, 42%) of a clear, colorless oil |
| | Ester: | 107 mg (0.42 mmol, 54%) of a clear, colorless oil. |
| $R_f$ value | Alcohol: | approx. 0.38 with ethylacetate/hexane = 1:4 |
| | Ester: | approx. 0.52 with ethylacetate/hexane = 1:4 |
| $[α]_D^{25}$: | Alcohol: | +63.7° (c = 2.115; CHCl₃; e.e. = 95%) |
| | Ester: | −19.7° (c = 1.560; CHCl₃; e.e. = 97%) |

Optically Active (Z)-3-acetoxy-6,10-dimethyl-5,9-undecadien-2-one and (Z)-3-hydroxy-6,10-dimethyl-5,9-undecadien-2-one Hydrolysis (larger batch) with PCL according to general prescription IV gives optically active (Z)-3-acetoxy-6,10-dimethyl-5,9-undecadien-2-one (40% yield, >99% ee) and (Z)-3-hydroxy-6,10-dimethyl-5,9-undecadien-2-one (43% yield, 92% ee), E>>100.

Optically Active (E)-3-acetoxy-6,10-dimethyl-5,9-undecadien-2-one and (E)-3-hydroxy-6,10-dimethyl-5,9-undecadien-2-one Hydrolysis (larger batch) with PCL according to general prescription IV gives optically active (E)-3-acetoxy-6,10-dimethyl-5,9-undecadien-2-one (40% yield, 95% ee) and (E)-3-hydroxy-6,10-dimethyl-5,9-undecadien-2-one (32% yield, >99% ee), E>>100.

Optically Active (Z)-3-hydroxy-6,10-dimethyl-5,9-undecadien-2-one and (Z)-3-acetoxy-6,10-dimethyl-5,9-undecadien-2-one Acylation with PCL according to general prescription V gives optically active (Z)-3-hydroxy-6,10-dimethyl-5,9-undecadien-2-one (40% yield, 95% ee) and (Z)-3-acetoxy-6,10-dimethyl-5,9-undecadien-2-one (32% yield, >99% ee), E>>100.

Optically Active (E)-3-acetoxy-6,10-dimethyl-5-ene-11-hydroxy-undecan-2-one and (E)-3-hydroxy-6,10-dimethyl-5-ene-11-hydroxy-undecan-2-one Hydrolysis (0.94 mmol) with PCL according to general prescription IV gives optically active (E)-3-acetoxy-6,10-dimethyl-5-ene-11-hydroxy-undecan-2-one (28% yield, 92% ee) and alcohol (E)-3-hydroxy-6,10-dimethyl-5-ene-11-hydroxy-undecan-2-one (28% yield, >99% ee), E>>100.

Optically Active (E)-3-acetoxy-6,10-dimethyl-5-ene-11-O-TBDMS-undecane-2-one and (E)-3-hydroxy-6,10-dimethyl-5-ene-11-O-TBDMS-undecan-2-one Hydrolysis (1.25 mmol) with PCL (chirazyme L6) according to general prescription IV gives optically active (E)-3-acetoxy-6,10-dimethyl-5-ene-11-O-TBDMS-undecan-2-one (48% yield, 46% ee) and alcohol 3-hydroxy-6,10-dimethyl-5-ene-11-O-TBDMS-undecan-2-one (42% yield, >99% ee), E>>100. A further improvement of the optical yield of (E)-3-acetoxy-6,10-dimethyl-5-ene-11-O-TBDMS-undecan-2-one was achieved by a second kinetic racemate cleavage with PCL (Amano PS). Yield was 35% (E)-3-acetoxy-6,10-dimethyl-5-ene-11-O-TBDMS-undecane-2-one with >98% ee.

Example 2

The listed compounds may also be isomere mixtures, racemates, and/or diastereomers, if not mentioned explicitly otherwise. Compounds enriched with enantiomeres are usually indicated by listing a rotation value. If desired, the resulting products were purified by purification procedures known in the art.

1. Tert-butyl-2 bromo-acetoacetate

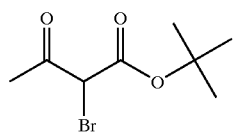

N-bromo-succinimide (58.7 g, 330 mmol) was added in portions to a solution of tert-butyl acetoacetates (49.0 ml, 47.5 g, 300 mmol) in Acetone (30 ml). The resulting solution was stirred for one hour at ambient temperature, and subsequently filtered. The filtrate was vacuum concentrated, and the residuum was reconstituted in 300 ml petroleum ether. After washing three times, each time with 100 ml water, the solution was dried over $Na_2SO_4$ and filtered. Then, the product was obtained by vacuum concentration.

2. Tert-butyl-2-acetoxy-acetoacetate

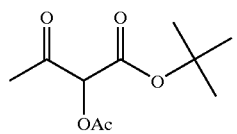

A solution of glacial acetic acid (10.6 ml, 186 mmol) in DMF (169 ml) was neutralized with triethylamine (25.8 ml, 186 mmol) under cooling with ice. Tert-butyl-2-bromo-acetoacetate (40.0 g, 169 mmol) was added dropwise to the resulting solution of triethylammonium acetate at 0° C. The ice bath was removed after the substance had been added completely, and the reaction mixture was stirred für two hours at room temperature. Then, water was added (280 ml), and the solution was extracted with ethylacetate (3×215 ml). The organic phases were combined, and washed with water (3×215 ml) and concentrated NaCl solution (1×215 ml). After drying over $Na_2SO_4$, filtration and vacuum concentration, the product oil was obtained, which was purified by double distillation at 12 mbar and 128° C.

3. (4Z)-2-Acetoxy-2-acetyl-5,9-dimethyl-deca-4,8-dienoic acid-tert-butyl ester

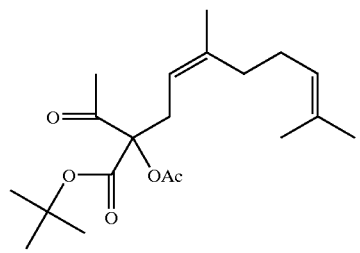

Tert-butyl-2-acetoxy-acetoacetate (19.5 g, 90 mmol) was slowly added dropwise to a suspension of NaH (2.59 g, 108 mmol) in DMF (180 ml) at 0° C. After gas development had stopped, neryl bromide (19.6 g, 90 mmol) was slowly added dropwise at 0° C. Finally, the ice bath was removed and it was stirred for 116 hrs at ambient temperature. The resulting yellow solution was diluted with diethylether (750 ml) and washed with water (3×200 ml) and concentrated NaCl solution (1×200 ml). The product was obtained after drying over $Na_2SO_4$, filtration and vacuum concentration.

4. (4Z)-2-Acetoxy-2-acetyl-5,9-dimethyl-10-hydroxy-deca-4,8-dienoic acid-tert-butyl ester Highly powderized selenium oxide (0.158 g, 1.42 mmol) was suspended in DCM (50 ml). Then, a 70% solution of tert-butyl hydroperoxide (10.2 g, 79.5 mmol) was added, and was stirred for 30 min at ambient temperature. Finally, 10.0 g (28.4 mmol) (4Z)-2-acetoxy-2-acetyl-5,9-dimethyl-deca-4,8-dienoic acid-tert-butyl ester was added and stirred for 48 hrs at ambient temperature. After vacuum concentration, 50 ml toluene was added and removed in the vacuum (by this, excess tert-butyl-hydroperoxide is removed). This was repeated three times, and the resulting product was separated by flash chromatography (parameters of the chromatography column: 5.0×19.5 cm, ethylacetate/petroleum ether=1:2).

5. Enantiomerically Enriched (4Z)-2-acetoxy-2-acetyl-5,9-dimethyl-10-hydroxy-deca-4-oic acid-tert-butyl ester

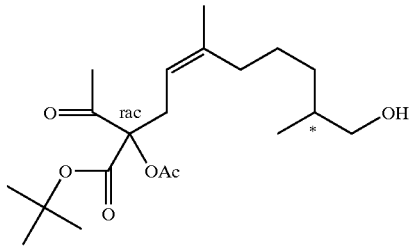

7.94 g (21.6 mmol) (4Z)-2-acetoxy-2-acetyl-5,9-dimethyl-10-hydroxy-deca-4,8-dienoic acid-tert-butyl ester was dissolved in 15.0 ml absolute methanol, and 750 μl demin. water was added. The resulting solution was degassed using three freeze-thaw cycles. Then, 185 mg Ru(R-BINAP)(OAc)$_2$ and a magnetic stirrer were added, and the resulting lemon-colored solution was transferred to an autoclave. The nitrogen atmosphere was displaced from the autoclave by three times filling and releasing of hydrogen gas (quality 5.0). Finally, a pressure of 100 bar hydrogen gas (quality 5.0) was applied and stirred for 25 hrs at ambient temperature.

The gas was released from the autoclave, and the solution was vacuum concentrated. The remaining product was purified by flash chromatography (parameters of the chromatography column: 4.5×25.0 cm, ethylacetate/petroleum-ether=1:2).

6. Enantiomerically Enriched 3-acetoxy-11-hydroxy-6,10-dimethyl-5-undecen-2-one

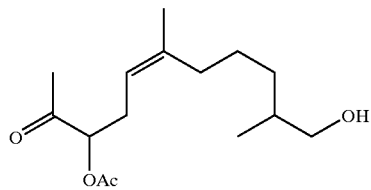

1.032 g (2.79 mmol) (9S)(4Z)-2-acetoxy-2-acetyl-5,9-dimethyl-10-hydroxy-deca-4-enoic acid-tert-butyl ester was dissolved in 28 ml DCM, and 2.80 ml TFA was added. After stirring for 2 hrs at ambient temperature, all volatile components were removed in the vacuum, and the remaining brown oil was dissolved in 28.0 ml methanol. Then, 5.6 ml of a saturated NaHCO$_3$ solution was added, and the resulting suspension was stirred for 140 min at ambient temperature. After addition of 200 ml ether, the organic phase was washed twice with 50 ml demin water and once with 50 ml concentrated NaCl solution, and was subsequently dried over Na$_2$SO$_4$. After filtration and vacuum concentration, the product was obtained which was purified by flash chromatography (parameters of the chromatography column: 2.0×20.0 cm, ethylacetate/petroleum-ether=2:3).

7. Enantiomerically Enriched 3-acetoxy-11-tert-butyl-dimethylsilyloxy-6,10-dimethyl-5-undecen-2-one

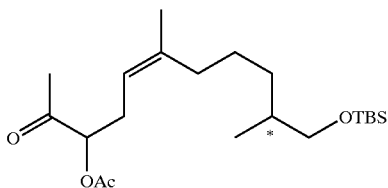

528 mg (1.95 mmol) 3-acetoxy-11-hydroxy-6,10-dimethyl-5-undecen-2-one was dissolved in 10.0 ml absolute DCM, and 541 µl (395 mg, 3.90 mmol) triethylamine and 12 mg (0.10 mmol) DMAP were added. The solution was cooled in an ice bath and stirred for five minutes. Then, 368 mg (2.44 mmol) TBDMSCl was added all at once, and the obtained solution was stirred for two hours at 0° C. and finally for 14 hrs at ambient temperature. A colorless suspension was obtained which was cooled to 0° C. prior to finally adding 460 µl methanol, and which was stirred for 30 min. Then, 15 ml diethylether and 15 ml saturated ammonium chloride solution was added and stirred intensively. The aqueous phase was extracted twice with 10 ml diethylether, and the organic phases were combined. It was washed with 15 ml sat. NaCl solution, dried over Na$_2$SO$_4$, filtered and vacuum concentrated. The remaining product was purified by flash chromatography (parameters of the chromatography column: 2.0×20.0 cm, ethylacetate/petroleum-ether=1:10).

8. 3-Acetoxy-11-(tert-butyl-dimethyl-silanyloxy)-2,6,10-trimethyl-1-(2-methyl-thiazol-4-yl)-undeca-1,5-diene

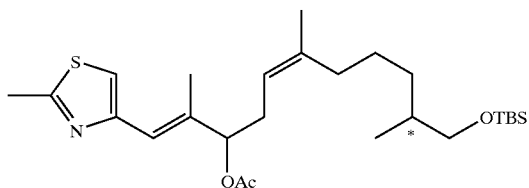

A solution of 524 mg (1.50 mmol) 2-methyl-4-(methyl-tributylphosphonium-bromide)-1,3-thiazole in 10.0 ml abs. THF was cooled to −63° C., and 749 µl (1.50 mmol) of a 2.0 M sodium hexamethyl disilazide solution in THF was slowly added dropwise. After stirring for fifteen minutes, a solution of 480 mg (1.25 mmol) 3-acetoxy-11-tert-butyl-dimethylsilyloxy-6,10-dimethyl-5-undecene-2-one in 4.0 ml THF was slowly added dropwise.

After stirring for 30 min at −63° C., the solution was heated to 55° C., and stirred for another hour. Then, the heating bath was removed, and 20 ml saturated NH$_4$Cl solution was added. The phases were separated, and the aqueous phase was extracted three times with 20 ml diethylether. The organic phases were combined and washed three times with 20 ml demin. water and once with 20 ml saturated NaCl solution. Finally, it was dried over Na$_2$SO$_4$, filtered, and vacuum concentrated. The remaining product was purified by flash chromatography (parameters of the chromatography column: 2.0×20.0 cm, ethylacetate/petroleum-ether=1:4).

9. Enantiomerically Enriched 11-(tert-butyl-dimethyl-silanyloxy)-2,6,10-trimethyl-1-(2-methyl-thiazole-4-yl)-undeca-1,5-dien-3-ole

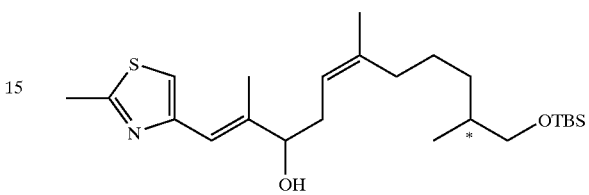

221 mg (0.461 mmol) 3-acetoxy-11-(tert-butyl-dimethyl-silanyloxy)-2,6,0-trimethyl-1-(2-methyl-thiazole-4-yl)-undeca-1,5-diene and 64 mg (0.461 mmol) K$_2$CO$_3$ were stirred in 5.5 ml absolute methanol for two hours at ambient temperature. Then, 30 ml ethylacetate was added, and the organic phase was washed with demin water (3×10 ml) and with saturated NaCl solution (1×10 ml), dried over Na$_2$SO$_4$, filtered, and finally vacuum concentrated. A product was obtained which was purified by flash chromatography (parameters of the chromatography column: 2.0×20.0 cm, ethylacetate/petroleum-ether=1:4).

10. (4S)-3-[(3S)-4,4-dimethyl-1,5-dioxo-3-hydroxyheptyl]-4-benzyl-2-oxazolidinone

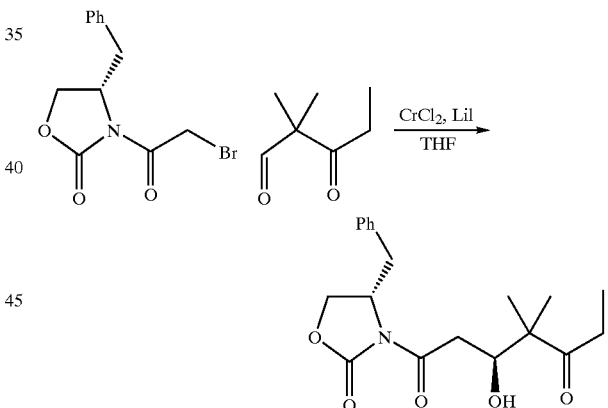

9.0 ml (14.4 mmol) butyl lithium (1.6M in hexane) was added dropwise to 2.55 g (14.4 mmol) (S)-4-benzyl-2-oxazolidinone in 50 ml tetrahydrofurane at −78° C. 1.25 ml (14.4 mmol) bromium acetylbromide was added all at once. It was stirred for 30 min at −78° C. and heated to room temperature. In the glove box, 2.03 g (15.8 mmol) 2,2-dimethyl-3-oxopentanal, 4.42 g (36.0 mmol) CrCl$_2$ and 193 mg (1.44 mmol) LiI were added. After reacting for eight hours at 20° C., 20 ml saturated NaCl solution was added, and the dark green, double-phase system was stirred for 15 min. The organic phase was separated, and the aqueous phase was extracted three times with diethylether. The combined organic phases were washed three times with demin. water and once with saturated NaCl solution, dried over MgSO$_4$, filtered, and vacuum concentrated. The product was purified by silica gel chromatography with acetic acid ester/petrol ether (1:1).

11. (4S)-3-[(3S)-4,4-dimethyl-1,5-dioxo-3-(tert-butyl-dimethyl-silanyloxy)]-4-benzyl-2-oxazolidinone

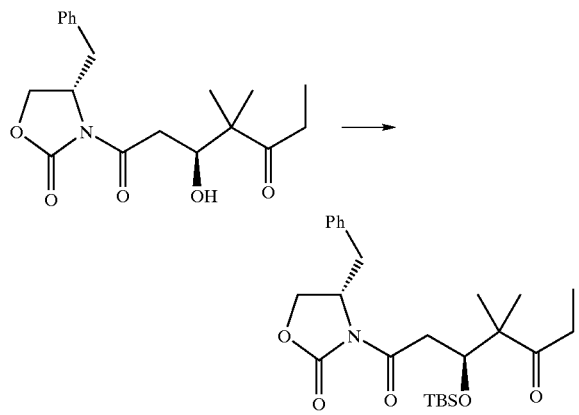

1.11 ml (9.50 mmol) freshly distilled 2,6-lutidine and 1.49 ml (6.48 mmol) (tert-butyl-dimethylsilyl)-trifluormethane sulfonate was added under argon at 0° C. to 1.50 g (4.32 mmol) (4S)-3-[(3S)-4,4-dimethyl-1,5-dioxo-3-hydroxyheptyl]-4-benzyl-2-oxazolidinone in 20 ml absolute DCM. After 2.5 hrs stirring at 0° C., 4.0 ml 2N NaOH solution was added, and diluted with 30 ml DCM. After phase separation, the organic phase was washed twice with 30 ml 2N hydrochloric acid and once with saturated NaCl solution. It was dried with $MgSO_4$, vacuum concentrated, and purified by silica gel chromatography with acetic acid ester/petrol ether (1:4).

12. (3S)-3-(tert-butyl-dimethyl-silanyloxy)-4,4-dimethyl-5-oxo-heptanoic acid

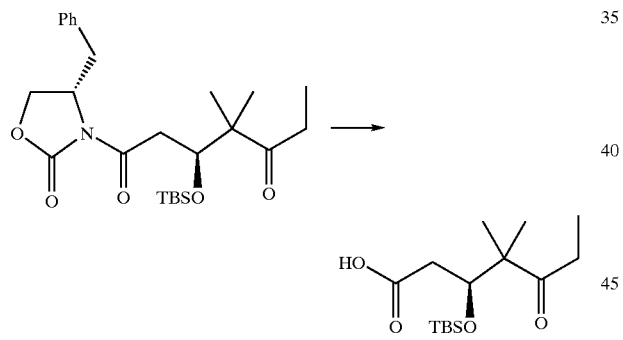

1.11 ml (9.66 mmol) hydrogen peroxide solution (30%) and 135 mg (3.22 mmol) lithium hydroxide hydrate were added to 742 mg (1.61 mmol) (4S)-3-[(3S)-4,4-dimethyl-1,5-dioxo-3-(tert-butyl-dimethyl-silyloxy)]-4-benzyl-2-oxazolidinone in 36 ml tetrahydrofurane/water (3:1) at 0° C. After stirring for one hour, 1.40 g sodium sulfite in 20 ml demin water was added. It was buffered with aqueous sodium hydrogen carbonate solution, tetrahydrofurane was removed in the vacuum, and the aqueous solution was washed three times with 5.0 ml DCM. The aqueous solution was acidified with HCl (10%) to pH 1, and extracted five times with 10 ml DCM. The organic phases were dried over $MgSO_4$, and the product was vacuum concentrated.

13. (3S)-6-bromium-3-(tert-butyl-dimethyl-silanyloxy)-4,4-dimethyl-5-oxo-heptanoic acid 152 mg (0.403 mmol) phenyl trimethyl ammonium bromide dibromide was added to a solution of 116 mg (0.383 mmol) (3S)-3-(tert-butyl-dimethyl-silanyloxy)-4,4-dimethyl-5-oxo-heptanoic acid in 3.8 ml tetrahydrofurane at 0° C. After stirring for fifteen minutes, the ice bath was removed, and stirring was performed for another hour at ambient temperature. 5.0 ml demin water was added to the resulting solution. The aqueous phase was extracted three times with 8 ml diethylether. The combined organic phases were washed with 10 ml 1N HCl solution and 10 ml saturated NaCl solution, then dried over $Na_2SO_4$, finally filtered, and vacuum concentrated. The remaining oil was purified by flash chromatography (parameters of the chromatography column: 1.0×20.0 cm, ethyl-acetate/petroleum ether=1:4 with 2% glacial acetic acid). Two fractions could be isolated. Fraction 1 contained a single diastereomer, fraction 2 was a mixture of diastereomers.

14. 6-Bromium-3-(tert-butyl-dimethyl-silanyloxy)-4,4-dimethyl-5-oxo-heptanoic acid 9-(tert-butyl-dimethyl-silanyloxy)-4,8-dimethyl-1-[1-methyl-2-(2-methyl-thiazol-4-yl)-vinyl]-non-3-enyl ester

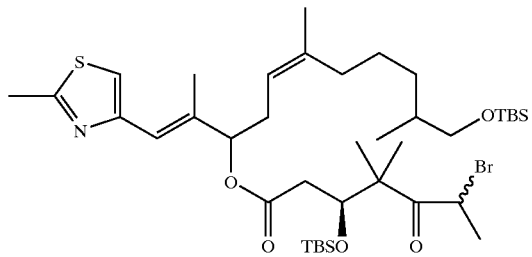

127 mg (0.291 mmol) 11-(tert-butyl-dimethyl-silanyloxy)-2,6,10-trimethyl-1-(2-methyl-thiazol-4-yl)-undeca-1,5-dien-3-ole, 115 mg (0.291 mmol) (3S)-6-bromium-3-(tert-butyl-dimethyl-silanyloxy)-4,4-dimethyl-5-oxo-heptanoic acid and 7 mg (0.058 mmol) DMAP were dissolved in 1.60 ml absolute DCM and cooled to 0° C. 73 mg (0.378 mmol) EDCI were added under stirring at 0° C. After stirring for 10 min, the ice bath was removed, and stirring was performed for 18 hrs at ambient temperature. The solvent was vacuum removed, and the product was purified by flash chromatography (parameters of the chromatography column: 2.0×20.0 cm, ethylacetate/petroleum ether=1:4).

15. 6-Bromium-3-(tert-butyl-dimethyl-silanyloxy)-4,4-dimethyl-5-oxo-heptanoic acid 9-hydroxy-4,8-dimethyl-1-[1-methyl-2-(2-methyl-thiazol-4-yl)-vinyl]-non-3-enyl ester

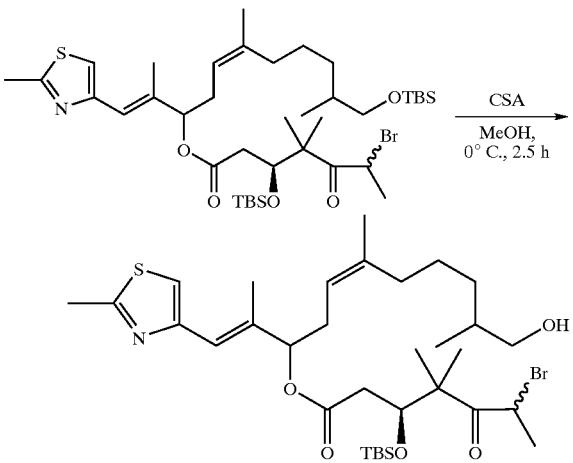

162 mg (0.202 mmol) 6-bromium-3-(tert-butyl-dimethyl-silanyloxy)-4,4-dimethyl-5-oxo-heptanoic acid 9-(tert-butyl-dimethyl-silanyloxy)-4,8-dimethyl-1-[1-methyl-2-(2- methyl-thiazol-4-yl)-vinyl]-non-3-enyl ester was dissolved in 6.0 ml of a 1:1 mixture of DCM and MeOH and cooled to 0° C. After addition of 47 mg (0.202 mmol) CSA, the solution was stirred for 2.5 hrs at 0° C. After addition of 42 μl (31 mg, 0.303 mmol) triethylamine, the solvents were vacuum removed and the remaining product was purified by flash chromatography (parameters of the chromatography column: 2.0×20.0 cm, ethyl-acetate/petroleum ether=1:2).

16. 6-Bromium-3-(tert-butyl-dimethyl-silanyloxy)-4,4-dimethyl-5-oxo-heptanoic acid 4,8-dimethyl-1-[1-methyl-2-(2-methyl-thiazol-4-yl)-vinyl]-9-oxo-non-3-enyl ester

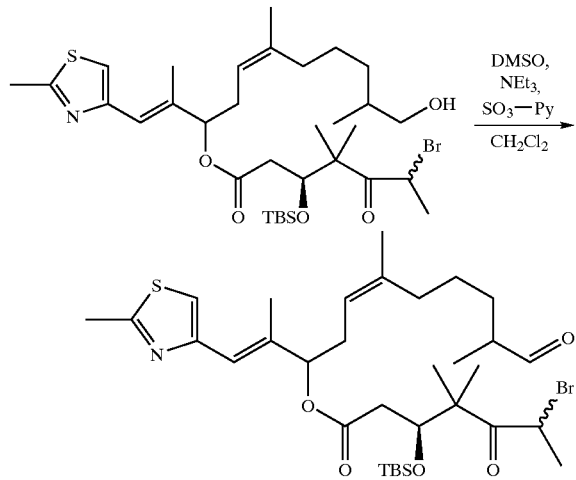

119 mg (0.173 mmol) 6-bromium-3-(tert-butyl-dimethyl-silanyloxy)-4,4-dimethyl-5-oxo-heptanoic acid 9-hydroxy-4,8-dimethyl-1-[1-methyl-2-(2-methyl-thiazol-4-yl)-vinyl]-non-3-enyl ester was dissolved in 2.10 ml DCM and 700 μl DMSO and cooled to 0° C. Then, 120 μl (885 mg, 0.865 mmol) triethylamine was added under stirring. After addition of 110 mg (0.692 mmol) $SO_3$-pyridine complex it was stirred for 40 min at 0° C. It was then diluted with 30 ml ethylacetate, and washed twice with 10 ml demin. water and once with 10 ml saturated NaCl solution. The organic phase was dried over $Na_2SO_4$, filtered subsequently and vacuum concentrated. The remaining product was not treated further, and could be used directly in the following reaction step.

17. 4-(Tert-butyl-dimethyl-silanyloxy)-8-hydroxy-5,5,7,9,13-pentamethyl-16-[1-methyl-2-(2-methyl-thiazol-4-yl)-vinyl]-oxacyclohexadec-13-ene-2,6-dione [═3-O-(tert-butyl-dimethyl-silanyl)-epothilone D]

A solution of 80 mg (0.117 mmol) 6-bromo-3-(tert-butyl-dimethyl-silanyloxy)-4,4-dimethyl-5-oxo-heptanoic acid 4,8-dimethyl-1-[1-methyl-2-(2-methyl-thiazol-4-yl)-vinyl]-9-oxo-non-3-enyl ester in 5.0 ml absolute tetrahydrofurane was added to a suspension of 35 mg (0.285 mmol) $CrCl_2$ and 30 mg (0.224 mmol) LiI in 25 ml dry tetrahydrofurane within 80 min using a syringe pump. After addition was completed, the resulting suspension was stirred for another 2 hrs at ambient temperature. Then, 20 ml semiconcentrated $NH_4Cl$ solution was added, and the organic phase was extracted with diethylether (5×15 ml). The organic phases were combined, and washed twice with 15 ml demin. water as well as twice with 15 ml saturated NaCl solution, dried over $Na_2SO_4$, filtered, and concentrated in vacuo. This gave 67 mg of a yellow oil.

This oil contained various 6,7,8,15-stereoisomeric macrocycles, of which three could be isolated as follows. Flash chromatography (parameters of the chromatography column: 1.0×20.0 cm, dieethylether/petroleum ether=1:2) allowed for the isolation of several fractions, which could be separated further by preparative HPCL on an Econosil C18/10μ 10×250 mm solumn under isocratic conditions with 85% MeCN, 15% water (containing 1% formic acid) at 5.0 ml/min, and which provided, among others, the following three 3-TBS-protected epothilone diastereomers.

17.1. Diastereomer A

| Yield | 4 mg (0.0066 mmol, 6%) colorless oil | |
|---|---|---|
| $R_f$ value | 0.30 | |
| Retention time | 42.5 to 63 min | |
| HRMS: | calculated for $C_{33}H_{56}NO_5SSi$ (MH+): | 606.3648 |
| | Found: | 606.3650 |
| $[\alpha]_D^{22} =$ | −5.4° | |
| $C_{33}H_{55}NO_5SSi$ | (605.95) | |

17.2. Diastereomer B

| Yield | 7 mg (0.0116 mmol, 10%) colorless oil | |
|---|---|---|
| $R_f$ value | 0.15 and 0.18 | |
| Retention time | 24 to 36 min | |
| HRMS: | calculated for $C_{33}H_{56}NO_5SSi$ (MH+): | 606.3648 |
| | Found: | 606.3663 |
| $[\alpha]_D^{22} =$ | +4.89° | |
| $C_{33}H_{55}NO_5SSi$ | (605.95) | |

17.3. Diastereomer C

| Yield | 2 mg (0.0033 mmol, 3%) colorless oil |
|---|---|
| $R_f$ value | 0.09 |
| Retention time | 37.5 to 54.0 min |
| $[\alpha]_D^{22} =$ | +14.6° |
| $C_{33}H_{55}NO_5SSi$ | (605.95) |

18. 3-Acetoxy-11-(tetrahydro-pyran-2-yloxy)-6,10-dimethyl-5-undecen-2-one

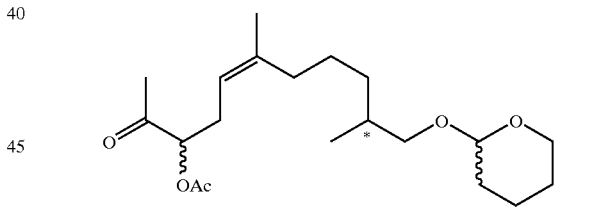

324 mg (1.20 mmol) of a raw product of 3-acetoxy-11-hydroxy-6,10-dimethyl-5-undecen-2-one and 219 μl (202 mg, 2.40 mmol) dihydropyrane was dissolved in 8.5 ml DCM. After addition of 30 mg (0.12 mmol) pyridinium paratoluene sulfonate, the reaction mixture was stirred for 18 hrs at ambient temperature. Then, 25 ml diethylether was added, the resulting organic phase was washed once with 25 ml semiconcentrated NaCl solution, and dried over $Na_2SO_4$. After filtration and removal of the solvent in vacuo, the remaining product was purified by flash chromatography (parameters of the chromatography column: 2.0×20.0 cm, ethylacetate/petroleum ether=1:4) on silica gel.

19. Acetic acid 4,8-dimethyl-1-[1-methyl-2-(2-methyl-thiazol-4-yl)-vinyl]-9-(tetrahydro-pyran-2-yloxy)-non-3-enyl ester A solution of 200 mg (0.57 mmol) 2-methyl-4-(methyl-tributylphosphoniumbromide)-1,3-thiazole in 5.0 ml abs. THF was cooled to −63° C., and 286 μl (0.57 mmol) of a 2.0 M solution of sodium hexamethyldisilazide was added dropwise. After stirring for 15 min, a solution of 167 mg (0.48 mmol) 3-acetoxy-11-(2-tetrahydropyranyloxy)-6,10-dimethyl-5-undecen-2-one in 2.0 ml THF was slowly added dropwise. After stirring for fifteen minutes at −63° C., the solution was heated to 55° C., and stirred for another hour. Then, the heating bath was removed, and 10 ml saturated $NH_4Cl$ was added. Threefold extraction with 10 ml ether, washing of the combined ether phases with demin. water (3×10 ml) and with saturated NaCl solution (1×10 ml), drying over $Na_2SO_4$, filtration, and removal of the solvent in vacuo gave a product which was purified by flash chromatography (parameters of the chromatography column: 2.0× 20.0 cm, ethylacetate/petroleum ether=1:4) on silica gel.

20. Acetic acid 9-hydroxy-4,8-dimethyl-1-[1-methyl-2-(2-methyl-thiazol-4-yl)-vinyl]-non-3-enyl ester A solution of 238 mg (0.53 mmol) acetic acid 4,8-dimethyl-1-[1-methyl-2-(2-methyl-thiazol-4-yl)-vinyl]-9-(tetrahydro-pyran-2-yloxy)-non-3-enyl ester and 13 mg (0.053 mmol) pyridinium paratoluene sulfonate in 5.0 ml 96% ethanol was stirred for eight hours at 55° C. After vacuum concentration, the residue was taken up in 25 ml diethylether. The organic phase was washed with 5% $NaHCO_3$ (2×10 ml) and with concentrated NaCl solution (1×10 l), then dried over $Na_2SO_4$, finally filtered, and vacuum concentrated. The resulting product was purified by flash chromatography (parameters of the chromatography column: 2.0×20.0 cm, ethylacetate/petroleum ether=1:2) on silica gel.

21. Acetic acid 4,8-dimethyl-1-[1-methyl-2-(2-methyl-thiazol-4-yl)-vinyl]-9-oxo-non-3-enyl ester

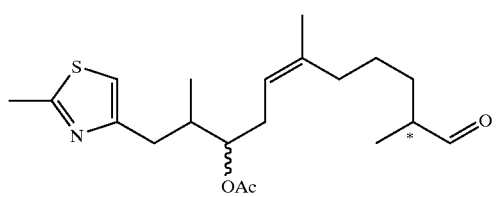

26 μl (38 mg, 0.30 mmol) oxalylchloride was dissolved in 2.0 ml abs. DCM and cooled to −63° C. After adding a solution of 42 μl (46 mg, 0.59 mmol) abs. DMSO in 0.5 ml abs. DCM, it was stirred for 10 min at −63° C., and a solution of 99 mg (0.27 mmol) acetic acid 9-hydroxy-4,8-dimethyl-1-[1-methyl-2-(2-methyl-thiazol-4-yl)-vinyl]-non-3-enyl ester in 1.0 ml abs. DCM was slowly added dropwise. After stirring for thirty minutes at −68° C., 187 μl (137 mg, 1.35 mmol) triethylamine was added. Finally, it was allowed to thaw at ambient temperature, and was stirred for one hour at this temperature.

After adding 5.0 ml water, the phases were separated, and the aqueous phase was extracted twice with 5.0 ml DCM. The combined organic phases were washed with saturated $NH_4Cl$ solution (2×4.5 ml), with water (1×4.5 ml), and with concentrated NaCl solution (1×4.5 ml). After drying over $Na_2SO_4$, filtration and vacuum concentration, the resulting product was purified by flash chromatography (parameters of the chromatography column: 2.0×20.0 cm, ethylacetate/ petroleum ether=1:2) on silica gel.

22. Acetic acid 1-acetyl-9-hydroxy-13,13-dimethoxy-4,8,10,12,12-pentamethyl-11-oxo-tridec-3-enyl ester

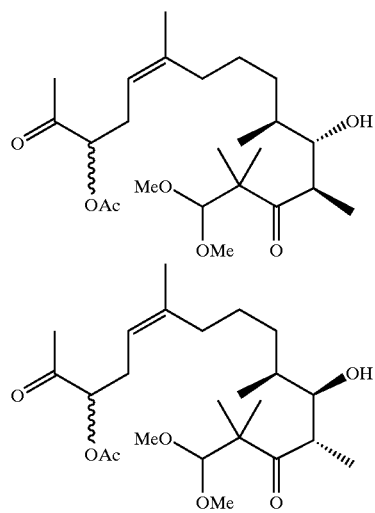

107 mg (0.86 mmol) $CrCl_2$ and 54 mg (0.4 mmol) LiI were suspended in 1.0 ml abs. THF, and then a solution of 103 mg (0.38 mmol) acetic acid 1-acetyl-4,8-dimethyl-9-oxo-non-3-enyl ester in 1.0 ml abs. THF was added. Then, 102 mg (0.40 mmol) 4-bromo-1,1-dimethoxy-2,2-dimethyl-pentan-3-one was added at once. After stirring for three hours at ambient temperature, 2.0 ml oxygen-free, saturated NaCl solution was added, and the aqueous phase was extracted five times with 2.0 ml of a 5:1 diethylether/pentane mixture. The combined organic phases were washed three times with 2.0 ml saturated $NH_4Cl$ solution and dried over $Na_2SO_4$, filtered and concentrated. The remaining product was purified by flash chromatography (parameters of the chromatography column: 2.0×20.0 cm, ethylacetate/ petroleum ether=1:1) on silica gel. Two diastereomers were obtained.

| | syn/anti - diastereomer |
|---|---|
| Yield: | 97 mg (0.22 mmol, 58%) colorless oil |
| | syn/syn - diastereomer |
| Yield: | 58 mg (0.13 mmol, 35%) colorless oil |

Example 3

The following example compounds are produced according to methods as described in Example 1 or 2 or in the description (standard reactions are described in R. C. Larock, Comprehensive Organic Transformations, VCH, 1989, ISBN: 0-89573-710-8).

(1E,5Z)-1-(2-Methylthiazol-4-yl)-3-acetoxy-2,6,10-trimethyl-undeca-1,5,9-triene

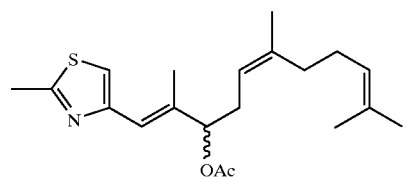

93 mg (0.27 mmol, 67%).
$C_{20}H_{29}NO_2S$ (347.52).
(4E)-2-Acetoxy-2-acetyl-5,9-dimethyl-deca-4,8-diensäure-tert-butylester

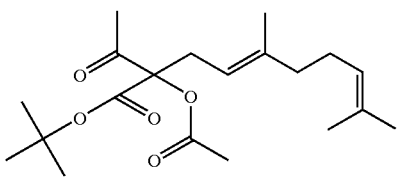

Yield: 17.6 g (50 mmol, quant.).

MS (EI): m/z (%)=352 (0.01, M+), 296, 236, 193, 167, 153, 69, 57, 43 (100.0).

$C_{20}H_{32}O_5$ (352.47).

(5E)-3-Acetoxy-6,10-dimethyl-undeca-5,9-dien-2-one

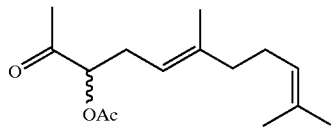

Yield: 11.66 g (46 mmol, 92%).

MS (ESI-MS): m/z (%)=253.0 (100) $[M+H]^+$, 209 (42) $[M-COCH_3]^+$, 193 (23) $[M+H—AcOH]^+$.

$C_{15}H_{24}O_3$ (252.35).

(5E)-3-Acetoxy-11-hydroxy-6,10-dimethyl-undeca-5,9-dien-2-one

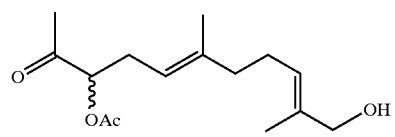

Yield: 1.63 (6.07 mmol, 27%).

$C_{15}H_{24}O_4$ (268.35).

(5E)-Acetic acid 4,8-dimethyl-1-(2-methyl-[1,3]dioxolan-2-yl)-nona-3,7-dienyl ester

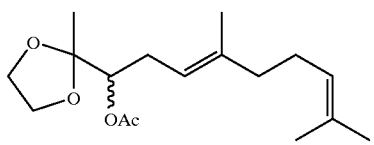

Yield: 5.78 g (19.5 mmol, 97%).

$C_{17}H_{28}O_4$ (296.40).

(5E)-Acetic acid-9-hydroxy-4,8-dimethyl-1-(2-methyl-[1,3]dioxolan-2-yl)-nona-3,7-dienyl ester

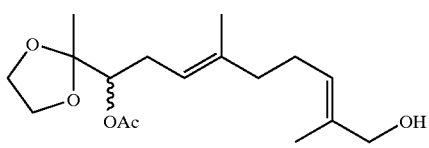

Yield: 1.59 g (5.08 mmol, 26%).

MS (ESI-MS): m/z (%)=313.0 (48) $[M+H]^+$.

$C_{17}H_{28}O_5$ (312.40).

(5E)-Acetic acid-9-hydroxy-4,8-dimethyl-1-(2-methyl-[1,3]dioxolan-2-yl)-non-3-enyl ester

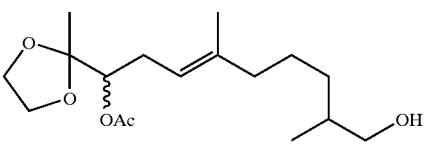

Yield: 1.185 g (3.77 mmol, 80%) colorless oil.

$C_{17}H_{30}O_5$ (314.42).

(5E)-Acetic acid-9-(4-methoxy-benzyloxy)-4,8-dimethyl-1-(2-methyl-[1,3]dioxolan-2-yl)-non-3-enyl ester

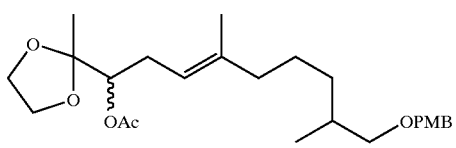

Yield: 796 mg (1.84 mmol, 68%).

MS (CI, isobut.): m/z (%) 435 (0.3) $[M+H]^+$, 375 (0.3), 313 (0.7), 253 (0.4), 241 (1.0), 193 (0.6), 163 (0.9), 121 (52), 87 (51).

$C_{25}H_{38}O_6$ (434.57).

(10S)-3-Acetoxy-11-hydroxy-6,10-dimethyl-5-undecen-2-one

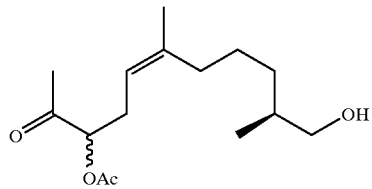

Yield: 568 mg (2.10 mmol, 75%) colorless oil.

MS (ESI-MS): m/z (%)=563.3 (100) $[2M+Na]^+$, 293.0 (54) $[M+Na]^+$, 271.1 (7) $[M+H]^+$.

$C_{15}H_{26}O_4$ (270.36).

(10S)-3-Acetoxy-11-tert-butyl-dimethylsilyloxy-6,10-dimethyl-5-undecen-2-one

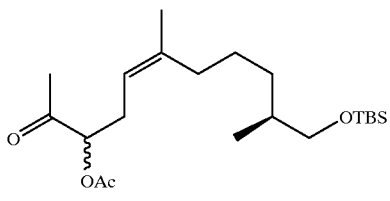

Yield 597 mg (1.55 mmol, 80%).

MS (CI, isobut.): m/z (%)=385 (13) $[M+H]^+$, 327 (13), 267 (26), 253 (6), 193 (40), 175 (62), 117 (100).

$C_{21}H_{40}O_4Si$ (384.63).

(10S)-3-Acetoxy-11-(tert-butyl-dimethyl-silanyloxy)-2,6,10-trimethyl-1-(2-methyl-thiazol-4-yl)-undeca-1,5-diene

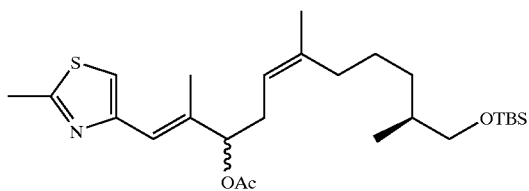

Yield: 1169 mg (2.44 mmol, 94%).
MS (CI, isobut.): m/z (%)=480 (9) [M+H]$^+$, 422 (22), 420 (51), 362 (5), 210 (>100), 178 (35), 168 (>100), 164 (72), 128 (55), 117 (65).
$C_{26}H_{45}NO_3SSi$ (479.79).
(10S)-3-Acetoxy-11-(tetrahydro-pyran-2-yloxy)-6,10-dimethyl-5-undecen-2-one

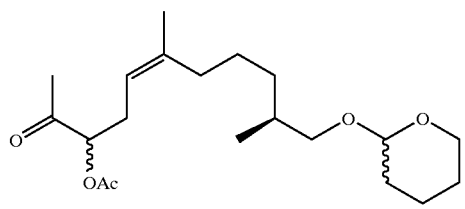

Yield: 429 mg (1.21 mmol, 64%) colorless oil.
$C_{20}H_{34}O_5$ (354,48).
(10S)-3-Acetoxy-11-(tetrahydro-pyran-2-yloxy)-2,6,10-trimethyl-1-(2-methyl-thiazol-4-yl)-undeca-1,5-diene

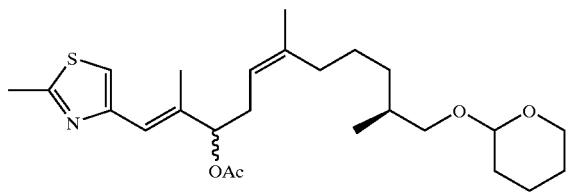

Yield: 216 mg (0.48 mmol, quant.) colorless oil.
$C_{25}H_{39}NO_4S$ (449,65).
(2E,6Z)-3,7-Dimethyl-8-(tetrahydro-pyran-2-yloxy)-octa-2,6-dien-1-ol

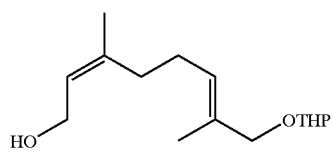

Yield: 10.27 g (40.4 mmol, 99%) yellow oil.
$C_{15}H_{26}O_3$ (254.37).
1-Chloro-3,7-Dimethyl-8-(tetrahydro-pyran-2-yloxy)-2,6-octadiene

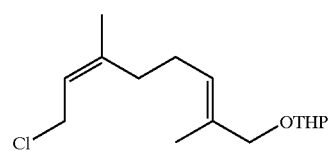

Yield: 9.80 g (36.0 mmol, quant.).
$C_{15}H_{25}ClO_2$ (272.81).
2-Acetoxy-2-acetyl-5,9-dimethyl-10-(tetrahydro-pyran-2-yloxy)-deca-4,8-dienoic acid tert-butyl ester

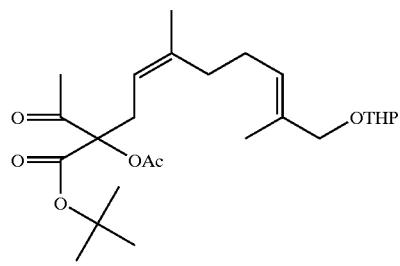

Yield: 6.67 g (14.7 mmol, 88%).
MS (ESI-MS): m/z (%)=475.3 (68) [M+Na]$^+$, 453.2 (23) [M+H]$^+$, 269.2 (80) [M+H-DHP]$^+$, 313.1 (51) [M+H—$C_4H_8$-DHP]$^+$, 295.1 (100) [M+H—$C_4H_8$-DHP-$H_2O$]$^+$.
$C_{25}H_{40}O_7$ 452,58).
11-(Tert-butyl-dimethyl-silanyloxy)-3-hydroxy-6,10-dimethyl-undec-5-en-2-one

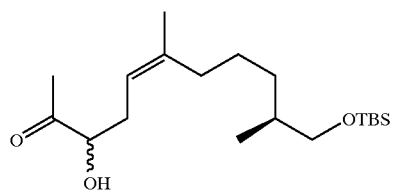

Yield: 1.686 g (4.92 mmol, 97%).
$C_{19}H_{38}O_3Si$ (342.59).
(3S)-6-Bromo-3-(tert-butyl-dimethyl-silanyloxy)-4,4-dimethyl-5-oxo-heptanoic acid-4,8-dimethyl-1-[1-methyl-2-(2-methyl-thiazol-4-yl)-vinyl]-9-oxo-non-3-enyl ester

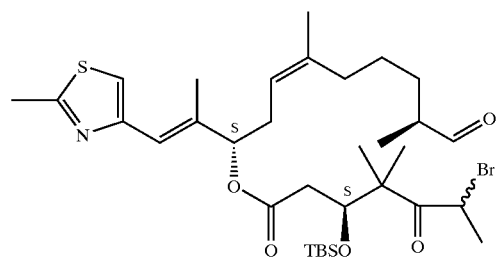

Yield: 150 mg (0.219 mmol, 84%) slightly yellowish oil.
$C_{33}H_{14}BrNO_5SSi$ (684,84).
5-Hydroxy-1,1-dimethoxy-2,2,4-trimethyl-5-phenyl-pentan-3-one

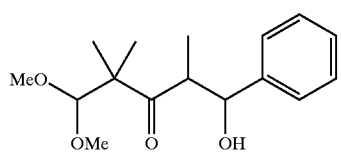

Yield: 196 mg (70%) colorless oil.
$C_{16}H_{24}O_4$ (280.36).
5-Hydroxy-1,1-dimethoxy-2,2,4,6-tetramethyl-heptan-3-one

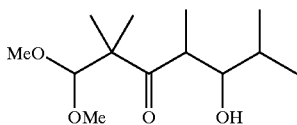

Yield: 206 mg (84%) colorless oil.

MS (EI): m/z (%)=246 (0.02, M+), 75 (100.0).

$C_{13}H_{26}O_4$ (246.347).

5-(Tert-butyl-dimethyl-silanyloxy)-1,1-dimethoxy-2,2,4,6-tetramethyl-heptan-3-one

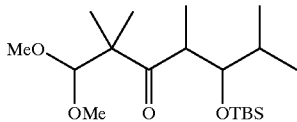

Yield: 736 mg (88%) colorless oil.

$C_{19}H_{40}O_4Si$ (360.60).

3-Acetoxy-11-hydroxy-2,6,10-trimethyl-1-(2-methyl-thiazol-4-yl)-undeca-1,5-diene

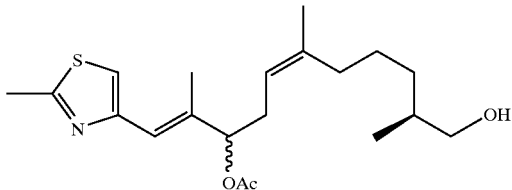

Yield: 377 mg (1.031 mmol, 97%).

MS (ESI-MS): m/z (%)=753.3 (33) [2M+Na]+, 388.1 (33) [M+Na]+, 366.1 (100) [M+H]+, 306 (28) [M+H—AcOH]+.

$C_{20}H_{31}NO_3S$ (365.53).

3-Acetoxy-2,6,10-trimethyl-1-(2-methyl-thiazol-4-yl)-11-oxo-undeca-1,5-diene

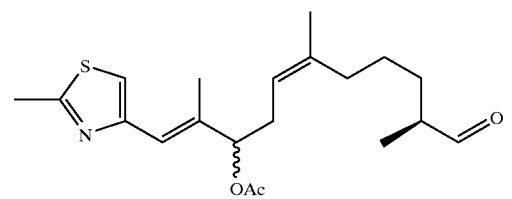

Yield: 348 mg (0.957 mmol, 93%) colorless oil.

MS (ESI-MS): m/z (%)=386.1 (48) [M+Na]+, 364.1 (100) [M+H]+, 304 (33) [M+H—AcOH]+.

$C_{20}H_{29}NO_3S$ (363,52).

1-Acetoxy-9-hydroxy-13,13-dimethoxy-4,8,10,12,12-pentamethyl-1-[1-methyl-2-(2-methyl-thiazol-4-yl)-vinyl]-11-oxo-3-tridecene

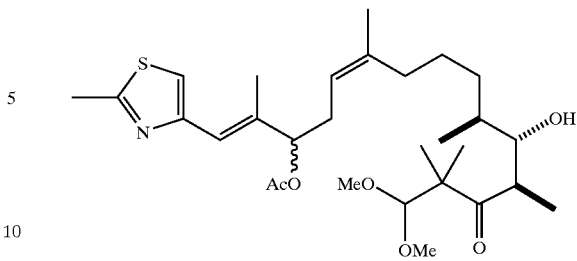

Diastereomer a

Yield: 24 mg (0.045 mmol, 32%) colorless oil.

MS (CI, isobut.): m/z (%)=538 (0.86) [M+H]+, 506 (0.55) [—OMe], 478 (1.14) [—AcOH], 446 (1.41) [—AcOH, -MeOH], 364 (0.86), 304 (1.84), 279 (2.12), 265 (3.53), 253 (8.35), 241 (2.82), 225 (3.68), 210 (11.76), 168 (30.43), 164 (21.74), 128 (100.00).

HRMS: calculated for $C_{29}H_{48}NO_6S$ (MH+): 538.32025 found: 538.322854.

$C_{29}H_{47}NO_6S$ (537.75).

Mixtures of Diastereomers a and b

Yield: 25 mg (0.046 mmol, 33%) colorless oil.

15-Acetoxy-3-(tert-butyl-dimethyl-silanyloxy)-7-hydroxy-4,4,6,8,12-pentamethyl-5,16-dioxo-heptadec-12-enoic acid methyl ester

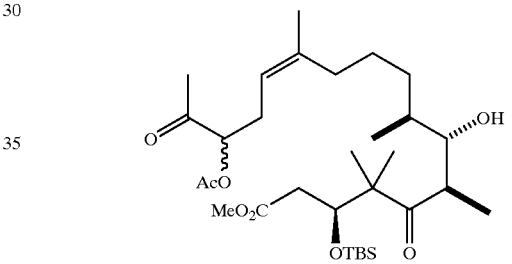

Yield: 52 mg (0.089 mmol, 64%) colorless oil.

$C_{31}H_{56}O_8Si$ (584.86).

15-Acetoxy-3-(tert-butyl-dimethyl-silanyloxy)-7-hydroxy-4,4,6,8,12,16-hexamethyl-17-(2-methyl-thiazol-4-yl)-5-oxo-heptadeca-12,16-dienoic acid methyl ester

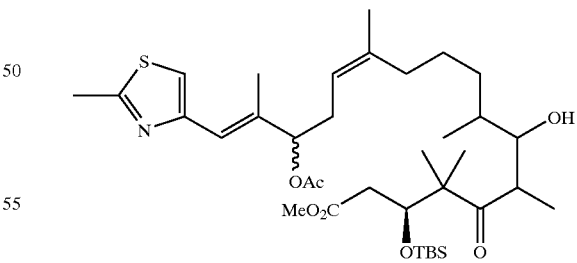

Yield: 161 mg (0.60 mmol, 60%) colorless oil.

MS (ESI-MS): m/z (%)=702.3 (100) [M+Na]+, 680.3 (28) [M+H]+, 620.3 (26) [M+H—AcOH]+.

$C_{36}H_{61}NO_7SSi$ (680,02).

15-Acetoxy-3-(tert-butyl-dimethyl-silanyloxy)-4,4,6,8,12,16-hexamethyl-17-(2-methyl-thiazol-4-yl)-5-oxo-7-triethylsilanyloxy-heptadeca-12,16-dienoic acid methyl ester

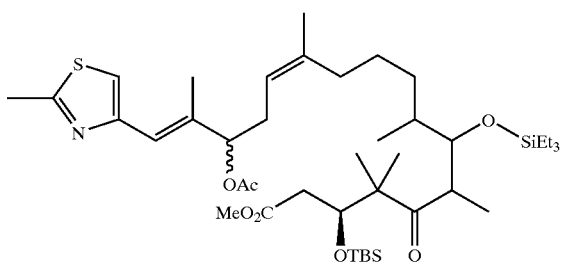

Yield: 138 mg (0.17 mmol, 100%) colorless oil.
MS (ESI-MS): m/z (%)=794.4 (100) [M+H]$^+$, 756.4 (8), 734.4 (13) [AcOH].
$C_{42}H_{75}NO_7SSi_2$ (794.28).
5-Acetoxy-pentan-4-one
Yield: 486 mg (3.4 mmol, 59%).
MS (CI): m/z (%)=43 (39), 45 (22), 57 (34), 91 (19), 119 (10), 145 (9), 173 (9), 189 (14), 190 (78), 191 (18), 233 (45), 246 (22), 251 (100), 252 (11), 307 (44).
5-Acetoxy-hexan-4-one
Yield: 2.00 g (12.6 mmol, 54%).
5-Acetoxy-heptan-4-one
Yield 415 mg (2.41 mmol, 90%).
MS (CI): m/z (%)=143 (26), 157 (11), 169 (13), 173 (100), 174 (12), 185 (18).
5-Acetoxy-octan-4-one
Yield: 1.6 g (8.59 mmol, 39%).
5-Acetoxy-nonan-4-one
Yield: 419 mg (2.10 mmol, 29%) colorless oil.
MS (CI): m/z (%)=113 (28), 142 (12), 158 (15), 171 (29), 185 (16), 201 (100), 202 (12).

Example 4
Tert-butyl-2-acetoxy-acetoacetate

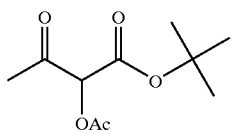

Procedure 1: A solution of acetic acid (10.6 mL, 186 mmol) in DMF (169 mL) was neutralised with triethylamine (25.8 mL, 186 mmol) at 0° C. To the resulting triethylammoniumacetate solution was added tert-butyl-2-bromo-acetoacetate (249) (40.0 g, 169 mmol) dropwise at 0° C. Then the icebath was removed and the reaction mixture stirred for two hours at room temperature. Quenching with water (280 mL) was followed by threefold extraction with ethyl acetate (3×215 mL). The organic layers were combined and washed with water (3×215 mL) and brine (1×215 mL) and dried over $Na_2SO_4$. After filtration, the solvent was removed in vacuo. The resulting oil was twice distilled at 12 mbar and 128° C. to give a colourless oil.

Yield 20.7 g (96 mmol, 57%).
Procedure 2: To a suspension sodiumacetate (30.76 g, 375 mmol) in 250 mL DMF were added 59.27 g (250 mmol) of tert-butyl-2-bromo-acetoacetate (249). After stirring at ambient temperature for 90 minutes, 415 mL demi water were added and threefold extraction with 325 mL ethyl acetate followed. The combined organic layers were washed three times with 325 mL demi water and once with 325 mL brine, then dried over $Na_2SO_4$. After filtration, the solvent was removed in vacuo. The resulting oil was purified via Kugelrohrdistillation.

Yield 36.52 g (169 mmol, 68%).
MS (CI): m/z (%)=117 (19), 143 (12), 161 (100), 205 (43), 207 (12), 217 (18).
HRMS: calculated for $C_{10}H_{17}O_5$ (MH$^+$): 217.10760 found: 217.10460.
$C_{10}H_{16}O_5$ (216.23).
(1E,5Z)-1-(2-Methylthiazol-4-yl)-3-acetoxy-2,6,10-trimethyl-undeca-1,5,9-trien

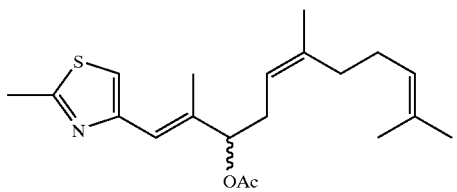

To a suspension of 19 mg (0.48 mmol) NaH (60% in mineral oil) in 2.5 mL THF were added dropwise 100 μl (77 mg, 0.48 mmol) 1,1,1,3,3,3-hexamethyl-disilazane. The resulting solution was cooled to −63° C. and a solution of 153 mg (0.44 mmol) tributyl-(2-methyl-thiazol-4-ylmethyl)-phosphonium chloride (9c) in 2.5 mL abs. THF was slowly added. Then 100 mg (0.40 mmol) of (5Z)-3-acetoxy-6,10-dimethyl-undeca-5,9-dien-2-one (251a) were added and the mixture was stirred for 30 min at −63° C. as well as another hour at 55° C.

After cooling down to ambient temperature, 10 mL saturated $NH_4Cl$ solution were added and the waterlayer was extracted three times with 10 mL diethylether. The combined organic layers were washed with demi water (3×10 mL), with brine (1×20 mL), then dried over $Na_2SO_4$, filtrated, and concentrated in vacuo. The remaining oil was purified via flash chromatography (colum dimensions: 3.0× 20.0 cm, ethyl acetate/petroleum ether=1:6).

Yield 93 mg (0.27 mmol, 67%).
$C_{20}H_{29}NO_2S$ (347.52).
(4E)-2-Acetoxy-2-acetyl-5,9-dimethyl-deca-4,8-dienonoic acid-tert-butylester

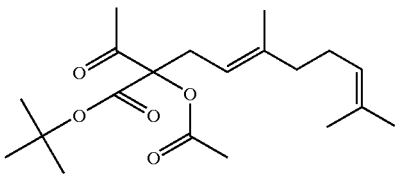

Tert-butyl-2-acetoxy-acetoacetate (10.8 g, 50 mmol) was added dropwise to a stirred suspension of NaH (2.32 g, 58 mmol, 60% suspension in mineral oil) in DMF (100 mL) at 0° C. After the liberation of hydrogen gas stopped, geranyl-bromide (220d) (10.9 g, 50 mmol) was added dropwise at 0° C. Afterwards the icebath was removed and the mixture stirred at room temperature for 16 hours. Then the mixture was diluted with ether (500 mL) and washed with water (3×200 mL) as well as with brine (1×200 mL). The solution was dried over $Na_2SO_4$, filtered and concentrated in vacuo to give a slightly yellow oil.

Yield 17.6 g (50 mmol, quant.).
MS (EI): m/z (%)=352 (0.01, M+), 296, 236, 193, 167, 153, 69, 57, 43 (100.0).
$C_{20}H_{32}O_5$ (352.47).
(5E)-3-Acetoxy-6,10-dimethyl-undeca-5,9-dien-2-one

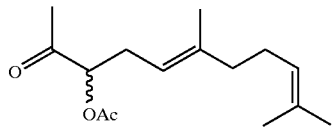

A solution of 17.62 g (50.0 mmol) (4E)-2-acetoxy-2-acetyl-5,9-dimehtyl-deca-4,8-dienoic-acid-tert-butylester (250b), 2.33 g (55.0 mmol) LiCl and 1.00 mL (55.0 mmol) demi water were stirred in 125 mL DMSO at 160° C. for six hours and 14 hours at ambient temperature. The brown solution was diluted with 400 mL demi water and the waterphase was extracted three times with 250 mL diethylether. The etherlayers were combined and washed three times with 250 mL demi water as well as once with 250 mL brine. Finally the etherlayer was dried over $Na_2SO_4$, filtrated and concentrated in vacuo to remain a redbrown oil.
Yield 11.66 g (46 mmol, 92%).
MS (ESI-MS): m/z (%)=253.0 (100) $[M+H]^+$, 209 (42) $[M-COCH_3]^+$, 193 (23) $[M+H—AcOH]^+$.
$C_{15}H_{24}O_3$ (252.35).
(5E)-3-acetoxy-11-hydroxy-6,10-dimethyl-undeca-5,9-dien-2-one

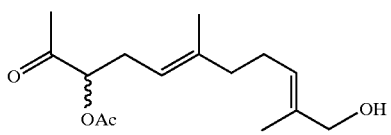

127 mg (1.14 mmol) $SeO_2$ and 8.19 g tert-butyl hydroperoxide (70% solution in water) were stirred for 30 minutes in 15.0 mL $CH_2Cl_2$. Then 5.73 g (22.7 mmol) (5E)-3-acetoxy-6,10-dimethyl-undeca-5,9-dien-2-one (251b) were added and the reaction mixture was stirred at ambient temperature for 24 hours. Then 20 mL benzene were added and all volatile matter was removed in vacuo. The remaining oil was diluted with 100 mL diethylether and was washed twice with 30 mL of 0.2N NaOH solution as well as with 30 mL brine. The organic layer was dried over $Na_2SO_4$, filtrated and concetrated in vacuo. The product was isolated via column chromatography (column dimensions: 2.0×20.0 cm, ethyl acetate/petroleum ether=1:5).
Yield 1.63 (6.07 mmol, 27%).
$C_{15}H_{24}O_4$ (268.35).
(5E)-Acetic acid 4,8-dimethyl-1-(2-methyl-[1,3]dioxolan-2-yl)-nona-3,7-dienylester

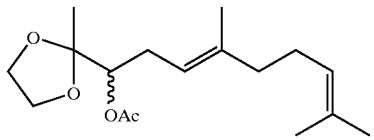

5.05 g (20.0 mmol) (5E)-3-acetoxy-6,10-dimethyl-undeca-5,9-dien-2-one (251b), 1.32 mL (1.49 g, 24.0 mmol) ethylene glycol and 0.190 mg (1.00 mmol) p-toluenesulphonic acid were heatet at a dean stark trap under reflux in 50.0 mL benzene for five hours. The benzene solution was diluted with 200 mL diethylether, washed with saturated $NaHCO_3$ solution (2×100 mL), demi water (100 mL) and brine (100 mL). The organic layer was dried over $Na_2SO_4$, filtrated and concentrated in vacuo.
Yield 5.78 g (19.5 mmol, 97%) yellow oil.
$C_{17}H_{28}O_4$ (296.40).
(5E)-Acetic acid-9-hydroxy-4,8-dimethyl-1-(2-methyl-[1,3]dioxolan-2-yl)-nona-3,7-dienyl ester

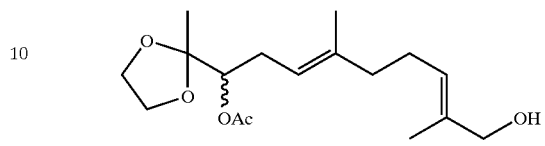

To a suspension of 108 mg (0.975 mmol) $SeO_2$ in 13 mL $CH_2Cl_2$ were added 7.03 g (54.6 mmol) of a 70% tert-butyl hydroperoxide. After stirring for 30 min at ambient temperature 5.775 g (19.5 mmol) acetic acid 4,8-dimethyl-1-(2-methyl-[1,3]dioxolan-2-yl)-nona-3,7-dienyl ester (262) were added and the resulting suspension was stirred 38 hours at ambient temperaure. After addition of 20 mL all volatile matter was removed in vacuo and the remaining oil was purified by column chromatography.
Yield 1.59 g (5.08 mmol, 26%) colourless oil.
MS (ESI-MS): m/z (%)=313.0 (48) $[M+H]^+$.
$C_{17}H_{28}O_5$ (312.40).
(5E)-Acetic acid-9-hydroxy-4,8-dimethyl-1-(2-methyl-[1,3]dioxolan-2-yl)-non-3-enyl ester

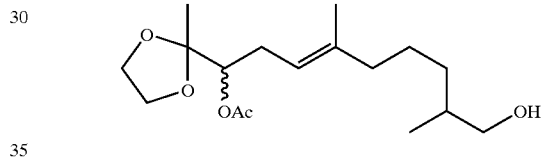

1.474 g (4.71 mmol) acetic acid 9-hydroxy-4,8-dimethyl-1-(2-methyl-[1,3]dioxolan-2-yl)-nona-3,7-dienyl ester (263) was dissolved in 15.0 mL absolute methanol and 750 μl demi water were added. The solution was degassed with three freeze-thaw-cycles before 41 mg Ru(R-BINAP)(OAc)$_2$ were added and put in an autoclave under nitrogen atmosphere together with a magnetic stirring bar. After threefold purging with hydrogen (5.0 quality) the autoclave was set under a pressure of 100 bar hydrogen (5.0 quality) and stirred at room temperature for 25 h.
The hydrogen pressure was released and the solution concentrated in vacuo. The obtained brown oil was purified by flash chromatography (column dimensions: 4.0×20.0 cm, ethyl acetate/petroleum ether=1:2).
Yield 1.185 g (3.77 mmol, 80%) colourless oil.
$C_{17}H_{30}O_5$ (314.42).
(5E)-Acetic acid-9-(4-methoxy-benzyloxy)-4,8-dimethyl-1-(2-methyl-[1,3]dioxolan-2-yl)-non-3-enyl ester

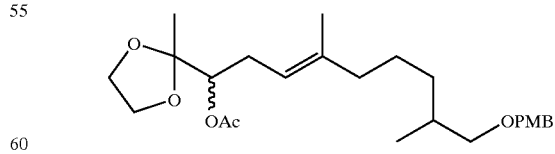

849 mg (2.700 mmol) acetic acid 9-hydroxy-4,8-dimethyl-1-(2-methyl-[1,3]dioxolan-2-yl)-non-3-enyl ester (264) were dissolved in 10.0 mL $CH_2Cl_2$ and 48 mg (0.19 mmol) PPTS as well as 1.526 g (5.400 mmol) para-methoxy benzyl trochloroimidate (268) were added and stirred 18 hours at ambient temperature. Then the solution was diluted with 25 mL diethylether and 25 mL petroleumether, washed with demi water (2×20 mL) and with brine (20 mL), dried over $Na_2SO_4$, filtrated and concentrated in vacuo. The remaining yellow oil was purified via flash chromatography (column dimensions: 3.5×20.0 cm, ethyl acetate/petroleum ether=1:4).

Yield 796 mg (1.84 mmol, 68%).

MS (CI, isobut.): m/z (%)=435 (0.3) [M+H]$^+$, 375 (0.3), 313 (0.7), 253 (0.4), 241 (1.0), 193 (0.6), 163 (0.9), 121 (52), 87 (51).

$C_{25}H_{38}O_6$ (434.57).
(10S)-3-Acetoxy-11-hydroxy-6,10-dimethyl-5-undecen-2-one 1.032 g (2.79 mmol) (9S)-(4Z)-2-acetoxy-2-acetyl-5,9-dimehtyl-10-hydroxy-deca-4-enoic-acid-tert-butylester (266) were dissolved in 28 mL $CH_2Cl_2$ and 2.80 mL TFA were added. After stirring for two hours at room temperature, all volatile matter was removed in vacuo and the reaming oil was dissolved in 28 mL methanol. Then 5.6 mL saturated $NaHCO_3$-solution was added and the suspension was stirred for 140 minutes at ambient temperature before dilution with 200 mL ether was performed. The organic layer was washed two times with 50 mL demi water as well as once with 50 mL brine. After drying over $Na_2SO_4$, filtration and removal of the solvents in vacuo, a slightly yellow oil was obtained. Purification was achieved by flash chromatography (column dimensions: 2.0×20.0 cm, ethyl acetate/petroleum ether=2:3).

Yield 568 mg (2.10 mmol, 75%) colourless oil.

MS (ESI-MS): m/z (%)=563.3 (100) [2M+Na]$^+$, 293.0 (54) [M+Na]$^+$, 271.1 (7) [M+H]$^+$.

$C_{15}H_{26}O_4$ (270.36).
(10S)-3-Acetoxy-11-tert-butyl-dimethylsilyloxy-6,10-dimethyl-5-undecen-2-one 528 mg (1.95 mmol) 3-acetoxy-11-hydroxy-6,10-dimethyl-5-undecen-2-one (11a) were dissolved in 10.0 mL absolute $CH_2Cl_2$. After addition of 541 µl (395 mg, 3.90 mmol) triethylamine and 12 mg (0.10 mmol) of DMAP, the solution was cooled with an ice bath. After stirring for five minutes 368 mg (2.44 mmol) of TBDMSCl were added at once and the resulting solution was stirred at 0° C. for two hours and additional 14 hours at room temperature. The resulting colourless suspension was again cooled to 0° C. before 460 µl of methanol were added. After stirring for 30 min at 0° C., all solvents were removed in vacuo. Then 15 mL ether as well as 15 mL saturated $NH_4Cl$-solution were added and after intensive stirring and separation, the aqueous phase was extracted twice with 10 mL ether. The combined organic layers were washed with 15 mL brine, dried over $Na_2SO_4$, filtered and concentrated in vacuo. The obtained oil was purified by means of flash chromatography (column dimensions: 2.0×20.0 cm, ethyl acetate/petroleum ether=1:10).

yield 597 mg (1.55 mmol, 80%) colourless oil.

$R_f$-value 0.32

MS (CI, isobut.): m/z (%)=385 (13) [M+H]$^+$, 327 (13), 267 (26), 253 (6), 193 (40), 175 (62), 117 (100).

HRMS: calculated for $C_{21}H_{41}O_4Si$ (MH$^+$): 385.27740 found: 385.278524.

$C_{21}H_{40}O_4Si$ (384.63).
(10S)-3-Acetoxy-11-(tert-butyl-dimethyl-silanyloxy)-2,6,10-trimethyl-1-(2-methyl-thiazol-4-yl)-undeca-1,5-diene A solution of 1092 mg (3.12 mmol) tributyl-(2-methyl-thiazol-4-ylmethyl)-phosphonium chloride (9c) in 21.0 mL abs. THF was cooled to −63° C. and 1.56 mL (3.12 mmol) of a 2.0 M solution of sodium-hexamethyldisilazid were added dropwise. After stirring for 15 min, a solution of 1000 mg (2.60 mmol) 3-acetoxy-11-tert-butyl-dimethylsilyloxy-6,10-dimethyl-5-undecen-2-one (11b) in 8.0 mL THF was added slowly. After 15 min stirring at −63° C., the solution was heated to 55° C. and stirred for an additional hour. Then the heating bath was removed and 42 mL saturated $NH_4Cl$-solution were added. Threefold extraction with 20 mL ether, washing the combined etherlayers with demi water (3×20 mL) and with brine (1×30 mL), drying over $Na_2SO_4$, filtration and removal of the solvent in vacuo gave a brown oil. Purification was achieved via flash chromatography (column dimensions: 3.5×20.0 cm, ethyl acetate/petroleum ether= 1:4).

Yield 1169 mg (2.44 mmol, 94%) colourless oil.

MS (CI, isobut.): m/z (%)=480 (9) [M+H]$^+$, 422 (22), 420 (51), 362 (5), 210 (>100), 178 (35), 168 (>100), 164 (72), 128 (55), 117 (65).

| HRMS: | calculated for $C_{26}H_{46}NO_3SSi$ (MH$^+$): | | 480.295912 | |
|---|---|---|---|---|
| | found: | | 480.29678 | |
| EA: | calculated | C 65.09 | H 9.45 | N 2.92 | S 6.68 |
| | found | C 64.79 | H 9.53 | N 2.96 | S 6.54 |

$C_{26}H_{45}NO_3SSi$ (479.79).
(10S)-3-Acetoxy-11-(tetrahydro-pyran-2-yloxy)-6,10-dimethyl-5-undecen-2-one Procedure 1: 324 mg (1.20 mmol) of a crude product of 3-acetoxy-11-hydroxy-6,10-dimethyl-5-undecen-2-one (11a) and 219 µl (202 mg, 2.40 mmol) dihydropyrane were dissolved in 8.5 mL CH₂Cl₂. After addition of 30 mg (0.12 mmol) pyridinium paratoluenesulphonate, the solution was stirred at ambient temperature for 18 hours. Then 25 mL diethylether were added, the organic layer washed once with 25 mL half concentrated NaCl-solution and dried over Na₂SO₄. After filtration and evaporation of the solvents in vacuo, the remaining oil was purified by flash chromatography (column dimensions: 2.0×20.0 cm, ethyl acetate/petroleum ether=1:4).

Yield 176 mg (0.50 mmol, 41%) colourless oil.

Procedure 2: 508 mg (1.88 mmol) of 3-acetoxy-11-hydroxy-6,10-dimethyl-5-undecen-2-one (11a) and 344 µl (320 mg, 3.80 mmol) dihydropyrane were dissolved in 5.0 mL CH₂Cl₂. After addition of 165 mg (1.90 mmol) LiBr the mixture was stirred four hours at ambient temperature. After addition of 20.0 mL diethylether, the organic layer was washed once with 5.0 mL water and once with 5.0 mL brine. The organic layer was dried over Na₂SO₄, filtrated and concentrated in vacuo and the remaining oil was purified via flash chromatography (column dimensions: 2.0×20.0 cm, ethyl acetate/petroleum ether=1:4).

Yield 429 mg (1.21 mmol, 64%) colourless oil.

C₂₀H₃₄O₅ (354,48).

(10S)-3-Acetoxy-11-(tetrahydro-pyran-2-yloxy)-2,6,10-trimethyl-1-(2-methyl-thiazol-4-yl)-undeca-1,5-diene

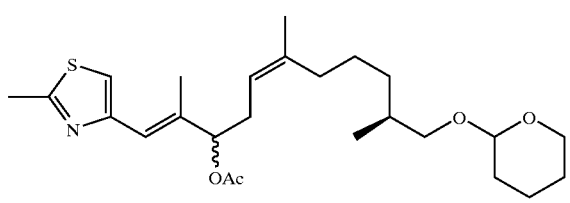

A solution of 200 mg (0.57 mmol) tributyl-(2-methyl-thiazol-4-ylmethyl)-phosphonium chloride (9c) in 5.0 mL abs. THF was cooled to −63° C. and 286 µl (0.57 mmol) of a 2.0 M solution of sodium-hexamethyldisilazid were added dropwise. After stirring for 15 min, a solution of 167 mg (0.48 mmol) 3-acetoxy-11-(2-tetrahydropyranyloxy)-6,10-dimethyl-5-undecen-2-one (11c) in 2.0 mL THF was added slowly. After 15 min stirring at −63° C., the solution was heated to 55° C. and stirred for an additional hour. Then the heating bath was removed and 10 mL saturated NH₄Cl-solution were added. Three-fold extraction with 10 mL ether, washing the combined etherlayers with demi water (3×10 mL) and with brine (1×10 mL), drying over Na₂SO₄, filtration and removal of the solvent in vacuo gave a brown oil. Purification was achieved via flash chromatography (column dimensions: 2.0×20.0 cm, ethyl acetate/petroleum ether= 1:4).

Yield 216 mg (0.48 mmol, quant.) colourless oil.

C₂₅H₃₉NO₄S (449,65).

(2E,6Z)-3,7-Dimethyl-8-(tetrahydro-pyran-2-yloxy)-octa-2,6-dien-1-ol

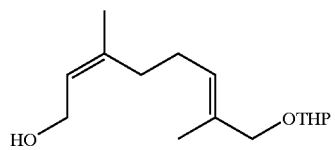

8.66 g (40.8 mmol) 1-acetoxy-8-hydroxy-3,7-dimethyl-octa-2,6-dien (257a) and 7.44 mL (6.86 g, 81.6 mmol) DHP were dissolved in 20 mL CH₂Cl₂. After addition of 513 mg (2.04 mmol) PPTS, the mixture was stirred seven hours at ambient temperature. After removal of all volatile matter in vacuo, the obtained oil was dissolved in 200 mL methanol and 14.96 g (151 mmol) K₂CO₃ were added and the suspension was stirred at ambient temperature for one hour. After addition of 500 mL demi water, fivefold extraction with 150 mL diethylether was performed. The organic layers were combined and washed with demi water (2×100 mL) as well as brine (1×100 mL), dried over Na₂SO₄, filtrated and concentrated in vacuo.

Yield 10.27 g (40.4 mmol, 99%) yellow oil.

C₁₅H₂₆O₃ (254.37).

1-Chloro-3,7-Dimethyl-8-(tetrahydro-pyran-2-yloxy)-2,6-octadiene

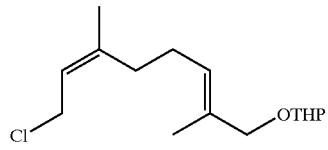

In a dry 500 mL Schlenk flask, 5.29 g (39.6 mmol) NCS is were dissolved in 185 mL dry CH₂Cl₂ and the solution was then cooled to −5° C. before 3.17 mL (2.68 g, 43.2 mmol) dimethylsulfide were added dropwise. After stirring for five minutes at −5° C., the resulting white suspension was cooled to −63° C. and 9.16 g (36.0 mmol) 3,7-dimethyl-8-(tetrahydro-pyran-2-yloxy)-octa-2,6-dien-1-ol (271) were added dropwise. After the addition was complete, the reaction mixture was allowed to reach −5° C. again and was stirred one hour at that temperature in which the white suspension turned slowly into a colourless solution. Then 90 mL saturated ammoniumchloride solution were added, the layers separated and the aqueous layer extracted twice with 75 mL diethylether. The organic layers were combined and washed twice with 75 mL brine, then dried over Na₂SO₄, filtered and concentrated in vacuo. A slightly yellow oil was obtained in high purity.

Yield 9.80 g (36.0 mmol, quant.).

C₁₅H₂₅ClO₂ (272.81).

2-Acetoxy-2-acetyl-5,9-dimethyl-10-(tetrahydro-pyran-2-yloxy)-deca-4,8-dienoic acid tert-butyl ester

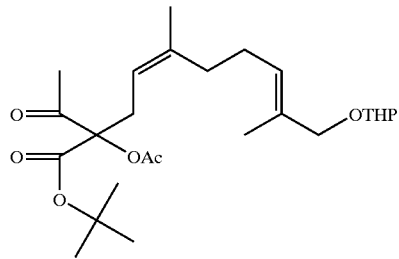

Tert-butyl-2-acetoxy-acetoacetate (219a) (3.80 g, 17.6 mmol) was added dropwise to a stirred suspension of NaH (60% suspension in mineral oil, 0.870 g, 21.8 mmol) in DMF (35 mL) at 0° C. After the liberation of hydrogen gas stopped, 1-chloro-3,7-dimethyl-8-(tetrahydro-pyran-2-yloxy)-2,6-octadiene (272) (4.57 g, 16.7 mmol) was added dropwise at 0° C. After stirring for one hour at 0° C. the icebath was removed and the mixture stirred at room temperature for three hours. Then the mixture was diluted with ether (225 mL) and washed with water (3×75 mL) as well as with brine (1×75 mL). The solution was dried over Na₂SO₄, filtered and concentrated in vacuo, to give a slightly yellow oil.

Yield 6.67 g (14.7 mmol, 88%).

MS (ESI-MS): m/z (%)=475.3 (68) [M+Na]⁺, 453.2 (23) [M+H]⁺, 269.2 (80) [M+H-DHP]⁺, 313.1 (51) [M+H—C₄H₈-DHP]⁺, 295.1 (100) [M+H—C₄H₈-DHP-H₂O]⁺.

C₂₅H₄₀O₇ (452,58).

11-(Tert-butyl-dimethyl-silanyloxy)-3-hydroxy-6,10-dimethyl-undec-5-en-2-one

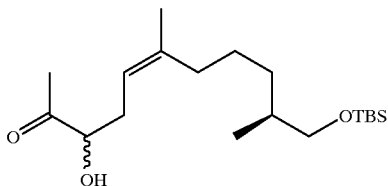

1.943 g (5.05 mmol) 3-acetoxy-11-(tert-butyl-dimethylsilyloxy)-6,10-dimethyl-5-undecen-2-one (11b) were dissolved in 20.0 mL methanol and 400 μl of a saturated potassium carbonate solution were added. After stirring at ambient temperature for 14 minutes, 30 mL brine were added and fivefold extraction with 30 mL diethylether followed. (The hydrolysis actually was already complete after five minutes according to TLC. Workup right on time is crucial, for the yield drop drastically if the reaction is not stopped in time. Stirring for example for ninety minutes resulted in dramatic drop of the yield to 43%!!!). The combined organic layers were washed with 50 mL brine and dried over Na₂SO₄. After filtration and removal of the solvent in vacuo, the remaining oil was purified via flash chromatography (column dimensions: 2.0×20.0 cm, ethyl acetate/petroleum ether=1:4).

| Yield | 1.686 g (4.92 mmol, 97%) |
|---|---|
| C₁₉H₃₈O₃Si | (342.59) |

(3S)-6-Bromo-3-(tert-butyl-dimethyl-silanyloxy)-4,4-dimethyl-5-oxo-heptanoic acid-4,8-dimethyl-1-[1-methyl-2-(2-methyl-thiazol-4-yl)-vinyl]-9-oxo-non-3-enyl ester

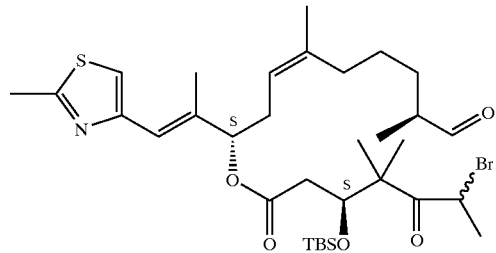

180 mg (0.262 mmol) (3S)-6-bromo-3-(tert-butyl-dimethyl-silanyloxy)-4,4-dimethyl-5-oxo-heptanoic acid 9-hydroxy-4,8-dimethyl-1-[1-methyl-2-(2-methyl-thiazol-4-yl)-vinyl]-non-3-enyl ester (277b) were dissolved in 5.30 mL CH₂Cl₂ and 1.72 mL DMSO at 0° C. and 212 μl (155 mg, 1.53 mmol) triethylamine were added. After addition of 195 mg (1.223 mmol) SO₃.Pyridine—complex the mixture was stirred 60 min at 0° C. Dilution with 40 mL diethylether was followed by twofold washing with 10 mL demi water and with brine (2×10 mL). The organic layer was the dried over Na₂SO₄, filtered and concentrated in vacuo to give a slightly yellow oil which was used in the following reaction step without further purification.

| Yield | 150 mg (0.219 mmol, 84%) slightly yellow oil |
|---|---|
| C₃₃H₅₄BrNO₅SSi | (684.84) |

Macrolacton Strategy

5-Hydroxy-1,1-dimethoxy-2,2,4-trimethyl-5-phenyl-pentan-3-one

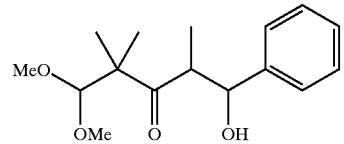

To a solution of 298 mg (2.42 mmol) CrCl₂ and 20 mg (0.15 mmol) LiI in 6.0 mL abs. THF were added 117 μl (1.1 mmol) benzaldehyde and 253 mg (1.0 mmol) 4-bromo-1,1-dimethoxy-2,2-dimethyl-pentan-3-one (225). After stirring at ambient temperature for 30 minutes the brown solution was quenched with 5.0 mL brine. The aqueous phase was extracted three times with 5.0 mL diethylether. The organic layers were combined, washed with conc. NH₄C, solution (2×5.0 mL), dried over MgSO₄, filtrated and concentrated in vacuo. The remaining green oil (196 mg) was purified via flash chromatography (column dimensions: 3.5×20.0 cm, ethyl acetate/petroleum ether=1:6).

| Yield: | 196 mg (70%) colourless oil |
|---|---|
| C₁₆H₂₄O₄ | (280.36) |

5-Hydroxy-1,1-dimethoxy-2,2,4,6-tetramethyl-heptan-3-one

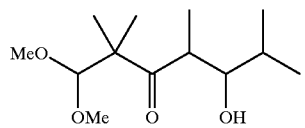

To a solution of 298 mg (2.42 mmol) CrCl₂ and 29 mg (0.22 mmol) LiI in 6.0 mL abs. THF were added 100 μl (1.1 mmol) isobutyric aldehyde and 253 mg (1.0 mmol) 4-bromo-1,1-dimethoxy-2,2-dimethyl-pentan-3-one (225). After stirring at ambient temperature for one hour the brown solution was quenched with 5.0 mL brine. The aqueous phase was extracted three times with 5.0 mL of a diethylether-pentane mixture (5:1). The organic layers were combined, washed with conc. NH₄Cl solution (3×5.0 mL), dried over MgSO₄, filtrated and concentrated in vacuo. The remaining colourless oil (206 mg) was purified via flash chromatography (column dimensions: 3.5×20.0 cm, ethyl acetate/petroleum ether=1:8).

Yield: 206 mg (84%) colourless oil.

MS (EI): m/z (%)=246 (0.02, M⁺), 75 (100.0).

C₁₃H₂₆O₄ (246.347).

5-(Tert-butyl-dimethyl-silanyloxy)-1,1-dimethoxy-2,2,4,6-tetramethyl-heptan-3-one

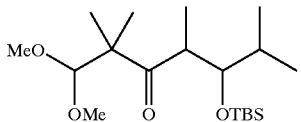

To a solution of 571 mg (2.31 mmol) 5-hydroxy-1,1-dimethoxy-2,2,4,6-tetramethyl-heptan-3-one (281) and 539 μl (4.63 mmol) 2,6-lutidine in 2.3 mL CH$_2$Cl$_2$ at 0° C. were added 797 μl (3.47 mmol) tert-butyl-dimethylsilyltriflate dropwise. After two hours stirring at 0° C., 2.0 mL 0.2N NaOH solution was added and the mixture stirred ten minutes at ambient temperature. After addition of 30 mL CH$_2$Cl$_2$, the organic layer was washed twice with 0.2N HCl solution as well as twice with 30 mL brine. The organic layer was dried over MgSO$_4$, filtrated and concentrated in vacuo. The obtained yellow oil was purified by flash chromatography (column dimensions: 3.5×20.0 cm, ethyl acetate/petroleum ether=1:10).

yield: 736 mg (88%) colourless oil.

R$_f$-value 0.53 (acetic ether/petroleum ether, V:V=1:10).

C$_{19}$H$_{40}$O$_4$Si (360.60).

3-Acetoxy-11-hydroxy-2,6,10-trimethyl-1-(2-methyl-thiazol-4-yl)-undeca-1,5-diene

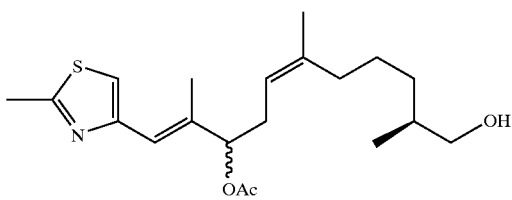

Procedure 1 (from THP-ether): A solution of 238 mg (0.53 mmol) 3-acetoxy-11-(tetrahydro-pyran-2-yloxy)-2,6,10-trimethyl-1-(2-methyl-thiazol-4-yl)-undeca-1,5-diene (270b) and 13 mg (0.053 mmol) pyridinium paratoluenesulphonate in 5.0 mL 96% ethanol was stirred at 55° C. for eight hours. After concentration in vacuo, the residue was dissolved in 25 mL diethylether. The organic layer was washed with 5% NaHCO$_3$ (2×10 mL) and with brine (1×10 l), then dried over Na$_2$SO$_4$, filtrated and concentrated in vacuo. The remaining oil was purified via flash chromatography (column dimensions: 2.0×20.0 cm, ethyl acetate/petroleum ether=1:2).

Yield 99 mg (0.27 mmol, 51%) colourless oil.

Procedure 2 (from TBS-ether): 512 mg (1.067 mmol) 3-acetoxy-11-(tert-butyl-dimethyl-silanyloxy)-2,6,10-trimethyl-1-(2-methyl-thiazol-4-yl)-undeca-1,5-diene (270a) were dissolved in 15.0 mL CH$_2$Cl$_2$ and 15.0 mL MeOH and cooled to 0° C. After addition of 248 mg (1.067 mmol) CSA the solution was stirred for 4.0 hours at 0° C. Then 222 μl (162 mg, 1.601 mmol) triethylamine were added, the solvents removed in vacuo and the remaining oil was purified by flash chromatography (column dimensions: 2.0×20.0 cm, ethyl acetate/petroleum ether=1:1).

Yield 377 mg (1.031 mmol, 97%).

MS (ESI-MS): m/z (%)=753.3 (33) [2M+Na]$^+$, 388.1 (33) [M+Na]$^+$, 366.1 (100) [M+H]$^+$, 306 (28) [M+H—AcOH]$^+$.

C$_{20}$H$_{31}$NO$_3$S (365.53).

3-Acetoxy-2,6,10-trimethyl-1-(2-methyl-thiazol-4-yl)-11-oxo-undeca-1,5-diene

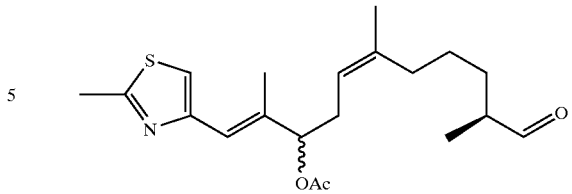

Procedure 1 (Swern-oxidation): 26 μl (38 mg, 0.30 mmol) oxalyl chloride were dissolved in 2.0 mL abs. CH$_2$Cl$_2$ and cooled to −63° C. After addition of a solution of 42 μl (46 mg, 0.59 mmol) abs. DMSO in 0.5 mL abs. CH$_2$Cl$_2$, the mixture was stirred for 10 min at −63° C. and a solution of 99 mg (0.27 mmol) 3-acetoxy-11-hydroxy-2,6,10-trimethyl-1-(2-methyl-thiazol-4-yl)-undeca-1,5-diene (270e) in 1.0 mL abs. CH$_2$Cl$_2$ was added dropwise. Then the mixture was stirred at −63° C. for an additional 30 minutes before 187 μl (137 mg, 1.35 mmol) triethylamine were added. Finally the mixture was allowed to reach ambient temperature and stirred for one more hour.

Then 5.0 mL water were added, the layers separated and the water layer extracted twice with 5.0 mL CH$_2$Cl$_2$. The combined organic layers were washed with saturated NH$_4$Cl-solution (2×4.5 mL), with water (1×4.5 ml) and with brine (1×4.5 mL). After drying over Na$_2$SO$_4$, filtration and concentrating in vacuo, the obtained oil was purified by flash chromatography (column dimensions: 2.0×20.0 cm, ethyl acetate/petroleum ether 1:2).

Yield 74 mg (0.204 mmol, 75%) colorless oil.

Procedure 2 (SO$_3$.Py/DMSO): A solution of 377 mg (1.031 mmol) 3-acetoxy-11-hydroxy-2,6,10-trimethyl-1-(2-methyl-thiazol-4-yl)-undeca-1,5-diene (270e) and 715 μl (522 mg, 5.157 mmol) triethylamine in 12.5 mL abs. CH$_2$Cl$_2$ and 4.2 mL DMSO was cooled to 0° C. Then 657 mg (4.123 mmol) of SO$_3$.Py complex were added at once and the resulting solution was stirred 30 min at 0° C. Finally, 100 mL diethylether were added and the organic layer was washed twice with 50 mL demi water as well as once with 50 mL brine. After drying over Na$_2$SO$_4$, filtration and concentrating in vacuo, the obtained oil was purified by flash chromatography (column dimensions: 2.0×20.0 cm, ethyl acetate/petroleum ether=1:2).

| Yield | 348 mg (0.957 mmol, 93%) colourless oil |
|---|---|
| MS (ESI-MS): | m/z (%) = 386.1 (48) [M + Na]$^+$, 364.1 (100) [M + H]$^+$, 304 (33) [M + H—AcOH]$^+$. |
| C$_{20}$H$_{29}$NO$_3$S | (363.52) |

1-Acetoxy-9-hydroxy-13,13-dimethoxy-4,8,10,12,12-pentamethyl-1-[1-methyl-2-(2-methyl-thiazol-4-yl)-vinyl]-11-oxo-3-tridecene

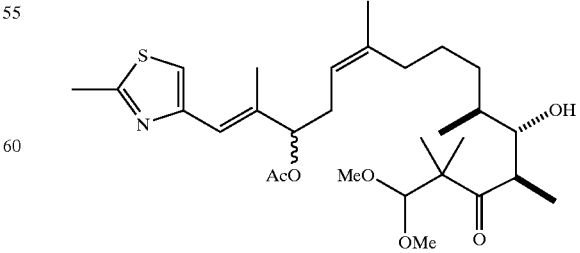

To a suspension of 39 mg (0.316 mmol) CrCl$_2$ and 40 mg (0.299 mmol) LiI in 1.0 mL absolute THF was added a solution of 51 mg (0.140 mmol) 3-acetoxy-2,6,10-trimethyl-1-(2-methyl-thiazol-4-yl)-11-oxo-undeca-1,5-diene (8b) in 1.0 mL absolute THF. After five minutes stirring at ambient temperature, 37 mg (0.147 mmol) 4-bromo-1,1-dimethoxy-2,2-dimethyl-pentan-3-one (225) were added. After stirring for 3 h 40 min at ambient temperature, 2.5 mL brine were added and stirring was continued for five minutes. The waterphase was extracted five times with 2.0 mL of a pentane-diethylether-mixture (1:5) and the combined organic layers were washed three times with 2.0 mL saturated NH$_4$Cl solution. After drying over Na$_2$SO$_4$, filtration and concentrating in vacuo, the obtained oil was purified by flash chromatography (column dimensions: 1.0×20.0 cm, diethylether/petroleum ether=5:4). Two fractions were collected, fraction A containing only the major diastereomer, fraction B containing the major and the minor diasteromer.

Diastereomer a

| Yield | 24 mg (0.045 mmol, 32%) colorless oil |
|---|---|
| MS (CI, isobut): | m/z (%) = 538 (0.86) [M + H]$^+$, 506 (0.55) [—OMe], 478 |

(1.14) [—AcOH], 446 (1.41) [—AcOH, -MeOH], 364 (0.86), 304 (1.84), 279 (2.12), 265 (3.53), 253 (8.35), 241 (2.82), 225 (3.68), 210 (11.76), 168 (30.43), 164 (21.74), 128 (100.00).

| HRMS: | calculated for C$_{29}$H$_{48}$NO$_6$S (MH$^+$): | 538.32025 |
|---|---|---|
| | found: | 538.322854 |
| C$_{29}$H$_{47}$NO$_6$S | (537.75) | |

Mixture of Diastereomers a and b
Yield 25 mg (0.046 mmol, 33%) colourless oil.
15-Acetoxy-3-(tert-butyl-dimethyl-silanyloxy)-7-hydroxy-4,4,6,8,12-pentamethyl-5,16-dioxo-heptadec-12-enoic acid methyl ester

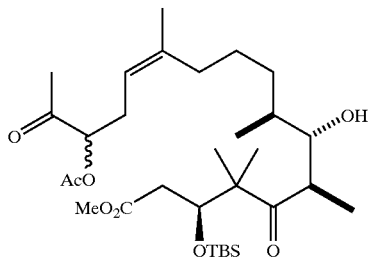

To a suspension of 79 mg (0.640 mmol) CrCl$_2$ and 41 mg (0.306 mmol) LiI in 2.0 mL absolute THF were added 51 mg (0.140 mmol) 3-acetoxy-6,10-dimethyl-11-oxo-5-undecen-2-one (285). After ten minutes stirring at ambient temperature, a solution of 37 mg (0.147 mmol) (3S)-6-bromo-3-(tert-butyl-dimethyl-silanyloxy)-4,4-dimethyl-5-oxo-heptanoic acid methyl ester (235) in 1.0 mL THF was added. After stirring for three hours at ambient temperature, 3.0 mL brine were added and stirring was continued for five minutes. The waterphase was extracted five times with 3.0 mL of a pentane-diethylether-mixture (1:5) and the combined organic layers were washed three times with 3.0 mL saturated NH$_4$Cl solution. After drying over Na$_2$SO$_4$, filtration and concentrating in vacuo, the obtained oil was purified by flash chromatography (column dimensions: 2.0×20.0 cm, diethylether/petroleum ether=1:1).

| Yield | 52 mg (0.089 mmol, 64%) colorless oil |
|---|---|
| C$_{31}$H$_{56}$O$_8$Si | (584.86) |

15-Acetoxy-3-(tert-butyl-dimethyl-silanyloxy)-7-hydroxy-4,4,6,8,12,16-hexamethyl-17-(2-methyl-thiazol-4-yl)-5-oxo-heptadeca-12,16-dienoic acid methyl ester

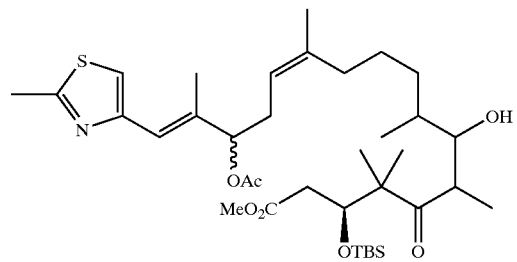

To a suspension of 240 mg (1.95 mmol) CrCl$_2$ and 125 mg (0.93 mmol) in 10.0 mL absolute THF was added 322 mg (0.886 mmol) 3-acetoxy-2,6,10-trimethyl-1-(2-methyl-thiazol-4-yl)-11-oxo-undeca-1,5-diene (8 b) in 1.0 mL absolute THF and 384 mg (0.971 mmol) (3S)-6-bromo-3-(tert-butyl-dimethyl-silanyloxy)-4,4-dimethyl-5-oxo-heptanoic acid methyl ester (235) at ambient temperature. After stirring for 2 h 15 min at ambient temperature, 12 mL brine were added and stirring was continued for five minutes. The waterphase was extracted five times with 15 mL of a pentane-diethylether-mixture (1:5) and the combined organic layers were washed twice with 20 mL demi water and twice with 20 mL brine. After drying over Na$_2$SO$_4$, filtration and concentrating in vacuo, the obtained oil was purified by flash chromatography (column dimensions: 2.0× 20.0 cm, diethylether/petroleum ether=5:4).

| Yield | 161 mg (0.60 mmol, 60%) colourless oil |
|---|---|
| MS (ESI-MS): | m/z (%) = 702.3 (100) [M + Na]$^+$, 680.3 (28) [M + H]$^+$, 620.3 (26) [M + H—AcOH]$^+$. |
| C$_{36}$H$_{61}$NO$_7$Ssi | (680.02) |

15-Acetoxy-3-(tert-butyl-dimethyl-silanyloxy)-4,4,6,8,12,16-hexamethyl-17-(2-methyl-thiazol-4-yl)-5-oxo-7-triethylsilanyloxy-heptadeca-12,16-dienoic acid methyl ester

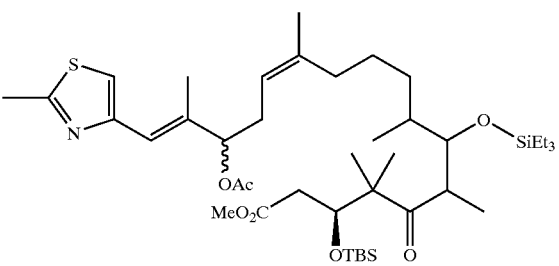

A solution of 115 mg (0.17 mmol) 15-acetoxy-3-(tert-butyl-dimethyl-silanyloxy)-7-hydroxy-4,4,6,8,12,16-hexamethyl-17-(2-methyl-thiazol-4-yl)-5-oxo-heptadeca-12,16-dienoic acid methyl ester (289) and 36 mg (0.50 mmol) imidazole in 1000 μl absolute DMF was cooled to 0° C. After addition of 84 μl (0.50 mmol) triethylsilylchloride, the icebath was removed and the solution was stirred for 3 h 15 min at ambient temperature before 5.0 mL diethylether were added. The organic layer was washed with demi water (2×1000 μl) as well as with brine (1×1000 μl), dried over Na$_2$SO$_4$, filtrated and concentrated in vacuo. The remaining oil was purified via flash chromatography (column dimensions: 1.0×20.0 cm, diethylether/petroleum ether=1:1).

| Yield | 138 mg (0.17 mmol, 100%) colorless oil |
|---|---|
| MS (ESI-MS): | m/z (%) = 794.4 (100) [M + H]$^+$, 756.4 (8), 734.4 (13) [—AcOH]. |
| C$_{42}$H$_{75}$NO$_7$SSi$_2$ | (794.28) |

Lipase Resolution of Acyloin Esters
5-Acetoxy-pentan-4-one

According to the general alkylation method, tert-butyl-2-acetoxy-aceto-acetate (219a) (1.08 g, 5.00 mmol), NaH (156 mg, 6.5 mmol) and ethylbromide (also propyl and pentyl) (373 μL, 549 mg, 5.00 mmol) were reacted in DMF (10 mL) to give 2-acetoxy-2-acetylbutanoic-acid-tert-butylester (250g) (970 mg, 3.97 mmol, 79%) as a slightly yellow oil. Then, 250 g (1.40 g, 5.73 mmol) and 109 mg (0.57 mmol) p-TsOH.H$_2$O were stirred in 18.0 mL benzene according to decarboxylation method A. Kugelrohr distillation gave 486 mg (3.4 mmol, 59%) of 251 g as a colorless oil.

MS (CI): m/z (%)=43 (39), 45 (22), 57 (34), 91 (19), 119 (10), 145 (9), 173 (9), 189 (14), 190 (78), 191 (18), 233 (45), 246 (22), 251 (100), 252 (11), 307 (44).

HRMS: calculated for C$_{17}$H$_{23}$O$_5$ (MH$^+$): 307.15454 found: 307.15070.

5-Acetoxy-hexan-4-one

According to the general alkylation method, tert-butyl-2-acetoxy-aceto-acetate (219a) (7.12 g, 32.9 mmol), NaH (900 mg, 37.5 mmol) and propylbromide (4.05 g, 32.9 mmol) were reacted in DMF (64 mL) to give 2-acetoxy-2-acetyl-pentanoic-acid-tert-butylester (250h) (6.00 g, 23.2 mmol, 71%) as a slightly yellow oil after Kugelrohr distillation at 160° C. and 1.0 mbar. Then, 250h (6.00 g, 23.2 mmol) and 393 mg (2.07 mmol) p-TsOH.H$_2$O were stirred in 60 mL benzene according to decarboxylation method A. Kugelrohr distillation at 1.0 mbar and 150° C., followed by column chromatography (diethylether:petroleum ether=1:8) gave 251h (2.00 g, 12.6 mmol, 54%) as a colorless oil.

5-Acetoxy-heptan-4-one

According to the general alkylation method, tert-butyl-2-acetoxy-aceto-acetate (219a) (1.08 g, 5.00 mmol), NaH (156 mg, 6.5 mmol) and butylbromide (538 μL, 685 mg, 5.00 mmol) were reacted in DMF (10 mL) to give 2-acetoxy-2-acetyl-hexanoic-acid-tert-butylester (250i) (1026 mg, 3.77 mmol, 75%) as a slightly yellow oil. Then, 250i (731 mg, 2.68 mmol) and 51 mg (0.27 mmol) p-TsOH.H$_2$O were stirred in 9.0 mL benzene according to decarboxylation method A. Kugelrohr distillation at 1.0 mbar and 60° C. gave 251i (415 mg, 2.41 mmol, 90%) as a colorless oil.

MS (CI): m/z (%)=143 (26), 157 (11), 169 (13), 173 (100), 174 (12), 185 (18).

HRMS: calculated for C$_9$H$_{17}$O$_3$ (MH$^+$): 173.11777 found: 173.11535

5-Acetoxy-octan-4-one

According to the general alkylation method, tert-butyl-2-acetoxy-aceto-acetate (219a) (7.12 g, 32.9 mmol), NaH (900 mg, 37.5 mmol) and pentylbromide (4.97 g, 32.9 mmol) were reacted in DMF (64 mL) to give 2-acetoxy-2-acetyl-heptanoic-acid-tert-butylester (250j) (6.40 g, 22.3 mmol, 68%) as a slightly yellow oil after Kugelrohr distillation at 185° C. and 1.0 mbar. Then, 250j (6.40 g, 22.3 mmol) and 402 mg (2.11 mmol) p-TsOH.H$_2$O were stirred in 65 mL benzene according to decarboxylation method A. Kugelrohr distillation at 1.0 mbar and 125° C., followed by column chromatography (ethyl acetate:petroleum ether=1:4) gave 251j (1.6 g, 8.59 mmol, 39%) as a colorless oil.

5-Acetoxy-nonan-4-one

According to the general alkylation method, tert-butyl-2-acetoxy-aceto-acetate (219a) (1.08 g, 5.00 mmol), NaH (156 mg, 6.5 mmol) and hexylbromide (702 μL, 825 mg, 5.00 mmol) were reacted in DMF (10 mL) to give 2-acetoxy-2-acetyl-octanoic-acid-tert-butylester (250k) (1063 mg, 3.54 mmol, 71%) as a slightly yellow oil. Then, 250k (2.19 g, 7.29 mmol) and 139 mg (0.73 mmol) p-TsOH.H$_2$O were stirred in 22.0 mL benzene according to decarboxylation method A. Kugelrohr distillation at 0.8 mbar and 80° C. and subsequent flash-chromatography (column dimensions: 2.0× 20.0 cm, diethylether/petroleum ether=1:6) gave 251k (419 mg 2.10 mmol, 29%) as a colorless oil.

MS (CI): m/z (%)=113 (28), 142 (12), 158 (15), 171 (29), 185 (16), 201 (100), 202 (12).

HRMS: calculated for C$_{11}$H$_{21}$O$_3$ (MH$^+$): 201.14906 found: 201.14587.

What is claimed is:

1. An α-hydroxy ketone and/or α-hydroxy aldehyde compound of the general formula I:

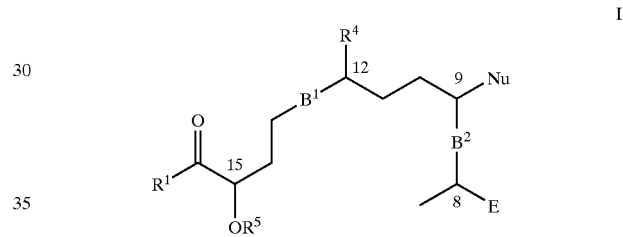

wherein
  R$^1$ is selected from the group consisting of H, methyl, CH$_n$F$_{3-n}$ (n=0–3), ethyl or propyl;
  B$^1$ and/or B$^2$ stands for a single or double bond in the E-(trans) form, Z-(cis) form or E/Z-mixture; or an epoxide as E-(trans) form, Z-(cis) form or E/Z mixture and/or combinations thereof;
  R$^4$ is H, methyl, ethyl, CH$_n$F$_{3-n}$ (n=0–3), or halogen;
  R$^5$ is H or PG;
  Nu is H or alkyl;
  E is CH$_3$, CH$_2$OH, CH$_2$OPG, CO$_2$PG, CO$_2$R or CH═O;
  R is H, methyl or ethyl; and
  PG designates a conventional protective group for the given coupling atom or the given functional group.

2. The compound according to claim 1, wherein B$^1$ stands for a double bond in Z form or an epoxide.

3. The compound according to claim 1 or 2, wherein R$^1$ is methyl.

4. The compound according to claim 1, wherein B$^2$ stands for a single bond.

5. The compound according to claim 1, wherein PG is selected from the froup consisting of: allyl, t-butyl, methyl, benzyl, silyl, acyl, an activated methylene derivative, methoxymethyl, alkoxyalkyl, 2-oxacycloalkyl, trimethylsilyl, triethylsilyl, dimethyl-tert-butylsilyl, acetyl, propionyl, benzoyl and tetrahydropyranyl.

6. The compound according to claim 1, wherein the compound is not racemic, i.e. is optically active at the α-hydroxy position (at position 15) of the general formula I.

7. The compound according to claim 6, wherein the absolute configuration of the α-hydroxy position of the general formula I (at position 15) corresponds to the natural configuration of epothilones at position C15.

8. The compound according to claim 1, wherein the protective group PG is selected from the group consisting of: acetyl, propionyl, butyroyl and benzoyl groups.

9. The compound according to claim 1, wherein the α-hydroxy group (at position 15) of the general formula I is protected by a non-racemic chiral acyl group.

10. The compound according to claim 9, wherein the α-hydroxy group (at position 15) of the general formula I is esterified with optically active 2-methoxy mandelic acid.

11. A method for synthesising compounds according to claim 1, comprising at least one of the following steps:

(a) reacting compounds of general formula II

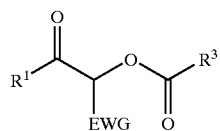
(II)

wherein $R^3$ is selected from the group consisting of: alkyl, benzyl and phenyl or is a chiral, non-racemic residue R*; and EWG is $CO_2PG$;

with an allyl derivative of type A (coupled at X)

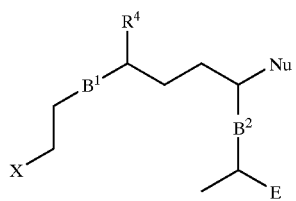
A wherein X is selected from the group consisting of: Cl, Br, I, O-tosyl, methyl sulfonate, trifluor methyl sulfonate, alkanoates and aryl carboxylates;

to compounds with the general formula III

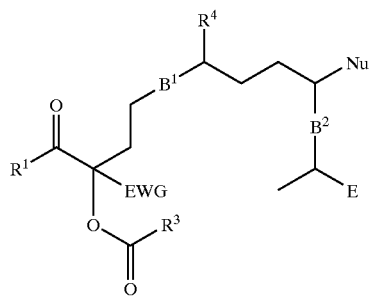
III (b) performing a conversion of compounds of the general formula III to compounds of the general formula IV

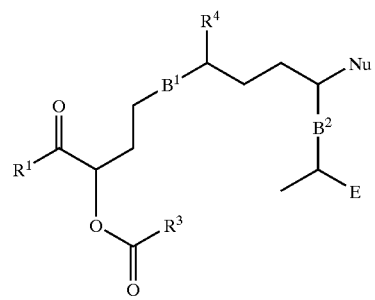
IV by alkyl decarboxylation, sponification or decarboxylation;

(c) performing a solvolysis of the compound of general formula IV to free α-hydroxy ketones of the general formula I; and/or (d) performing a racemate separation by esterification of compounds of the general formula I.

12. The method according to claim 11, wherein $R^3$ is non-racemic chiral acyl group.

13. The method according to claim 11, wherein the production of compounds of the general formula I or IV, which are non-racemic at the α-hydroxy position, is performed by separation of the racemates by enzymatic esterification.

14. The method according to claim 13, wherein the esterification is performed in the presence of an enzyme selected from the group consisting of lipases and esterases.

15. The method according to claim 14, wherein lipases from *Pseudomonas cepacia* and/or *Candida antarctica* or esterases from *Pseudomonas fluorescens* and/or *Streptomyces diastatochromogenes* are used.

16. The method according to claim 11, wherein the production of compounds of the general formula I or IV, which are non-racemic at the α-hydroxy position, is performed by enzymatic hydrolytic racemate separation of compounds of type IV.

17. The method according to claim 16, wherein hydrolysis is performed in the presence of an enzyme selected from the group consisting of: lipases and esterases.

18. The method according to claim 17, wherein lipases from *Pseudomonas cepacia* and/or *Candida antarctica* or esterases from *Pseudomonas fluorescens* and/or *Streptomyces diastatochromogenes* are used.

19. A compound of the general formula XII

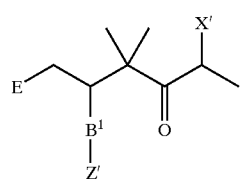
XII wherein $B^1$ is a single or double bond;

E is selected from the group consisting of $CH_2OH$, $CH_2OPG$ and $CH=O$;

X' is selected from the group consisting of Cl, Br, I, O-tosyl, methyl sulfonate, trifluor methyl sulfonate, alkanoates and aryl carboxylates;

Z' is O or OPG; and

PG is a protective group.

* * * * *

UNITED STATES PATENT AND TRADEMARK OFFICE
CERTIFICATE OF CORRECTION

PATENT NO.     : 6,867,333 B2
DATED          : March 15, 2005
INVENTOR(S)    : Wessjohann et al.

It is certified that error appears in the above-identified patent and that said Letters Patent is hereby corrected as shown below:

Column 86,
Line 60, delete "froup" and insert therefore -- group --.

Column 87,
Line 50, after "to" insert therefore -- obtain --.

Column 88,
Line 15, delete "sponification" and insert therefore -- saponification --.

Signed and Sealed this

Sixth Day of September, 2005

JON W. DUDAS
*Director of the United States Patent and Trademark Office*